United States Patent [19]

Brennan et al.

[11] Patent Number: 4,804,782

[45] Date of Patent: Feb. 14, 1989

[54] BRANCHED AMIDES OF L-ASPARTYL-D-AMINO ACID DIPEPTIDES

[75] Inventors: Thomas M. Brennan; Michael E. Hendrick, both of Groton, Conn.

[73] Assignee: Pfizer, Inc., New York, N.Y.

[21] Appl. No.: 796,173

[22] Filed: Nov. 8, 1985

Related U.S. Application Data

[60] Division of Ser. No. 496,428, May 20, 1983, which is a division of Ser. No. 201,745, Nov. 5, 1980, Pat. No. 4,411,925, which is a continuation-in-part of Ser. No. 113,000, Jan. 21, 1980, abandoned.

[51] Int. Cl.$^4$ .................. C07C 103/37; C07C 103/52; A23L 1/236
[52] U.S. Cl. .................................... 564/193; 564/197; 426/548
[58] Field of Search ............................... 564/193, 197

[56] References Cited

U.S. PATENT DOCUMENTS

| | | | |
|---|---|---|---|
| 4,272,536 | 6/1981 | Inamoto et al. | 564/193 |
| 4,277,473 | 7/1981 | Inamoto et al. | 564/193 |
| 4,517,379 | 5/1985 | Brennan et al. | 564/193 |

Primary Examiner—Alan Siegel
Attorney, Agent, or Firm—Connolly and Hutz

[57] ABSTRACT

Amides of L-aspartyl-D-amino acid dipeptides of the formula

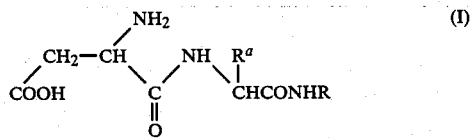

and physiologically acceptable cationic and acid addition salts thereof wherein $R^a$ is methyl, ethyl, n-propyl or isopropyl; R is a branched member selected from the group consisting of fenchyl, diisopropylcarbinyl, d-methyl-t-butylcarbinyl, d-ethyl-t-butylcarbinyl, di-t-butylcarbinyl, 2-methylthio-2,4-dimethylpentan-3-yl,

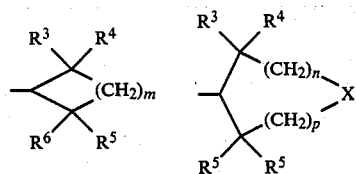

where at least one of $R^3$, $R^4$, $R^5$, $R^6$ is alkyl having from one to four carbon atoms and the remainder are hydrogen or alkyl having from one to four carbon atoms, X is O, S, SO, SO$_2$, C=O or CHOH; m is zero or 1-4, n and p are each zero, 1, 2 or 3 where the sum of n+p is not greater than 3 and the sum of the carbon atoms in $R^3$, $R^4$, $R^5$ and $R^6$ is not greater than six, and when both of $R^3$ and $R^4$ or $R^5$ and $R^6$ are alkyl they are methyl or ethyl,

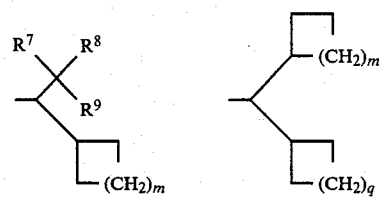

where one of $R^7$, $R^8$, $R^9$ is alkyl having from one to four carbon atoms and the remainder are hydrogen or alkyl having from one to four carbon atoms and the sum of the carbon atoms in $R^7$, $R^8$ and $R^9$ is not greater than six, m and q are the same or different and each have the values previously defined for m;

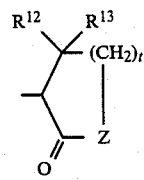

where each of $R^{12}$ and $R^{13}$ are methyl or ethyl, or $R^{12}$ is hydrogen and $R^{13}$ is alkyl having from one to four carbon atoms, Z is O or NH and t is 1 or 2,

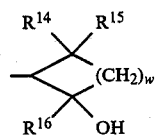

where w is 1-4, $R^{14}$ and $R^{16}$ are each alkyl having from one to four carbon atoms, $R^{15}$ is H, OH, methyl or ethyl and the sum of the carbon atoms in $R^{14}$, $R^{15}$ and $R^{16}$ is not greater than six and when both of $R^{14}$ and $R^{15}$ are alkyl they are methyl or ethyl, and

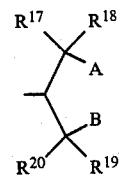

where $R^{17}$ and $R^{19}$ are alkyl having from one to four carbon atoms, $R^{18}$ and $R^{20}$ are H or alkyl having one to two carbon atoms, A is OH and B is H, OH or CH$_3$ and taken together A and B are

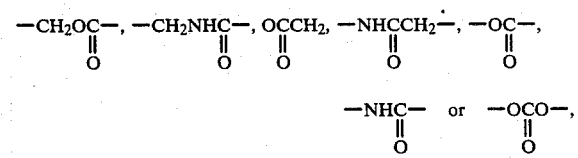

where the sum of the carbon atoms in $R^{17}$, $R^{18}$, $R^{19}$ and $R^{20}$ is not greater than six and when both of $R^{17}$ and $R^{18}$ or $R^{19}$ and $R^{20}$ are alkyl they are methyl or ethyl;

said amides are potent sweetners having advantages over the prior art, edible compositions containing them, methods for their use in edible compositions and novel amine and amide intermediates useful in their production.

3 Claims, No Drawings

BRANCHED AMIDES OF L-ASPARTYL-D-AMINO ACID DIPEPTIDES

CROSS-REFERENCE TO RELATED APPLICATIONS

This application is a division of application Ser. No. 496,428 filed May 20, 1983 which in turn is a division of application Ser. No. 201,745 filed Nov. 5, 1980 now U.S. Pat. No. 4,411,925 issued Oct. 23, 1983, which in turn is a continuation-in-part of application Ser. No. 113,800 filed Jan. 21, 1980 now abandoned.

BACKGROUND OF THE INVENTION

The invention relates to novel amides of L-aspartyl-D-alanine, L-aspartyl-D-2-aminobutyric acid, L-aspartyl-D-valine and L-aspartyl-D-norvaline which are especially useful in view of their potent sweetening properties, novel methods for their use in foods and edible composition containing them.

In U.S. Pat. No. 3,492,131 certain lower alkyl esters of L-aspartyl-L-phenylalanine were found to be up to 200 times as sweet as sucrose and to be substantially free of bitter flavor notes which detracted from earlier artificial sweeteners such as saccharin. These compounds were subsequently found to have only limited stability in aqueous systems due to diketopiperazine formation especially at the neutral-acidic pH conditions prevalent in most food systems.

Mazur et al., *J. Med. Chem.*, 16, 1284 (1973) has disclosed that lower alkyl esters of L-aspartyl-D-alanine and certain homologs thereof, especially L-aspartyl-D-alanine isopropyl ester, have sweetness potencies of up to 125 times sucrose.

Sukehiro et al., *Seikatsu Kagaku*, 11, 9–16 (1977); *Chem. Abstr.*, 87, 168407h (1977) has disclosed certain amides of L-aspartyl-D-alanine of the formula

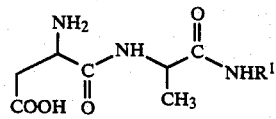

where $R^1$ is methyl, ethyl, n-propyl, isopropyl, n-butyl, isobutyl, secondary butyl, cyclohexyl or the carbon residue of the methyl esters of glycine, d-alanine or l-alanine. The most potent compounds were those wherein $R^1$ is one of the above butyl groups or cyclohexyl, having respectively, 100–125 and 100 times the sweetness of sucrose. Since the n-butylamide was found to have 125 times the sweetness of sucrose and the isobutyl and secondary butyl amides are 100 x sucrose, it was concluded that the potency of these amides is affected mainly by the number of carbon atoms in the alkyl group, $R^1$, and that structural isomerism in the alkyl group has little effect on the sweetness potency.

SUMMARY

Unexpectedly, it has now been found that it is not merely the size of the amide substituent that is critical for a high degree of sweetness in L-aspartyl-D-alanine amides, but, to the contrary, it is the precise spatial arrangement of the amide substituent, R, that is critical. It has been found that certain L-aspartyl-D-alanine amides which are branched at the alpha carbon atom (the carbon atom bearing the amide nitrogen atom) and also branch again at one or both of beta and beta' carbon atoms have significant advantages.

Thus, the present invention provides certain novel branched amides of L-aspartyl-D-alanine and certain other L-aspartyl-D-alpha-alkyl alpha-amino acid dipeptides which have unexpectedly high sweetness potency and are free from undesirable flavor qualities at conventional use levels. They have also been found to have surprisingly high stability both in solid form and in aqueous systems over the pH range found in most food systems even at the elevated temperatures used in baking and conventional food processing.

The novel compounds of the invention are the L-aspartyl-D-amino acid dipeptide amides of the formula

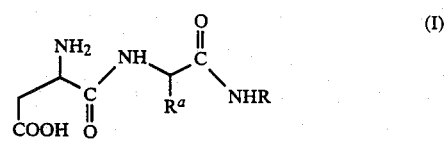

and the physiologically acceptable cationic and acid addition salts thereof, wherein $R^a$ is methyl, ethyl, n-propyl or isopropyl; and R is a branched member selected from the group consisting of fenchyl, diisopropylcarbinyl, d-methyl-t-butylcarbinyl, d-ethyl-t-butylcarbinyl, di-t-butylcarbinyl, 2-methylthio-2,4-dimethylpentan-3-yl,

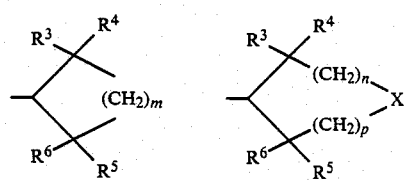

where at least one of $R^3$, $R^4$, $R^5$, $R^6$ is alkyl having from one to four carbon atoms and the remainder are hydrogen or alkyl having from one to four carbon atoms; X is O, S, SO, SO$_2$, C=O or CHOH; m is zero, 1, 2, 3 or 4; n and p are each zero, 1, 2 or 3 and the sum of n+p is not greater than 3; the sum of the carbon atoms in $R^3$, $R^4$, $R^5$ and $R^6$ is not greater than six and when both of $R^3$ and $R^4$ or $R^5$ and $R^6$ are alkyl they are methyl or ethyl;

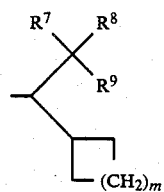

where m is as defined above, one of $R^7$, $R^8$, $R^9$ is alkyl having from one to four carbon atoms and the remainder are hydrogen or alkyl having from one to four carbon atoms and the sum of the carbon atoms in $R^7$, R8 and $R^9$ is not greater than six;

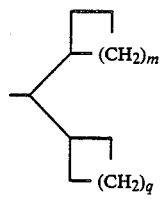

where m and q are the same or different and each have the values previously defined for m;

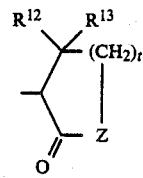

where each of $R^{12}$ and $R^{13}$ are methyl or ethyl, or $R^{12}$ is hydrogen and $R^{13}$ is alkyl having from one to four carbon atoms, z is O or NH and t is 1 or 2;

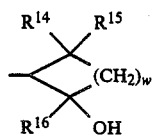

where w is 0, 1, 2, 3 or 4, and are each alkyl having from one to four carbon atoms, $R^{15}$ is hydrogen, OH or alkyl having from one to two carbon atoms, where the sum of the carbon atoms in $R^{14}$, $R^{15}$ and $R^{16}$ is not greater than six and when both of $R^{14}$ and $R^{15}$ are alkyl they are methyl or ethyl; and

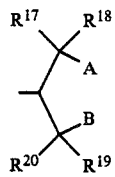

where $R^{17}$ and $R^{19}$ are alkyl having from one to four carbon atoms, $R^{18}$ and $R^{20}$ are hydrogen or alkyl having from one to two carbon atoms, taken separately, A is OH and B is hydrogen, OH or methyl and when taken together A and B are

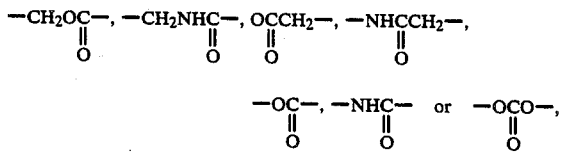

where the sum of the carbon atoms in $R^{17}$, $R^{18}$, $R^{19}$ and $R^{20}$ is not greater than six and when both of $R^{17}$ and $R^{18}$ or $R^{19}$ and $R^{20}$ are alkyl they are methyl or ethyl.

While the preferred sweeteners of the invention are those dipeptide amides of formula (I) wherein the aspartylamino acid dipeptide moiety is derived from L-aspartic acid and a D-amino acid, $R^aCH(NH_2)COOH$, also included within the scope of the invention are mixtures containing the most preferred L-aspartyl-D-amino acid amides of formula (I) wherein one or both of the aspartyl or the other amino acid (i.e., alanine 2-aminobutyric acid, valine or norvaline) moieties is racemic such as e.g., DL-aspartyl-D-alanine amides,
DL-aspartyl-DL-alanine amides,
L-aspartyl-DL-alanine amides,
L-aspartyl-DL-valine amides,
DL-aspartyl-DL-2-aminobutyryl amides, and
DL-aspartyl-D-norvaline amides.

Those compounds of formula (I) wherein the aspartyl moiety is entirely of the D-configuration or the other amino acid moiety is entirely of the L-configuration have little or no sweetness.

An especially preferred group of L-aspartyl-D-amino acid amides of formula (I) are those wherein R is an acyclic member selected from the group consisting of diisopropylcarbinyl, d-methyl-t-butylcarbinyl and di-t-butylcarbinyl.

Another especially preferred group of L-aspartyl-D-amino acid amides of formula (I) are those wherein R is a member selected from the group consisting of

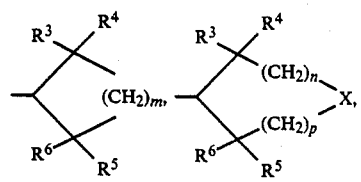

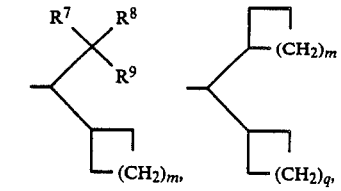

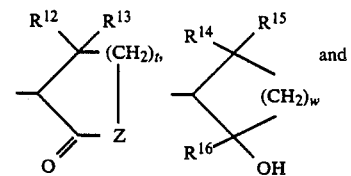

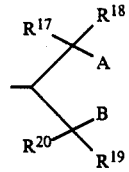

wherein $R^3-R^9$, $R^{12}-R^{20}$, A, B, X, Z, m, n, p, q, t and w are as defined above; and more particularly preferred are those compounds of formula (I) wherein R has one of the first four values of the group immediately above.

Particularly preferred amides of formula (I) are the L-aspartyl-D-alanine amides, i.e., those wherein $R^a$ is methyl.

Examples of the more valuable L-aspartyl-D-amino acid dipeptide amides of the invention include those of formula (I) wherein $R^a$ is methyl and R is:
(-)fenchyl,
diisopropylcarbinyl,
d-methyl-t-butylcarbinyl, di-t-butylcarbinyl,
2,6-diethylcyclohexyl,
2-methylcyclopentyl,
2-ethyl-6-methylcyclohexyl,
2-ethylcyclohexyl,
2-methylcyclohexyl,
2,2-dimethylcyclohexyl,
2-ethylcyclopentyl,
2-methyl-6-isopropylcyclohexyl,
2,2,6,6-tetramethylcyclohexyl,
2,2,4,4-tetramethyltetrahydrofuran-3-yl,
2,2,6-trimethylcyclohexyl,
2-isopropylcyclohexyl,
2,5-dimethylcyclopentyl,
2,6-dimethylcyclohexyl,
2-isopropylcyclopentyl,
2,2,5,5-tetramethylcyclopentyl,
t-butlycyclopropylcarbinyl,
2,2,4,4-tetramethylthietan-3-yl,
2,2,4,4-tetramethyl-1,1-dioxothietan-3-yl,
2,2,4,4-tetramethyltetrahydrothiophene-3-yl,
3,5-dimethyltetrahydrothiapyran-4-yl,
2-t-butylcyclohexyl or dicyclopropylcarbinyl; those wherein $R^a$ is ethyl, isopropyl or n-propyl and R is:
diisopropylcarbinyl,
d-methyl-t-butylcarbinyl,
di-t-butylcarbinyl,
dicyclopropylcarbinyl,
2,2,4,4-tetramethylthietan-3-yl, or
2,2,4,4-tetramethyl-1,1-dioxothietan-3-yl.

Especially valuable sweeteners include the above compounds wherein $R^a$ is methyl and R is: di-t-butylcarbinyl,
2,2,6-trimethylcyclohexyl,
2-t-butylcyclohexyl,
2-isopropylcyclohexyl,
2,6-dimethylcyclohexyl,
2,5-dimethylcyclopentyl,
2-isopropylcyclopentyl,
2,2,5,5-tetramethylcyclopentyl,
2,2,4,4-tetramethyltetrahydrothiophene-3-yl,
t-butylcyclopropylcarbinyl,
dicyclopropylcarbinyl,
2,2,4,4-tetramethylthietane-3-yl or
2,2,4,4-tetramethyl-1,1-dioxothietan-3-yl, and the compound of formula (I) wherein $R^a$ is ethyl and R is 2,2,4,4-tetramethyl-1,1-dioxothietan-3-yl, each of which is at least 400 times as sweet as sucrose.

Most particularly preferred are those compounds of formula (I) wherein $R^a$ is methyl and R is:
2,2,5,5-tetramethylcyclopentyl,
2,2,4,4-tetramethyltetrahydrothiophene-3-yl,
t-butylcyclopropylcarbinyl,
dicyclopropylcarbinyl,
2,2,4,4-tetramethylthietane-3-yl,
2,2,4,4-tetramethyl-1,1-dioxothietan-3-yl, and the compound of formula (I) wherein $R^a$ is ethyl and R is 2,2,4,4-tetramethyl-1,1-dioxothietan-3-yl. Each of the latter group of L-aspartyl-D-amino acid dipeptide amides have sweetness potencies of about 500–2000 times that of sucrose.

The invention further provides compositions for sweetening edible materials which comprises a sweetening amount of a compound of formula (I) and a non-toxic carrier. Most particularly preferred compositions are those containing L-aspartyl-D-alanine N-(dicyclopropylcarbinyl)amide, L-aspartyl-D-alanine N-(2,2,4,4-tetramethylthietane-3-yl)amide, the 1,1-dioxo derivative of the latter.

Additionally, sweetened edible compositions comprising an edible material and a sweetening amount of a compound of the invention, are provided.

Also provided is a method for sweetening edible compositions which comprises adding thereto a sweetening amount of a compound of the invention.

The invention further provides compositions for sweetening edible materials which comprises a sweetening amount of a mixture of a compound of formula (I) and saccharin or a physiologically acceptable salt thereof.

Especially preferred such mixtures are those wherein in said compound of formula (I), $R^a$ is methyl and R is dicyclopropylcarbinyl, 2,2,4,4-tetramethylthietan-3-yl or 2,2,4,4-tetramethyl-1,1-dioxothietan-3-yl. Most particularly preferred are mixtures of L-aspartyl-D-alanine N-(dicyclopropylcarbinyl)amide and said saccharin, especially those wherein said compound and said saccharin are present in a weight ratio of from 1:1 to 1:9.

By physiologically acceptable salts of saccharin is meant the salts of saccharin with physiologically acceptable cations such as e.g., the sodium, potassium, calcium or ammonium salts.

By physiologically acceptable cationic salts of the compounds of the invention is meant the salts formed by neutralization of the free carboxylic acid group of the compounds of formula (I) by bases of physiologically acceptable metals, ammonia and amines. Examples of such metals are sodium, potassium, calcium and magnesium. Examples of such amines are N-methylglucamine and ethanolamine.

By the term physiologically acceptable acid addition salts is meant those salts formed between the free amino group of the compound of formula (I) and a physiologically acceptable acid. Examples of such acids are acetic, benzoic, hydrobromic, hydrochloric, citric, fumaric, gluconic, lactic, maleic, malic, nitric, phosphoric, saccharic, succinic and tartaric acids.

The invention still further provides novel intermediate amines of the formulae below:

$R^b$NH where $R^b$ is d-ethyl-t-butylcarbinyl, cyclopropyl-t-butylcarbinyl or cyclopentyl-t-butylcarbinyl;

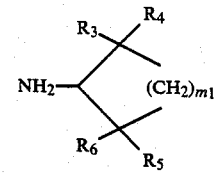

where $m_1$ is 1, 2 or 3 and
when $m_1$ is 1: $R_3$–$R_6$ are each methyl,
when $m_1$ is 2: $R_3$ is methyl, ethyl or isopropyl and $R_4$–$R_6$ are each hydrogen, and
when $m_1$ is 3: $R_3$ is t-butyl and $R_4$–$R_6$ are each hydrogen;

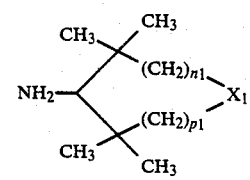

where when $n_1$ is zero and $p_1$ is 1, $X_1$ is O, S or $SO_2$ and when $n_1$ and $p_1$ are each zero, $X_1$ is S, $SO_2$ or C=O;

Further valuable novel intermediates, useful in preparation of the invention compounds, are the D-amino acid amides of the formula

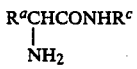

where $R^a$ is as previously defined, and $R_c$ is a member selected from the group consisting of fenchyl, diisopropylcarbinyl, d-methyl-t-butylcarbinyl, d-ethyl-t-butylcarbinyl, di-t-butylcarbinyl, cyclopropyl-t-butylcarbinyl, cyclopentyl-t-butylcarbinyl, dicyclo-propylcarbinyl,

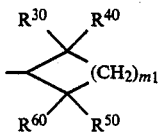

where $m_1$ is 1, 2 or 3 and
when $m_1$ is 1: $R^{30}$, $R^{40}$, $R^{50}$ and $R^{60}$ are each methyl,
when $m_1$ is 2: $R^{30}$ is methyl, ethyl or isopropyl and $R^{40}$, $R^{50}$ and $R^{60}$ are each hydrogen or $R^{30}$ and $R^{50}$ are each methyl and $R^{40}$ and $R^{60}$ are each hydrogen, and
when m is 3:
(a) $R^{30}$ is isopropyl or t-butyl, $R^{40}$, $R^{50}$ and $R^{60}$ are each hydrogen,
(b) $R^{30}$ is ethyl, $R^{50}$ is methyl, $R^{40}$ and $R^{60}$ are each hydrogen, or
(c) $R^{30}$ and $R^{40}$ are each methyl and $R^{50}$ and $R^{60}$ are each hydrogen or methyl, and

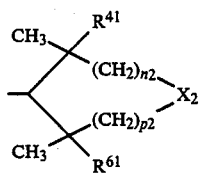

where when $n_2$ and $p_2$ are each zero: $R^{41}$ and $R^{61}$ are each methyl and $X_2$ is S, $SO_2$, C=O or CHOH,
when $n_2$ is zero and $p_2$ is 1: $R^{41}$ and $R^{61}$ are each methyl and $X_2$ is O, S, or SO, and
when $n_2$ is 1 and $p_2$ is 1: $R^{41}$ and $R^{61}$ are each hydrogen and $X_2$ is S or $SO_2$.

The suffix "carbinyl" as used herein denotes the moiety —CH—. Thus, for example, diisopropylcarbinyl is the group $(i\text{-}C_3H_7)_2$—CH— and dicyclopropylcarbinylamine is $(\Delta)_2CHNH_2$

DETAILED DESCRIPTION OF THE INVENTION

The instant dipeptide amides are conveniently manufactured by methods suitable for coupling of amino acids. A preferred method for preparing the dipeptide amides of formula (I) is outlined below.

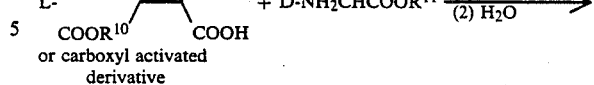

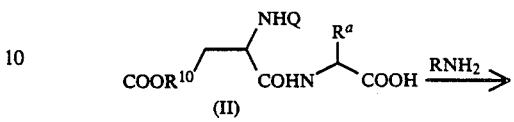

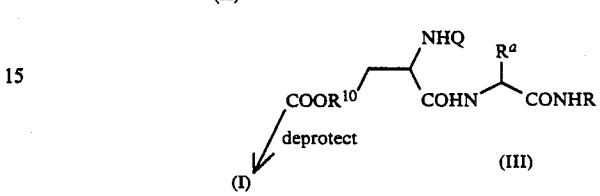

In the above L-aspartic acid derivatives Q is one of the well known amino-protecting groups which can be selectively removed such as those described by Boissonnas, *Advances in Organic Chem.*, 3, 159–190 (1963). Particularly preferred amino-protecting groups are benzyloxycarbonyl and tert-butyloxycarbonyl. $R^1$ is preferably an alkyl group having from one to four carbon atoms or benzyl. The D-alanine, D-2-aminobutyric acid, D-valine or D-norvaline employed may be in the form of the free amino acid wherein $R^{11}$ is hydrogen, but is preferably a carboxyl-protected derivative wherein $R^{11}$ may be the residue of an ester group such as methyl or ethyl, but is preferably a silyl group such as trialkylsilyl, having from three to twelve carbon atoms. An especially preferred such group is trimethylsilyl for reasons of economy and efficiency.

In the first step of the above reaction sequence the diprotected L-aspartic acid is condensed with the appropriate D-amino acid or a carboxy-protected derivative to provide the diprotected dipeptide of formula (II). While this step may be carried out with the diprotected aspartic acid in the presence of condensing agents such as, for example, dicyclohexylcarbodiimide, it is preferred to employ an alphacarboxyl activated derivative of the diprotected aspartic acid. Preferred such carboxyl activated derivatives are the chloride, bromide, anhydride or mixed anhydride. Especially preferred for reasons of efficiency are the mixed anhydrides of the above diprotected-L-aspartic acids with esters of chlorocarbonic acid, particularly the alkyl esters wherein said alkyl has from one to four carbon atoms. Most preferred mixed anhydrides are those prepared from the methyl and ethyl esters of chlorocarbonic acid for reasons of economy.

In a particularly preferred method for preparing the compounds of formula (I), beta-benzyl-N-benzyloxycarbonyl-L-aspartic acid is reacted with ethyl chlorocarbonate to form the corresponding mixed anhydride by methods known in the art. In a separate vessel the D-amino acid, $R^aCH(NH_2)COOH$, which is obtained from commercial sources or by resolution of the racemic amino acid by known methods [see e.g. Yamada et al., *J. Org. Chem.*, 38, 4408 (1973)], is converted to the trimethylsilyl ester by contacting the amino acid with an equimolar amount of trimethylsilyl chloride in the presence of a reaction inert organic solvent. Suitable solvents for this purpose are, for example, pyridine, dimethylformamide or dimethylacetamide; especially preferred is dimethylformamide.

In a typical reaction according to this method, the D-amino acid e.g., D-alanine, dissolved in dimethylformamide and an equimolar amount of trimethylchlorosilane is added at room temperature. In a separate flask beta-benzyl N-benzyloxycarbonyl-L-aspartic acid and a molar excess of an acid binding agent, preferably triethylamine are dissolved a mixture of dimethylformamide and tetrahydrofuran and an equimolar amount of ethylchlorocarbonate is added at room temperature or below, preferably at about $-25°$ to $25°$ C. and especially at about $-10°$ to $0°$ C. to form the mixed anhydride. To this is added the solution of e.g., D-alanine trimethylsilyl ester, preferably at a temperature within the same range. Reaction is ordinarly complete within one to two hours after which the reaction mixture is poured into water or aqueous acid, for example hydrochloric acid, and the product of formula (II) extracted with a water immiscible solvent, typically chloroform, methylene chloride or ethyl ether and isolated by standard methods. The diblocked dipeptide (II) is ordinarily of sufficient purity for use in the next step, but may be further purified if desired, for example by column chromatography.

In the second step of this method the diblocked dipeptide (II) is reacted with an equimolar amount of primary amine of formula $RNH_2$ to provide the corresponding diblocked dipeptide amide intermediate of formula (III) wherein $R^a$, R, $R^{10}$ and Q are as previously defined. As in the first step, the carboxylic acid form of the reactant (II) can be successfully employed by use of condensing agents, for example dicyclohexylcarbodiimide to provide the intermediates of formula (II). However, it is preferred to convert the compound of formula (II) to a carboxyl activated derivative, for example the chloride, bromide or mixed anhydride, the latter being preferred. Thus, employing the particularly preferred compound of formula (II) wherein is benzyl and Q is benzyloxycarbonyl, the mixed anhydride is prepared. As above, the preferred anhydrides are those obtained from esters of chlorocarbonic acid and the methyl or ethyl esters thereof are particularly preferred. The mixed anhydrides of compound (II) are prepared employing reactants and conditions described above for the first step of this sequence. In a typical recction the compound of formula (II) and triethylamine in approximately equimolar amounts are combined in a reaction inert organic solvent, for example tetrahydrofuran, the mixture cooled to about $-10°$ C. and ethylchlorocarbonate added to obtain the mixed anhydride. To this is then added an equimolar amount of the amine of formula $RNH_2$ or a solution thereof, for example in the same reaction inert solvent and at a temperature in the range of from about $-50°$ to $25°$ C. and preferably at from $-35°$ to $-5°$ C. After the addition of the amine is ccmplete, the reaction mixture is allowed to warm to about room temperature and maintained at this temperature until reaction is substantially ccmplete, ordinarily from about 1 to 20 hours. The desired intermediate of formula (II) is then isolated and purified, if desired, by the same methods described above for compound (II).

In the final step of this method the carboxyl protecting group, and amino protecting group, Q, are removed to provide the desired sweeteners of formula (I).

The method selected for removal of protecting groups from the dipeptide amide of formula (III) will vary depending on a number of factors which will be apparent to those of skill in the art. Two important factors for such selection are the nature of the protecting groups $R^{10}$ and Q, and the nature of the amide substituent, R. For example, when and Q are, respectively, the especially preferred groups benzyl and benzyloxycarbonyl and R does not contain sulfur, a preferred method for removing said protecting groups is, ordinarily, by hydrogenolysis. However, when is benzyl or alkyl as defined above and Q is tert-butyloxycarbonyl and R has any of the values above, it is ordinarly preferred to remove the protecting groups by hydrolysis. A combination of hydrolysis and hydrogenolysis is preferred in those cases wherein $R^{10}$ is alkyl, Q is benzyloxycarbonyl and R does not contain sulfur.

When hydrogenolysis is selected for removal of protecting groups from the intermediate of formula (III) it is preferred to carry out the reaction in the presence of a catalytic amount of a noble metal catalyst, palladium being especially preferred, and in the presence of a reaction inert solvent. Examples of such solvents include the lower alkanols, such as methanol, ethanol, isopropanol and n-butanol; ethers, such as tetrahydrofuran, ethyl ether, 1,2-dimethoxyethane and diethyleneglycol dimethylether; esters such as ethyl acetate, methyl propionate and dimethylsuccinate; and dimethylformamide. Particularly preferred such solvents are methanol and ethanol for reasons of economy and efficiency. While the hydrogenolysis may be carried out successfully at higher pressures and temperatures, use of pressures of from about 1–10 atmospheres and room temperature are preferred for reasons of economy and convenience. At the preferred temperature and pressure the reaction is ordinarily complete in from about 30 minutes to about six hours, after which the catalyst is removed, typically by filtration, the solvent evaporated and the resulting product purified, if desired, by standard methods, for example by recrystallization or column chromatography.

When hydrolysis is selected for removal of one or both of protecting groups and Q any of the well known methods for alkaline hydrolysis or acid hydrolysis of esters and the like may be employed with some success. However, when blocking groups $R^{10}$ are to be removed by hydrolysis alkaline hydrolysis is preferred, and especially preferred conditions are use of at least an equivalent amount of a strong base, for example, sodium hydroxide or potassium hydroxide in the presence of water and a lower alkanol, particularly methanol or ethanol, at or about room temperature. Under these preferred conditions hydrolytic removal of the $R^{10}$ group is ordinarily complete in a few hours or less.

When the amino protecting group Q is tertbutyloxycarbonyl it is preferred to use acid hydrolysis for its removal. Especially preferred is dilute aqueous hydrochloric acid in the presence of methanol or ethanol and heating the mixture at reflux. Under these conditions hydrolysis is ordinarily complete in a few hours or less.

Isolation of the products of formula (I) after removal of protecting groups by any of the above hydrolysis methods employs standard procedures known in the art. For example, after acid hydrolysis the reaction mixture is evaporated to remove solvent, the aqueous residue washed with a water immiscible nonpolar solvent, for example, ethyl ether or chloroform after which the aqueous layer is made alkaline and the product extracted with a water-immiscible solvent such as, for example, ethyl acetate and the product obtained by evaporation of solvent. If desired, the product can be further purified, for example, by recrystallization or column chromatography. When alkaline hydrolysis to remove a protecting group is followed by hydrogenolysis to remove the amino protecting group Q, the reaction mixture from the alkaline hydrolysis is preferably neutralized by addition of acid, for example, hydrochloric acid, and the neutralized reaction mixture subjected to hydrogenolysis as described above.

A second preferred method for manufacture of the instant compounds of formula (I) is shown below.

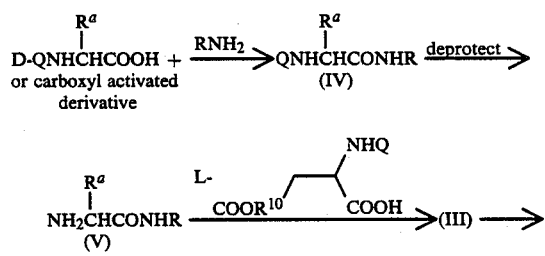

$R^a$, R, $R^{10}$, and Q are as defined above.

The amino protected D-amino acid or its carboxyl activated derivative is reacted with an equimolar amount of amine $RNH_2$ employing methods and conditions described above for the preparation of intermediates (II) and (III) to obtain an amino protected D-amino acid amide of formula (IV). The protecting group Q is removed by hydrogenolysis or hydrolysis as described above and the resulting free amino amide (V) is condensed with a diblocked L-aspartic acid derivative or a carboxyl activated derivative thereof, as described above for the preparation of intermediates of formula (II), to provide the diblocked dipeptide amide of formula (III) from which the desired sweetener of formula (I) is obtained as previously described.

In a modification of this method an intermediate of formula (IV) wherein R contains a cyclic or acyclic sulfide moiety (—S—) may be oxidized to the corresponding sulfoxide or sulfone prior to its conversion to intermediate (V) and subsequent reactions as described above, to provide compounds of formula (I) wherein R is a sulfoxide or sulfone.

In a third preferred method for preparing the compounds of the invention the D-amino acid amide of formula (V), described above, is reacted with L-aspartic acid N-thiocarboxyanhydride to provide directly the compounds of formula (I). In carrying out this method the intermediate (V) in a suitable solvent is contacted with an equimolar amount of L-aspartic acid N-thiocarboxyanhydride at a mildly alkaline pH at a temperature of from about −25° to 10° C. to provide the compound of formula (I). The alkaline pH for this reaction is provided by means of a strong base, for example, sodium hydroxide or potassium carbonate. Suitable solvents for this reaction are those that dissolve at least a portion of the reactants under the reaction conditions employed without reacting with either reactant to an appreciable extent and allow the products formed in the reaction to be isolated with relative ease. Examples of such solvents for this reaction are water, tetrahydrofuran, 1,2-dimethoxyethane, diethyleneglycol dimethylether, dimethylsulfoxide, dimethylformamide and combinations thereof; preferred solvents are water, and its mixtures with tetrahydrofuran. A preferred alkaline pH range for this reaction is from about 8 to 10 and a pH of about 9 is especially preferred. An especially preferred temperature is in the range of about −10° to 0° C.

Under the preferred conditions mentioned above the reaction is ordinarily complete in one to two hours. The product of formula (I) then isolated by standard methods, for example, the pH of the reaction mixture is adjusted to the isoelectric pH of the product, ordinarily about pH 5.0–5.6, to precipitate the product of formula (I), the bulk of the solvent removed by evaporation or filtration and the crude material slurried with an organic solvent, for example, methanol, ethanol, ethyl ether, ethyl acetate or mixtures thereof. The product of formula (I) is then isolated, by filtration for example. It may be further purified, if desired, by, e.g., recrystallization or column chromatography.

The sweetness potency of the instant compounds was determined by comparison of their gustatory sweetnesses with sucrose. Aqueous solutions of the compound of formula (I) diluted to a suitable range of concentrations were compared with a sucrose standard by an expert taste panel. Comparisons were generally made with aqueous sucrose solutions of 7–9%, i.e., 7–9 g. per 100 ml. Higher sucrose concentrations have a distinctive mouthfeel which may influence results and lower sucrose concentration are not indicative of normal use situations. If, for example a 0.014% solution of the compound of formula (I) is judged to be equally as sweet as a 7% sucrose solution, then the sweetness potency of that compound is 7/0.014=500× sucrose. All of the sweetness potency values stated herein for the compounds of the invention were determined by this method. At threshold concentrations (i.e., the lowest concentration at which sweetness is first noticed, which for sucrose is ordinarily at concentrations in the range of 2–3%), the potency of a sweetener, such as the compounds of the invention, is generally twice that observed by comparison of its gustatory sweetness with 7–9% solutions of sucrose.

The requisite amines of formula $RNH_2$ wherein R is as previously defined are either commercially available or can be obtained from readily available precursors. For example, the 2-alkylcyclohexylamines and 2,6-dialkylcyclohexylamines can be obtained by catalytic hydrogenation of the corresponding alkyl substituted anilines. Many of the amines are obtained by reductive amination of the corresponding ketone using a variety of conditions known in the art. For example, reductive amination by the well known Leuckhart reaction employing formic acid and formamide as reducing agents, see for example, the review in *Organic Reactions*, Wiley and Sons, New York, Vol. 5, p. 301, 1949, may be employed. Alternatively, the appropriate ketone can be reductively aminated employing sodium cyanoborohydride and ammonium acetate see for example, *J. Amer. Chem. Soc.*, 93, 2897 (1971), or by means of ethanolic ammonia in the presence of a hydrogenation catalyst such as Raney nickel, platinum or palladium, see, for example, *Organic Reactions*, 4, 174 (1948). Many of the amines of formula $RNH_2$ are obtained from the corresponding ketones by formation of an intermediate oxime formed by reacting the ketone with hydroxylamine or its salts under conditions well known in the art. The oxime intermediate is then reduced by catalytic hydrogenation or by means of sodium in the presence of a lower alkanol at elevated temperature. A particularly preferred method, especially useful for reducing oximes of sulfur-containing ketones, employs reduction of the oxime in ethanol and a molar excess of sodium at the reflux temperature of the mixture.

The requisite ketone precursors of the amines $RNH_2$ are either commercially available, known in the art or prepared by known methods. For example, the ketones of formula (VI) and (VII)

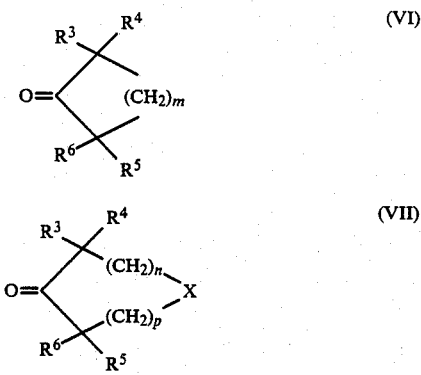

where $R^3$, $R^4$, $R^5$, $R^6$, X, m, n and p are as defined above, except those of formula (VII) wherein X is C=O, may be obtained by alkylation of the corresponding compounds wherein $R^3$, $R^4$, $R^5$ and $R^6$ are each hydrogen to provide compounds of the above formula wherein from one to all of $R^3$, $R^4$, $R^5$, $R^6$ are alkyl as defined above. The alkylation is carried out, for example, employing alkylating agents such as the appropriate alkyl halide or alkyl sulfate under neutral or alkaline conditions provided by strong bases, for example, sodium hydride or sodium amide. Using the same method compounds of the formula (VI) and (VII) wherein only 1, 2 or 3 of the substituents alpha to the keto group are alkyl can be converted to compounds of the same formula wherein from two to four of $R^3$, $R^4$, $R^5$, $R^6$ are alkyl. Gem-dialkyl compounds of formula (VI) and (VII) wherein either $R^3$ and $R^4$ or $R^5$ and $R^6$ are said alkyl can be obtained from the appropriate monoalkyl compound by blocking the unsubstituted alpha-position prior to alkylation and subsequent removal of the blocking group. For example, 2,2-dimethylcyclohexanone may be obtained by condensation of 2-methylcyclohexanone with ethylformate in the presence of sodium methoxide and the resulting intermediate alkylated as outlined below.

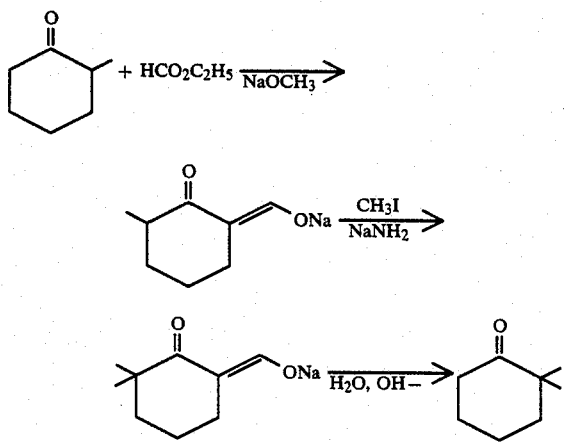

Ketones of formula (VI) or (VII) wherein one or both of $R^3$ and $R^5$ are propyl or butyl may be obtained by condensation of the corresponding alpha-unsubstituted compound with the appropriate aldehyde or ketone under alkaline conditions to an intermediate alpha- or alpha,alpha'-alkylidene ketone which can then be hydrogenated to provide the desired ketone.

The requisite cyclobutanones are obtained by methods described by Conia et al., *Bull. Soc. chim. France*, 726 (1963) and Conia, *Ind. chim. Belge*, 31,981 (1966).

An alternative method for preparing the ketones of formula (VI) and (VII) involves a cyclization of an acyclic precursor. For example, by means of the well known Dieckmann cyclization of dicarboxylate esters and subsequent hydrolysis and decarboxylation; see e.g., *Modern Synthetic Reactions*, W. A. Benjamin, Menlo Park, Cal., 1972, p. 740. The alpha-keto esters produced, especially those with no other alpha-substituent, can also be alkylated prior to hydrolysis and decarboxylation, if desired. This reaction can also be used to provide ketones (VI) and (VII) which are unsubstituted at the carbons adjacent to the carbonyl group which can be alkylated as described above.

For preparation of diketones of formula (VII) wherein X is C=O the keto group of acyclic ketodicarboxylate ester precursor is converted to a ketal or thioketal, e.g., dimethyl ketal, diethylthio ketal, ethylenedioxy ketal or ethylenedithio ketal, prior to Dieckmann cyclization. Ester group hydrolysis and decarboxylation affords a keto-ketal which may be converted to the corresponding amino ketal, by methods described above, followed by hydrolysis of the ketal group by methods well known in the art. The resulting amino ketone can be hydrogenated, if desired, to the corresponding hydroxyamine (X=CHOH) by known methods, e.g. by reduction with sodium borohydride.

2,2,4,4-Tetraalkyl- 3-hydroxycyclobutylamines are prepared from the corresponding 1,3-diones by the method of U.S. Pat. No. 3,125,569.

The amines of formula

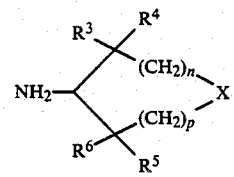

where X is CHOH and $R^3$–$R^6$, n and p are as defined above, or N-protected derivatives thereof e.g., N-benzyloxycarbonyl derivatives, may be oxidized, e.g. by chromium trioxide, to the corresponding compounds wherein X is C=O. Alternatively, the hydroxyamine may be reacted first with a carboxyl activated derivative of an N-protected D-amino acid, D-QNHCH($R^a$)-COOH, where Q and $R^a$ are as previously defined, and the resulting intermediate of formula (IV) wherein R is said hydroxy-containing group, oxidized, e.g., with chromium trioxide, to provide the corresponding ketone. The resulting ketone of formula (IV) is then converted to the desired product of formula (I) where R is a keto-containing group as desired above.

Certain of the ketones of formula (VII) are also obtained from acyclic precursors derived from ketones of the formula (VIII) wherein $R^3$, $R^4$, $R^5$ and $R^6$ are

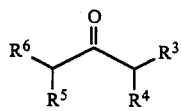
(VIII)

as previously defined. For example four-membered ketones of formula (VII) where X is O or S are obtained by bromination of (VIII) with two moles of bromine and the resulting alpha,alpha'-dibromo compound cyclized with, e.g., sodium hydroxide to provide an oxetanone or hydrogen sulfide to provide a thietanone. The corresponding five-membered ring ketones (VII) are obtained when (VIII) is first reacted with formaldehyde to provide an intermediate alpha-hydroxymethyl compound which is then brominated at the alpha'-position and cyclized with sodium hydroxide or hydrogen sulfide to provide the corresponding compounds of formula (VII) wherein X is O or S, respectively.

Certain of the tetrahydropyran-4-ones and tetrahydrothiapyran-4-ones of formula (VII) are obtained by adding the elements of water or hydrogen sulfide to the appropriately substituted divinylketone.

Ketone intermediates of formula (IX) which may be converted to amines via the oxime are obtained by methods outlined below where $R^{17}$, $R^{18}$, $R^{19}$ and $R^{20}$ are as defined above.

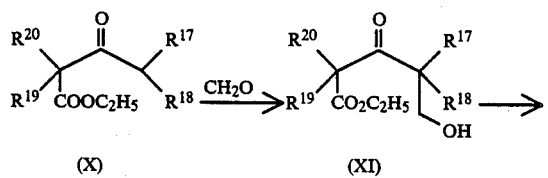

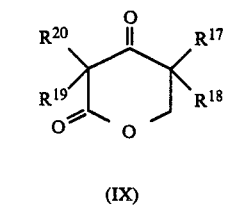

The appropriately substituted acetoacetic ester (X) is condensed with formaldehyde, e.g. under alkaline conditions, and the resulting hydroxmethylated intermediate (XI) is then cyclized, for example by heating in the presence of a mild acid or base with removal of ethanol as it forms.

Bromination of acetoacetic esters of formula (X) and subsequent treatment of the product with, e.g. sodium hydroxide, provides ketones of formula (XII) which are converted to the corresponding amine as described above.

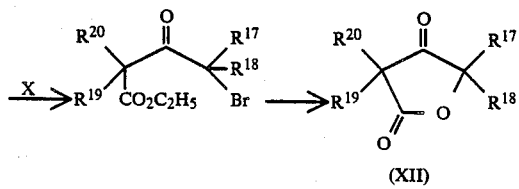

Alternatively, the ketolactones (XII) can be prepared by the method described in Zeit. Chemie, 13, (1973); Chem. Abstr., 78, 135596e (1973), by reaction of the appropriate cyclobutan-1,3-dione with hydrogen peroxide.

The dibromo derivative of (VIII), described above, can also be treated with alkali hydroxides, e.g. sodium hydroxide under mild conditions, to form the corresponding 1,3-dihydroxyketone which is converted to the corresponding 1,3-dioxane-2,5-dione of formula (XIII) by reaction with phosgene.

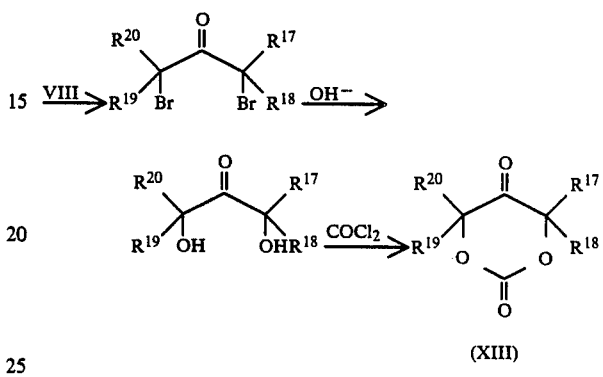

The 5-oximino intermediate of (XIII) upon treatment with sodium in ethanol as described above, provides the corresponding 5-amino compound.

Treatment of a monobromo derivative of ketones of formula (VIII) with, e.g. ethyl malonate, and subsequent hydrolysis, decarboxylation and esterification of resulting product affords intermediates of formula (XIV) which serve as precursors of the ketones (XV) as shown below, for example.

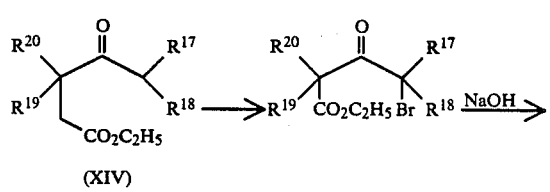

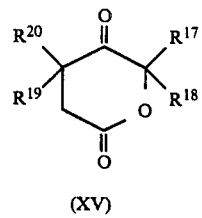

The ketolactones (XV) are then converted to the corresponding 4-amino compound, e.g. by reduction of the oxime, as described above.

The 1,3-dibromoketone derivatives of (VIII), described above, also can be converted to the corresponding 1,3-dimercaptoketone by reaction with at least two moles of sodium hydrosulfide. Treating the dimercaptoketone with reagents such as iodine, hydrogen peroxide or hypochlorous acid under disulfide forming conditions, well known in the art provides the ketones of formula XVI which are converted to amines by reduction of the oxime employing, e.g., sodium in ethanol.

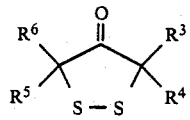
(XVI)

Amines of formula (XVII) are provided directly, for example, by the method of Nagase et al., *Chem. Pharm. Bull.* 17, 398 (1969) as shown below.

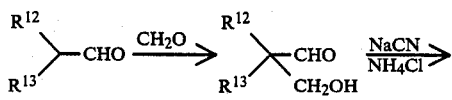

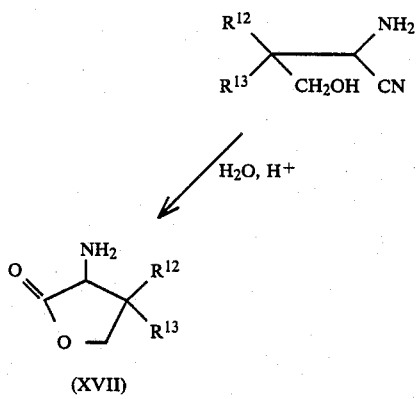

(XVII)

Use of ethylene oxide in place of formaldehyde in the first step of the above reaction sequence affords the corresponding 3-amino-2-pyrones,

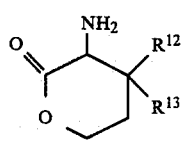

Lactams corresponding to the above lactone intermediates or those of formula (IX), (XII), (XV) or (XVII), are obtained by reaction of the appropriate lactone with ammonia; for example, the above lactone is contacted with an excess of anhydrous ammonia in ethanol and the mixture allowed to stir overnight at ambient temperature to provide compounds of the formula

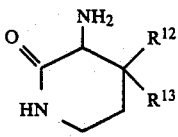

Alternatively, certain lactam intermediates are provided by the following reaction sequence.

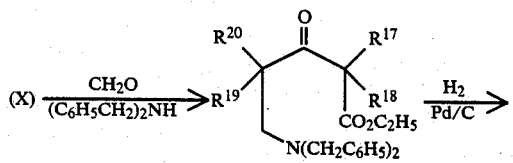

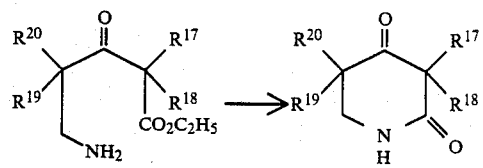

The resulting ketones are then converted to the requisite amines by methods described above. The isomeric ketolactams are obtained by the following reaction sequence:

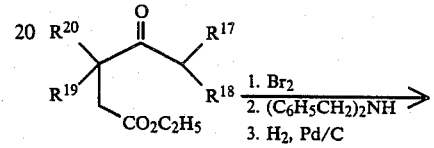

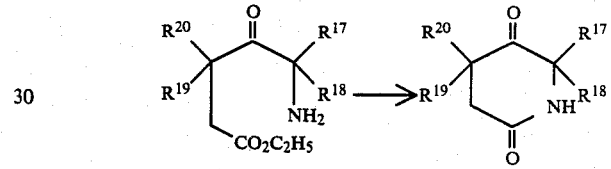

The corresponding 5-membered lactams are also obtained by the method of U.S. Pat. No. 3,125,569:

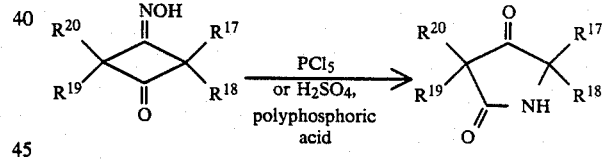

Cyclic or open chain alpha-hydroxyketones or alpha,alpha,-dihydroxyketones of the formula

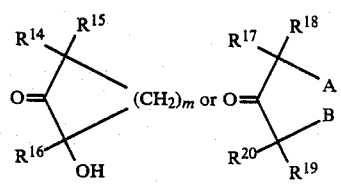

where $R^{14}$–$R^{20}$, m, A and B are as previously defined are prepared by bromination with one or two moles of bromine and treatment of the bromo or dibromo intermediate with an hydroxylic base, e.g., sodium hydroxide or potassium hydroxide as described above. The reaction sequence is exemplified as follows:

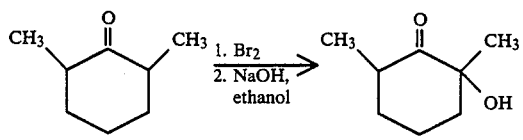

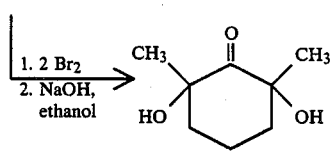

Dicycloalkylketones (XVIII) and alkylcycloalkylketones (XIX) are prepared by the reaction of the appropriate acid halide and Grignard reagent employing conditions and reagents well known in the art, e.g., as shown below.

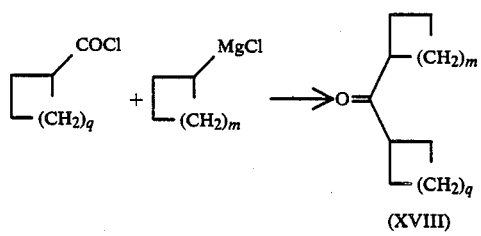

(XVIII)

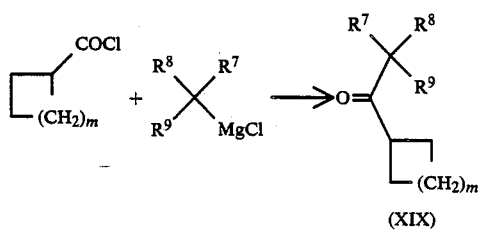

(XIX)

Amines of formula $RNH_2$ where R is as previously defined are also obtained by the well known Hofmann reaction by conversion of the appropriate carboxamide with alkali metal hypohalite. This procedure is specially useful for the preparation of cyclopropylamines. The corresponding cyclopropyl amides are obtained and converted to amines, e.g. as shown below.

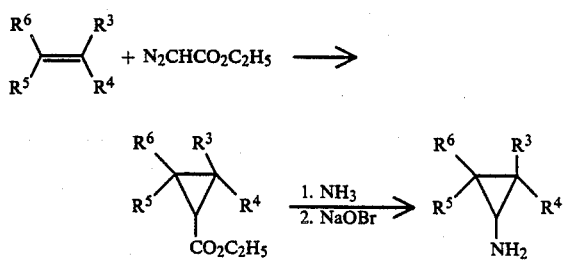

The first step of the above sequence to form the cyclopropylcarboxylic acid ester is known in the art, see for example, Mescheryakov et al., Chem. Abstr., 54, 24436 (1960).

The compounds of formula (I) or intermediate amides therefore, wherein R is

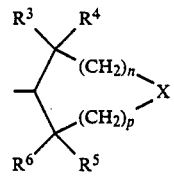

where X is SO or $SO_2$ are obtained from the corresponding compounds wherein X is S by oxidation employing reagents and conditions known to form sulfoxides and sulfones from sulfides. Alternatively, the appropriate ketone of formula (VII) where X is S or the amine derived from said ketone, as described above, can be oxidized to the sulfoxide or sulfone prior to coupling to form the dipeptide amide of formula (I). Preferred reagents and conditions for such oxidation of sulfides include use of hydrogen peroxide in a solvent, for example, acetic acid or acetone. When equimolar amounts of reactants are employed the product is the sulfoxide, which is readily converted to the corresponding sulfone by an additional mole of peroxide. Other preferred oxidants are potassium permangante or chromic acid, for preparation of the sulfones, and m-chloroperbenzoic acid. The latter reagent being especially useful for conversion of the above thioketones (VII) to the corresponding sulfoxide employing one mole of this reagent, or the sulfone when two moles of the peracid are employed.

The compounds of formula (I) and the physiologically acceptable salts thereof provide advantages as sweetening agents in view of their high potency, their physical form and stability. They are, ordinarily, crystalline, non-hygroscopic, water soluble solids. They are uniquely characterized by possessing a sweet taste, devoid of undesirable harsh or bitter flavor qualities at ordinary use levels. They can be usefully employed to impart sweetness to edible materials. The term "edible materials" as used herein signifies all non-toxic substances consumable by humans or other animals, in solid or liquid form. Illustrative of such substances are: foods, including foodstuffs, prepared food items, chewing gum and beverages; food additives, including flavoring and coloring agents as well as flavor enhancers; and pharmaceutical preparations.

The compounds of the invention can be prepared in a variety of forms suitable for utilization of sweetening agents. Typical forms which can be employed are solid forms such as powders, tablets, granules and dragees; and liquid forms such as solutions, suspensions, syrups, emulsions as well as other commonly employed forms particularly suited for combination with edible materials. These forms can consist of the compounds of formula (I) or their physiologically acceptable salts either apart or in association with non-toxic sweetening agent carriers, i.e. non-toxic substances commonly employed in association with sweetening agents. Such suitable carriers include liquids such as water, ethanol, sorbitol, glycerol, citric acid, corn oil, peanut oil, soybean oil, sesame oil, propylene glycol, corn syrup, maple syrup and liquid paraffin, and solids such as lactose, cellulose, starch, dextrin, modified starches, polysaccharides such as polydextrose (see, e.g. U.S. Pat. No. 3,766,165 and U.S. Pat. No. 3,876,794), calcium phosphate (mono-, di- or tri-basic) and calcium sulfate.

Likewise useful and compatible are compositions containing a compound of the invention combined with a known sweetening agent such as, for example, sucrose, saccharin, cyclamate, L-aspartyl-L-phenylalanine methyl ester and the like, useful for sweetening edible materials. Especially useful are the mixtures of compounds of formula (I) and saccharin or a physiologically acceptable salt thereof, e.g., the sodium, potassium, calcium or ammonium salt of saccharin. In said mixtures with saccharin the compounds of formula (I) reduce or completely mask the well known, undesirable bitter aftertaste of the saccharin.

Particularly useful such sweetener compositions are those containing saccharin in admixture with compounds of formula (I) which are at least 400 times as sweet as sucrose, especially those wherein $R^a$ is methyl and R is dicyclopropylcarbinyl, 2,2,4,4-tetramethylthietan-3-yl or 2,2,4,4-tetramethyl-1,1-dioxothietan-3-yl. Most particularly preferred are such mixtures of saccharin and L-aspartyl-D-alanine N-(dicyclopropylcarbinyl)amide, especially such mixtures which contain the latter compound of formula (I) and saccharin in a weight ratio in the range of from 1:1 to 1:9. These mixtures are not only pleasantly sweet tasting and appreciably devoid of bitter aftertaste, they are, unexpectedly, significantly sweeter than calculated by summation of sweetness of the individual components of the mixture. That is, they exhibit a synergist effect, being up to 33% sweeter than calculated. In mixtures of saccharin or its salts and L-aspartyl-D-alanine N-(dicyclopropylcarbinyl)amide in ratios outside the above range the synergist effect is consideraly reduced.

The invention also provides sweetened edible compositions comprising an edible material and a sweetening amount of a compound of formula (I), a physiologically acceptable salt thereof alone or in combination with a non-toxic carrier or known sweetening agent. Examples of specific edible materials which provide such sweetened edible compositions include: fruits, vegetables, juices, meat products such as ham, bacon and sausage; egg products, fruit concentrates, gelatins and gelatin-like products such as jams, jellies, preserves, etc.; milk products such as ice cream, sour cream and sherbet; icings, syrups including molasses; corn, wheat, rye, soybean, oat, rice and barley products such as bread, cereals, pasta, cake and cake mixes; fish, cheese and cheese products, nut meats and nut products, beverages such as coffee, tea, carbonated and non-carbonated soft drinks, beers, wines and other liquors; confections such as candy and fruit flavored drops, condiments such as herbs, spices and seasonings, flavor enhancers such as monosodium glutamate and chewing gum. The instant sweeteners are also of use in prepared packaged products such as dietetic sweeteners, liquid sweeteners, granulated flavor mixes which upon reconstitution with water provides non-carbonated drinks, instant pudding mixes, instant coffee and tea, coffee whiteners, malted milk mixes, pet foods, livestock feed, tobacco and consumable toiletries such as mouth washes and toothpaste as well as proprietary and non-proprietary pharmaceutical preparations and other products of the food, pharmaceutical and sundry industries.

Especially preferred sweetened edible compositions are carbonated beverages containing one or more of the instant sweeteners.

The invention is further illustrated by the following examples.

EXAMPLE 1

Beta-Benzyl N-benzyloxycarbonyl-L-Aspartyl-D-alanine

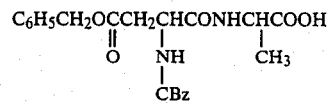

D-Alanine (5.0 g., 56.1 mmole) was dissolved in 100 ml. of N,N-dimethylformamide (DMF) and to the solution was added dropwise at room temperature 6.74 g. (62.4 mmole) of trimethylchlorosilane. In a separate flask was placed beta-benzyl N-benzyloxycarbonyl-L-aspartate (18.0 g., 50.4 mmole), triethylamine (12.35 g., 122 mmole) and 110 ml. each of DMF and tetrahydrofuran and the resulting solution cooled to −15° C. To the solution was added ethyl chloroformate (5.95 g., 55.1 mmole) and the resulting mixture stirred for ten minutes at −10° C. To this was then added dropwise the DMF solution of silylated D-alanine prepared above while maintaining the mixture at −5° to −10° C. The mixture was stirred at −5° C. for one hour, 0.2N hydrochloric acid added until the mixture was acidic and the resulting mixture extracted with chloroform. The chloroform extracts were combined and washed several times with dilute hydrochloric acid to remove remaining DMF. The solvent was evaporated in vacuo to provide the title compound as a colorless oil. The oil was triturated with ethyl ether (100 ml.) to obtain colorless crystals after three hours. The slurry was filtered, washed with ether, then hexane and air dried to afford 9.18 g., M.P. 158°–159° C. Upon work-up of the mother liquor an additional 4.45 g. of product was obtained, M.P. 157°–158° C. (Total yield, 63%). Thin-layer chromatography (silica gel plates) employing a 9:9:2 (by volume) ethyl acetate/hexane/acetic acid solvent system showed product and a trace amount of beta-benzyl N-benzyloxycarbonyl-L-aspartate.

EXAMPLE 2

Beta-Methyl-N-benzyloxycarbonyl-L-aspartyl-D-alanine

A suspension of 69 g. (0.78 mole) D-alanine in 200 ml. of DMF was cooled to 10° C., 92 g. (0.85 mole) of trimethylchlorosilane was added in portions and the resulting mixture stirred at 25° C. for one hour.

In a separate flask was placed a solution of 158 g. (0.86 mole) of beta-methyl-L aspartic acid hydrochloride in one liter of water. To this was added 34.5 g. (0.86 mole) of sodium hydroxide followed by 80 g. of sodium bicarbonate and the resulting mixture stirred vigorously. After cooling to 5°–10° C. 161 g. (0.94 mole) of benzyloxycarbonyl chloride was added in portions and stirring continued for two hours at this temperature. The reaction mixture was washed with 100 ml. of ethyl acetate, acidified by addition of 80 ml. of concentrated hydrochloric acid and extracted with ethyl acetate (2×450 ml.). The extract (900 ml.) was found to contain 218 g. (0.78 mole, 90% yield) of beta-methyl-N-benzyloxycarbonyl-L-aspartate. It was used in the next step without further purification.

The ethyl acetate extract was cooled to −20° C., 165 g. (1.63 mole) of triethylamine and 84 g. (0.78 mole) ethyl chloroformate were added. The solution was stirred at −15° to −20° C. for 30 minutes then treated quickly with the DMF solution of D-alanine trimethylsilylester prepared above and the resulting mixture was allowed to warm to ambient temperature over one hour with stirring. The reaction mixture was washed with water (3×500 ml.), the organic layer dried over sodium sulfate and evaporated in vacuo to a 200 ml. volume. Hexane, 400 ml., was added, the mixture granulated at 5° C. and filtered to afford 218 g. (80%) of the title compound as a white powder.

Replacement of the D-alanine employed in the procedures of Examples 1 and 2 with DL-alanine, D-2-aminobutyric acid, D-valine, D-norvaline or racemates of the latter four amino acids similarly provides the corresponding diblocked L-aspartyl-D- (or DL)-amino acid dipeptides of the formula

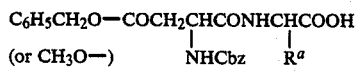

where Cbz is $COOCH_2C_6H_5$ and $R^a$ is $CH_3$, $C_2H_5$, $(CH_3)_2CH$ or $CH_3CH_2CH_2$.

EXAMPLE 3

L-Aspartyl-D-alanine N-(cis,trans-2,6-dimethylcyclohexyl)amide

A. To a solution of 218 g. (0.62 mole) of beta-methyl-N-benzyloxycarbonyl-L-aspartyl-D-alanine in one liter of ethyl acetate was added 69 g. (0.68 mole) triethylamine, the mixture was cooled to −20° C. and 67 g. (0.62 mole) of ethyl chloroformate was added. The resulting solution was stirred for 30 minutes at −15° to −20° C., then treated with 86 g. (0.68 mole) of cis,trans-2,6-dimethylcyclohexylamine and stirring continued for 30 minutes. After allowing to warm to room temperature the mixture was washed twice with 500 ml. portions of water containing 15 ml. of concentrated hydrochloric acid, twice with 500 ml. of 5% aqueous sodium bicarbonate, then water. The organic layer was dried ($Na_2SO_4$), concentrated in vacuo to about 200 ml. and 400 ml. of hexane was added whereupon beta-methyl-N-benzyloxycarbonyl-L-aspartyl-D-alanine N-(cis,trans-2,6-dimethylcyclohexyl)amide precipitated, 229 g. (80%), M.P. 213°-214° C.

B. The product obtained in Part A, above, 229 g. (0.50 mole) was dissolved in 500 ml. of methanol and a solution of 24 g. (0.60 mole) of sodium hydroxide in 500 ml. of water was added. The mixture was stirred at 30° C. for one hour, neutralized to about pH 7 with dilute hydrochloric acid and charged into an autoclave. Two grams of 5% palladium/carbon catalyst was added and the mixture hydrogenated at 25° C., 3.5 kg./cm.$^2$ (50 psi) for one hour. The catalyst was removed by filtration, the filtrate evaporated in vacuo to 200 ml., the concentrate acidified to pH 5.2 with concentrated hydrochloric acid, then granulated at 5° C. for one hour. The resulting precipitate was collected by filtration, the wet cake dissolved in a mixture of 200 ml. of water and 50 ml. of concentrated hydrochloric acid, carbon treated, filtered and the filtrate adjusted to pH 5.2 with 50% (w/w) sodium hydroxide solution. After granulation at 5° C., filtering, washing with cold water and drying, 132 g. (85% step yield) of colorless product was obtained, M.P. 216°-217° C. The overall yield was 68%.

Sweetness potency: 600 x sucrose.

By employing the appropriate beta-methyl-N-Cbz-L-aspartyl-D (or DL)-amino acid dipeptide in the above procedures the corresponding dipeptide amides of formula (I), wherein R is c,t-2,6-dimethylcyclohexyl and $R_a$ is $CH_3$, $C_2H_5$, $(CH_3)_2CH$ or $CH_3CH_2CH_2$, are obtained in like manner.

EXAMPLE 4

L-Aspartyl-D-alanine N-(2-methycyclohexyl)amide (mixture of cis,trans-isomers)

A. Under anhydrous conditions, to a mixture of 1.28 g. (3 mmole) of beta-benzyl N-benzyloxycarbonyl-L-aspartyl-D-alanine, 40 ml. of tetrahydrofuran and 0.29 ml. (3.6 mmole) pyridine cooled to −20° C. was added dropwise 0.29 ml. (3 mmole) of ethyl chloroformate. The resulting slurry was stirred at −15° C. for ten minutes then 0.79 ml. (6 mmole) of a mixture of the cis and trans-isomers of 2-methylcyclohexylamine was added dropwise over a few minutes. The reaction mixture was allowed to warm to room temperature, diluted with water and extracted with chloroform. The organic layer was washed with dilute hydrochloric acid, water, sodium bicarbonate solution, water again and finally with saturated aqueous sodium chloride. The washed extract was dried over sodium sulfate and evaporated to dryness to afford a colorless solid. The solid was triturated with ethyl ether, stirred, filtered and dried to yield 1.3 g. (83%) of betabenzyl N-benzyloxycarbonyl-L-aspartyl-D-alanine-N-(2-methylcyclohexyl)amine which showed only one spot ($R_f$ 0.65) on TLC (ethyl acetate/hexane/acetic acid 10:9:1, by volume).

B. To a solution of the product obtained in Part A, above, 1.05 g. (2 mmole) in 100 ml. of methanol was added 0.5 g. of 5% palladium-on-carbon catalyst and the mixture was hydrogenated in a Parr shaker at room temperature, 3.5 kg./cm. (50 psi) for 30 minutes, after which uptake of hydrogen ceased. The reaction mixture was filtered, the filtrate evaporated in vacuo to afford 610 mg. of the desired product as an off-white solid which is a mixture of cis- and transisomers; M.P. 206°-209° C.

Sweetness potency: 250 x sucrose.

EXAMPLE 5

L-Aspartyl-D-alanine N-(dicyclopropylcarbinyl)amide:

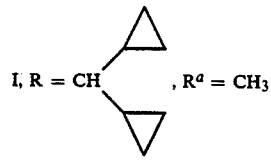

A. Dicyclopropylcarbinylamine

In a 500 ml. round bottom flask was placed 41.7 g. (0.60 mole) hydroxylamine hydrochloride and 80 ml. water. With stirring, 44 ml. of 10M sodium hydroxide solution and 44.4 g. (0.40 mole) dicyclopropyl ketone were added. The mixture was stirred at reflux for three hours. After cooling, 60 ml. methylene chloride was added and the mixture stirred until all oxime had dissolved. The methylene chloride layer was separated and dried over anhydrous magnesium sulfate. The solvent was removed by evaporation at reduced pressure and the residue recrystallized from 55 ml. hexane, yielding 40.0 g. dicyclopropylketoxime, M.P. 69°-72° C.

In a 500 ml., three-necked round bottom flask was placed 18.8 g. (0.15 mole) dicyclopropylketoxime and 150 ml. anhydrous ethanol. With efficient stirring 19.2 g. (0.83 mole) sodium spheres was added in portions as rapidly as possible, maintaining reflux throughout the addition. Following dissolution of the sodium, the reaction was cooled to 60° C. and 60 ml. water was added. After cooling, 78 ml. concentrated hydrochloric acid was added dropwise with stirring. Ethanol was distilled at reduced pressure and 50 ml. water added to dissolve salts. The mixture was adjusted to pH 13 with 10 M sodium hydroxide solution and extracted with three 40 ml. portions of methylene chloride. The extracts were combined, dried over anhydrous magnesium sulfate, filtered and evaporated at reduced pressure. The residual amine was distilled at 88°–90° C./95 mm Hg, yielding 11.0 g. of the desired product.

B.

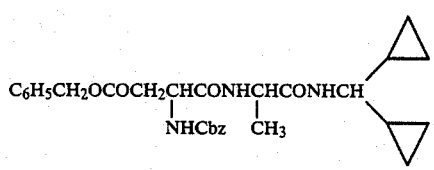

To a 250 ml. three-necked flask fitted with a stopper, thermometer, drying tube and magnetic stirring bar was added 4.28 g. (0.010 mole) of beta-benzyl-N-benzyloxycarbonyl-L-aspartyl-D-alanine, 75 ml. tetrahydrofuran and 1.53 ml. (0.011 mole) triethylamine. The mixture was cooled to −10° C., 1.05 ml. (0.011 mole) ethyl chloroformate was added, stirred for 20 minutes, cooled to −35° C. and 1.11 g. (0.010 mole) of dicyclopropylcarbinylamine added. The reaction mixture was allowed to warm slowly to room temperature and stirred overnight. The mixture was poured into 150 ml. water, extracted with 250 ml. of ethyl acetate and the organic phase washed with 5% aqueous sodium bicarbonate (2×75 ml.), 3 M hydrochloric acid (2×75 ml.), brine (1×100 ml.) and dried over anhydrous magnesium sulfate. The dried extract was evaporated to dryness in vacuo to provide a colorless solid which was recrystallized from 75 ml. of boiling ethyl acetate to obtain 3.78 g. (72%) of diblocked amide, M.P. 164°–165° C. Thin-layer chromatography (TLC) on silica gel, eluting with 1:1 ethyl acetate/hexane gave a single spot, $R_f$ 0.40 with vanillin spray reagent. An additional 0.65 g. was recovered from the mother liquors.

C. To a slurry of 2.58 g. (4.9 mmole) of the product obtained in Part B in 250 ml. of methanol was added 0.60 g. of 5% palladium-on-carbon catalyst (50% wet) and the mixture hyirogenated for one hour at an initial pressure of 71 psi (5.0 kg./cm. ). The catalyst was removed by filtration and the methanol evaporated at reduced pressure to afford 1.47 g. (100%) of colorless product, M.P. 190°–191° C. TLC in 4:1:1 butanol/water/acetic acid (v/v) and spraying with ninhydrin gave a single spot, $R_f$ 0.36.

Sweetness, 1200 times sucrose.

Starting with the appropriate beta-benzyl-N-Cbz-L-aspartyl-D-alanine in each case the remaining compounds of formula (I) wherein R is CH)2 and Ra is C H5, (CH)2CH or n-C3H7 are obtained in like manner.

EXAMPLE 6

L-Aspartyl-D-alanine N-(dl-t-butylcyclopropylcarbinyl)amide:

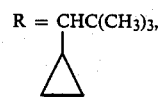

A. t-Butylcyclopropylcarbinylamine

To 0.5 mole each of cyclopropanecarbonyl chloride and cuprous chloride in 500 ml. of dry ethyl ether was added dropwise under a nitrogen atmosphere 238 ml. (0.5 mole) of 2.1 M t-butylmagnesium chloride in the same solvent at −10° C. The reaction mixture was poured into a mixture of 250 ml. of 3 M hydrochloric acid and 700 g. of ice, the organic layer separated, washed with water, sodium bicarbonate solution, brine and dried over anhydrous magnesium sulfate. The ether was evaporated at reduced pressure and the residue distilled at atmospheric pressure to provide 45 g. (72%) of t-butylcyclopropylketone, B.P. 145°–153° C.

The 45 g. (0.36 mole) of ketone was reacted with hydroxylamine hydrochloride and sodium acetate in 1:1 ethanol/water by the method of Example 5, Part A. After heating at reflux overnight the reaction mixture was cooled and the precipitated oxime collected and washed with cold ethanol to obtain 23.5 g. of tbutylcyclopropylketoxime. An additional 7.7 g. was obtained from the mother liquors. The combined crops were recrystallized from 1:1 ethanol/water to provide 25.2 g. (50%) of oxime, M.P. 113.5°–114° C.

To a solution of 5.0 g. (0.035 mole) of oxime in 80 ml. of ethanol was added 8.04 g. (0.35 mole) of sodium and the reaction carried out and product isolated as described in Example 5, Part A, to afford 3.31 g. of crude dl-t-butylcyclopropylcarb-inylamine. This was distilled at atmospheric pressure to yield 2.01 g. (45%) of product boiling at 153°–155° C.

B.

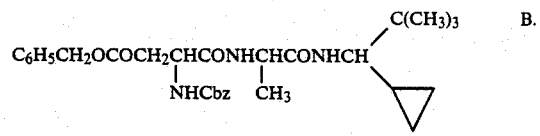

The procedure of Example 5, Part B was repeated employing 0.76 g. (6.6 mmole) of dl-t-butylcyclopropylcarbinylamine in place of dicyclopropylcarbinylamine and proportional amounts of the other reagents. Evaporation of the ethyl acetate extracts in vacuo gave 3.12 g. (97%) of solid diblocked dipeptide amide. This was purified by column chromatography on a 2.5×30 cm. column, eluting with 1:1 ethyl acetate/hexane. After evaporation of the fractions containing the desired product (as determined by TLC), 2.33 g. (72%) of colorless solid was obtained, M.P. 118°–120° C.

C. The purified product from Part B, 2.33 g., was hydrogenated over a palladium-on-carbon catalyst as described in Example 5, Part C, to afford 1.28 g. (95%) of the desired dipeptide amide, M.P. 180°–182° C. (dec.), silica gel TLC (4:1:1 butanol/water/acetic acid): one spot, $R_f$ 0.43.

Sweetness, 1200 x sucrose.

The remaining compounds of formula (I) wherein R

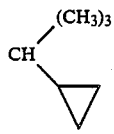

and R$^a$ is ethyl, isopropyl or n-propyl are similarly obtained from the appropriate diblocked dipeptide.

EXAMPLE 7

L-Aspartyl-D-alanine
N-(2,2,5,5-tetramethylcyclopent-1-yl)amide:

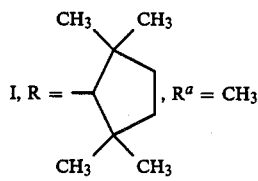

A 2,2,5,5-Tetramethylcyclopentylamine

A mixture of 21.0 g. (0.15 mole) of 2,2,5,5tetramethylcyclopentanone (B.P. 63°–68° C. at 40 mm.), 40.5 g. (0.8 mole) formamide and 4 ml. of formic acid was heated at 160°–190° C. for 20 hours with addition of 10 ml. increments of formic acid whenever solid ammonium carbonate deposits formed in the condenser. During this time water was removed from the reaction mixture by means of a variable take-off fractionating head. The mixture was cooled, extracted with ethyl acetate and extracts evaporated to obtain a dark residual oil. This was mixed with 60 ml. of 6 N hydrochloric acid and the mixture heated at reflux for three hours. The resulting solution was adjusted to pH 13 with sodium hydroxide, extracted with ethyl ether, the extracts washed with water, brine, dried (magnesium sulfate) and evaporated to dryness to yield 4.9 g. of crude amine which was distilled to obtain 1 g. of the desired tetramethylamine, B.P. 66°–69° (30 mm.).

B.

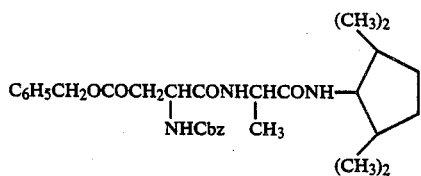

By employing 856 mg (6 1 mmole) of 2,2,5,5tetramethylcyclopentylamine and proportional amounts of the other reagents employed in Example 5, Part B, the diblocked dipeptide amide of the above formula was obtained by the procedure of that example. R$_f$, 0.36 by silica gel TLC (2:3 ethyl acetate/hexane) It was purified by column chromatography on silica gel, eluting with ethyl acetate/hexane (2:3) to obtain 495 mg. after evaporation of product-containing fractions.

C. The purified diblocked dipeptide amide provided in Part B, 495 mg., was dissolved in 75 ml of methanol and hydrogenated over 300 mg. of 5% palladium-on-carbon catalyst as described in Example 5, Part C After evaporation of solvent, 185 mg. of the desired dipeptide amide was obtained as an off-white solid, M.P. 136°–140° C.

Sweetness, 800 x sucrose.

The compounds of formula (I) wherein R is 2,2,5,5-tetramethylcyclopentyl and R$^a$is ethyl, isopropyl or n-propyl are obtained in like manner from the appropriate diblocked dipeptide by the above procedure.

EXAMPLE 8

3-Amino-2,2,4,4-tetramethyltetrahydrofuran

A. 2,2,4,4-Tetramethyltetrahydrofuran-3-one

4-Bromo-1-hydroxy-2,2,4-trimethylpentan-3-one (prepared as described in Example 13, Parts A and B) 25 g. (0.1 mole) was dissolved in 160 ml. of ethanol and a solution of 8 g. (0.2 mole) sodium hydroxide in 80 ml. of water was added. The resulting mixture was stirred at room temperature for 30 minutes, diluted with water, extracted with ethyl ether, the extracts washed with water, brine and dried over anhydrous magnesium sulfate. The solvent was evaporated to afford 17.7 g. of 2,2,4-trimethylpentan-1,4-diol as a colorless liquid which was identified by $^1$H-NMR. The diol was dissolved in 50 ml. of chloroform, 1.5 ml. of concentrated sulfuric acid added dropwise. The mixture was heated at reflux for 3 hours, while distilling water/chloroform azeotrope from the mixture. After standing overnight at room temperature the reaction mixture wa washed with water, the organic layer dried (MgSO$_4$) and solvent evaporated in vacuo to provide 13.9 g. of colorless liquid. Distillation afforded 8.3 g. of the desired product, B.P. 70°–72° (50 mm.), overall yield 58%.

B. The ketone obtained in Part A, 8.0 g. (0.056 mole), hydroxylamine hydrochloride, 8.0 g. (0.113 mole) and sodium acetate, 2.3 g. (0.113 mole), were combined with 85 ml. of ethanol and the mixture heated at reflux for 48 hours. The resulting mixture was diluted with water, extracted with ethyl ether, the extracts washed with water, dried and evaporated to yield 9.0 g. of a mixture of syn- and anti-oximes, identified by its $^1$H-NMR spectrum.

The oxime obtained above, 1.3 g. (8.28 mmole) was dissolved in 70 ml. of dry ethanol, 1.9 g. of sodium metal added and the mixture warmed to reflux and held at this temperature for 15 minutes. Heating was continued for two hours with addition of two more increments (1.9 g. each) of sodium. The reaction mixture was then diluted cautiously with water, extracted with ethyl ether. The ether layer extracted with dilute hydrochloric acid, the aqueous phase made alkaline with sodium hydroxide and re-extracted with ether. The extracts were dried (MgSO$_4$) and evaporated to dryness and the residue distilled to obtain the desired amine, B.P. 68°–69° C. (15 mm). After further purification by precipitation of the hydrochloride salt from ethyl ether-methanol, basifying the salt and extracting again with ether 0.87 g. of amine of 93% purity by gas chromatography (OV-1 column) was obtained.

EXAMPLE 9

By employing the appropriate amine of formula RNH$_2$ in the procedure of Example 4 the following amides of L-aspartyl-D-alanine were provided in like manner.

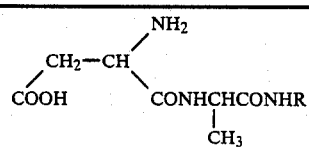
| R* | Diblocked Dipeptide Amide $R_f$ | Diblocked Dipeptide Amide % Yield | M.P., °C. | Dipeptide Amide (I) % Yield | Sweetness × sucrose |
|---|---|---|---|---|---|
| 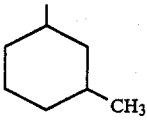 | 0.54<br>0.63[a] | 99 | 194–197° Dec. | 83 | 15 |
| c + t <br>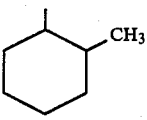 | 0.57[b] | 56 | 213–215° | — | 220 |
| trans <br> | 0.57[a] | 33 | 180–182° Dec. | 77 | 250 |
| trans <br> | 0.50[a] | 90 | 224–225° Dec. | 92 | 600 |
| trans, trans <br> | 0.46[c] | 50 | 185–187° | 59 | 200 |
| c, t + t, t <br>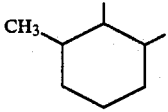 | 0.55[a] | 42 | 198–201° Dec. | 74 | 200 |
| c, t + t, t <br>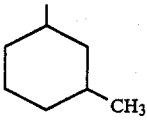 | 0.54[a] | — | 145–148° | 74 | 500 |
| trans <br>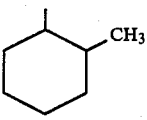 | 0.40[c]<br>0.54[c] | 100 | 148–150° Dec. | 75 | 450 |
| c + t <br> | 0.73[c] | 100 | 136–138° Dec. | 63 | 300 |

-continued $$\underset{COOH}{CH_2}-\underset{\underset{CONHCHCONHR}{|}}{\overset{\overset{NH_2}{|}}{CH}}$$
$$\phantom{CH_2CHCONHCHCO}CH_3$$

| R* | Diblocked Dipeptide Amide | | Dipeptide Amide (I) | | Sweetness × sucrose |
|---|---|---|---|---|---|
| | $R_f$ | % Yield | M.P., °C. | % Yield | |
| c, t + t, t ![(CH3)2CH-cyclohexyl-CH(CH3)2] | 0.34$^c$ | — | 143–145° | 65 | 150 |
| c, t + t, t ![cyclohexyl-C(CH3)2] | 0.31$^c$ | 100 | 199–202° | 44 | 250 |
| dl ![CH3-cyclohexyl-C(CH3)2] | 0.36$^c$ | 69 | 199–206° | 100 | 400 |
| c + t ![(CH3)2C-cyclohexyl-C(CH3)2] | 0.33$^c$ | 97 | 105–112° | 42 | 300 |
| ![(CH3)2C-bicyclic-CH3] | 0.56$^c$ | 95 | | 91 | 320 |
| l ![(CH3)2C-bicyclic-CH3] | 0.55$^c$ | 95 | — | 91 | 200 |
| dl ![cyclopentyl-CH3] | 0.44$^a$ | 100 | 185–186° Dec. | 86 | 220 |
| trans ![cyclopentyl-C2H5] | 0.75$^a$ | 96 | 89–93° Dec. | 82 | 250 |
| trans ![cyclopentyl-CH(CH3)2] | 0.38$^c$ | 88 | 206–208° Dec. | 89 | 625 |
| trans | | | | | |

-continued

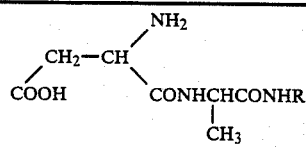

| R* | Diblocked Dipeptide Amide | | Dipeptide Amide (I) | | |
|---|---|---|---|---|---|
| | $R_f$ | % Yield | M.P., °C. | % Yield | Sweetness × sucrose |
| 2,4-dimethylcyclopentyl, mixed isomers | — | 93 | 175–177° Dec. | 59 | 520 |
| 2,2,3-trimethyl-tetrahydrofuran-5-yl, dl | $0.2^c$ | 94 | 95–99° | 100 | 350 |
| 1-tert-butylcyclopentyl, dl | $0.4^c$ | 95 | 186–188° Dec. | 73 | 140 |
| 1,3-diisopropyl-methine, (CH₃)₂CH—CH—CH(CH₃)₂ | $0.54^a$ | 100 | 179–181° Dec. | 81 | 250 |
| (CH₃)₃C—CH—CH₃ | $0.66^a$ | 63 | 180–183° Dec. | 48 | 180 |
| (CH₃)₃C—CH—CH₃, dl | $0.6^a$ | 98 | 182–184° Dec. [alpha]$_D$ + 20.3 (C = 1, CH₃OH) | 61 | 0 |
| (CH₃)₃C—CH—CH₃, l | — | 96 | 183–185° Dec. [alpha]$_D$ + 29.7 (C = 1, CH₃OH) | 52 | 375 |
| (CH₃)₃C—CH—CH₂CH₃, d | $0.54^a$ | 100+ (crude) | 134–137° Dec. | 72 | 180 |
| cyclopropyl-CH—CH₃, dl | $0.72^a$ | 89 | 193–197° Dec. | 87 | 110 |
| (CH₃)₃C—CH—CH(CH₃)₂, dl | — | 79 | 110–115° Dec. | 54 | 125 |

In like manner the corresponding compounds of the formula

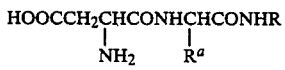

are obtained from the appropriate diblocked dipeptide,

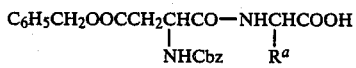

where $R^a$ is ethyl, isopropyl or n-propyl and R has the values assigned above.

EXAMPLE 10

L-Aspartyl-DL-alanine N-(dicyclobutylcarbinyl)amide:

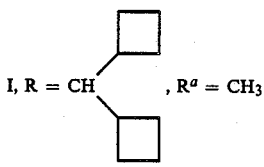

A.

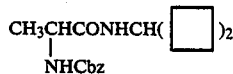

To a mixture of 3.0 g. (0.0135 mole) of N-benzyloxycarbonyl-DL-alanine and 1.27 g. (0.016 mole) pyridine is added at −10° C. 1.45 g. (0.0135 mole) ethyl chloroformate. The mixture is stirred for 15 minutes, cooled to −15° and 3.75 g. (0.027 mole) of dicyclobutylcarbinylamine is added. The reaction mixture is allowed to warm to room temperature, dissolved in ethyl acetate and the solution washed with dilute hydrochloride acid, sodium bicarbonate solution, brine and the washed extracts dried ($Na_2SO_4$) The solvent is evaporated to provide the desired N-Cbz-alanine-N-(dicyclobutylcarbinyl)amide.

B. Diblocked dipeptide amide

A solution of 3.54 g. (0.01 mole) N-Cbz-alanine-N-(dicyclobutylcarbinyl)amide in 100 ml. of methanol is hydrogenated over 1 g. of 5% palladium-on-carbon, the catalyst removed by filtration and the solvent evaporated to provide N-(dicyclobutylcarbinyl)-DL-alanine amide.

In a separate flask containing 4.46 g. (0.0125 mole) of beta-benzyl N-benzyloxycarbonyl-L-aspartate in 100 ml. of tetrahydrofuran containing 1.2 g. (0.015 mole) pyridine is added 1.35 g. (0.0125 mole) ethyl chloroformate while maintaining the mixture at −30° C. The resulting mixture is stirred for 10 minutes at this temperature. To this is then added the N-(dicyclobutylcarbinyl)-DL-alanine amide, obtained above, as a solution in tetrahydrofuran (100 ml.) and N,N-dimethylformamide (10 ml.). The reaction mixture is stirred at −20° C. for 30 minutes then allowed to warm to room temperature, extracted with ethyl acetate, washed successively with water, sodium bicarbonate solution, dilute hydrochloric acid, and water again. After drying the washed extracts over anhydrous sodium sulfate, the solvent is evaporated to provide beta-benzyl N-benzyloxycarbonyl-L-aspartyl-DL-alanine N-(dicyclobutylcarbinyl)amide suitable for use in the next step without further purification.

C. To a solution of 1.5 g. of the diblocked dipeptide amide, obtained in Part B, in 100 ml. of methanol is added 1 g. of 5% palladium-on-carbon and the mixture hydrogenated at 3-4 atmospheres pressure. The catalyst is recovered by filtration and the filtrate evaporated at reduced pressure to provide the title compound.

D. When the above procedure of Part A is repeated with N-benzyloxycarbonyl-D-alanine or the N-benzyloxycarbonyl derivatives of D-valine, D-2-aminobutyric acid or D-norvaline and the appropriate amine of formula $RNH_2$ and the product thus obtained hydrogenated by the procedure of the first paragraph of Part B, above, D-amino acid amides of formula $R^aCH(NH_2)CONHR$ are obtained where $R^a$ is methyl, ethyl, isopropyl or n-propyl and R is as defined below.

By carrying each of these D-amino acid amides through the procedure of the remaining portion of Part B and Part C, above, the corresponding L-aspartyl-D-amino acid dipeptide amides of formula (I) are obtained in like manner.

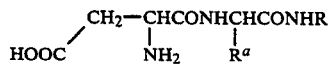

R dl-fenchyl
diisopropylcarbinyl
d-methyl-t-butylcarbinyl
d-ethyl-t-butylcarbinyl
di-t-butylcarbinyl
cyclopropyl-t-butylcarbinyl
cyclopentyl-t-butylcarbinyl
dicyclopropylcarbinyl
l-fenchyl
2,2,4,4-tetramethylcyclobutyl
2-methylcyclopentyl
2-ethylcyclopentyl
2-isopropylcyclopentyl
2,5-dimethylcyclopentyl
2,2,5,5-tetramethylcyclopentyl
2-ethylcyclohexyl
2-isopropylcyclohexyl
2-t-butylcyclohexyl
2-ethyl-6-methylcyclohexyl
2,2-dimethylcyclohexyl
2,6-dimethylcyclohexyl
2,2,6-trimethylcyclohexyl
2,2,6,6-tetramethylcyclohexyl
2,2,4,4-tetramethyl-3-oxocyclobutyl
2,2,4,4-tetramethyl-3-hydroxycyclobutyl
2,2,4,4-tetramethyltetrahydrofuran-3-yl

EXAMPLE 11

Employing the methods described above the following L-aspartyl-D-amino acid amides and L-aspartyl-DL-amino acid amides are prepared in like manner.

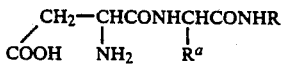

where $R^a$ is $CH_3$, $C_2H_5$, $n-C_3H_7$ or $i-C_3H_7$.

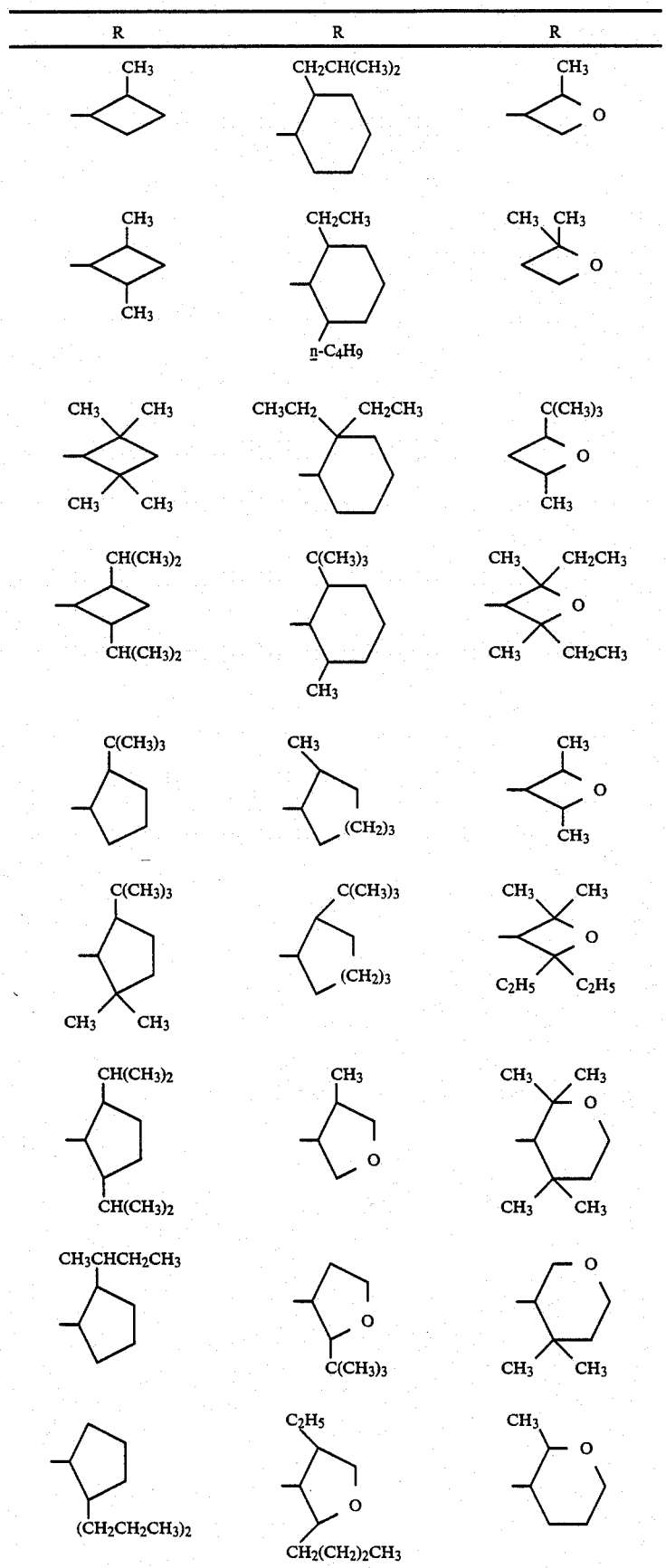

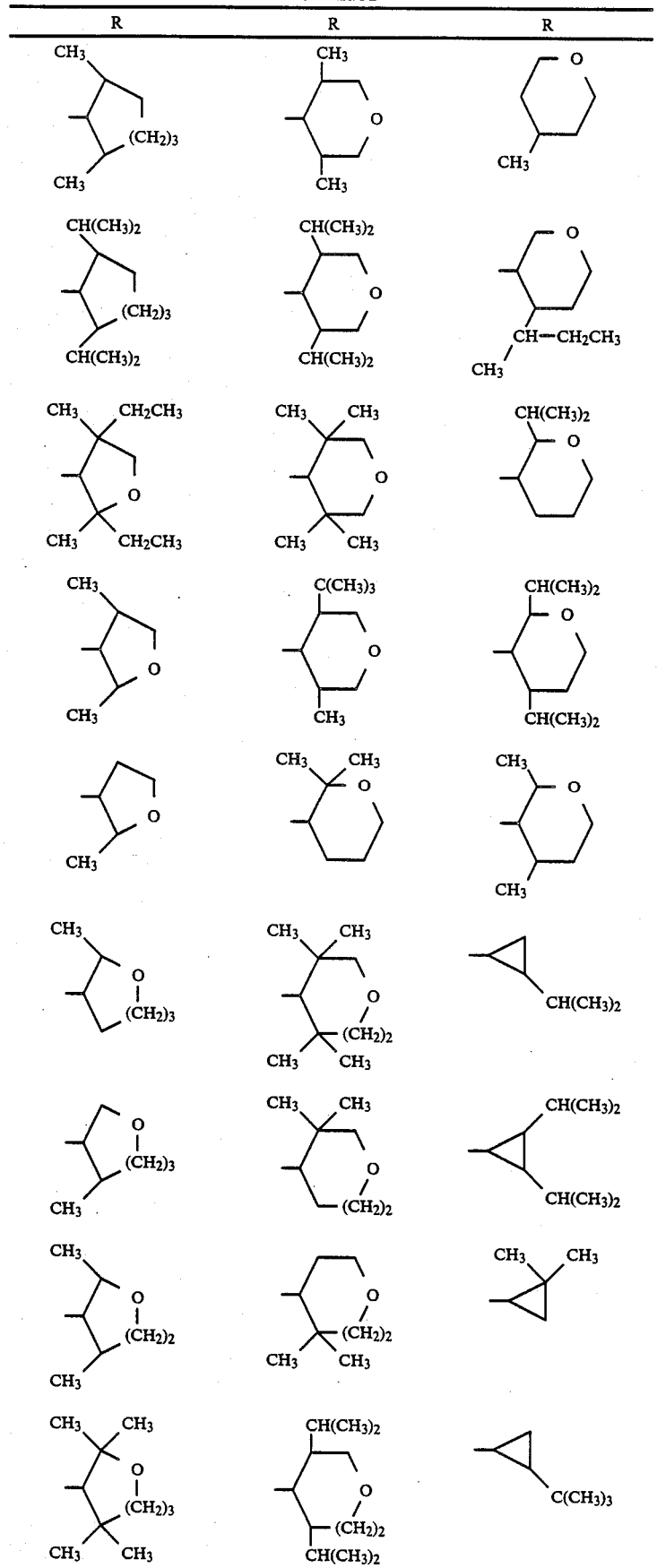

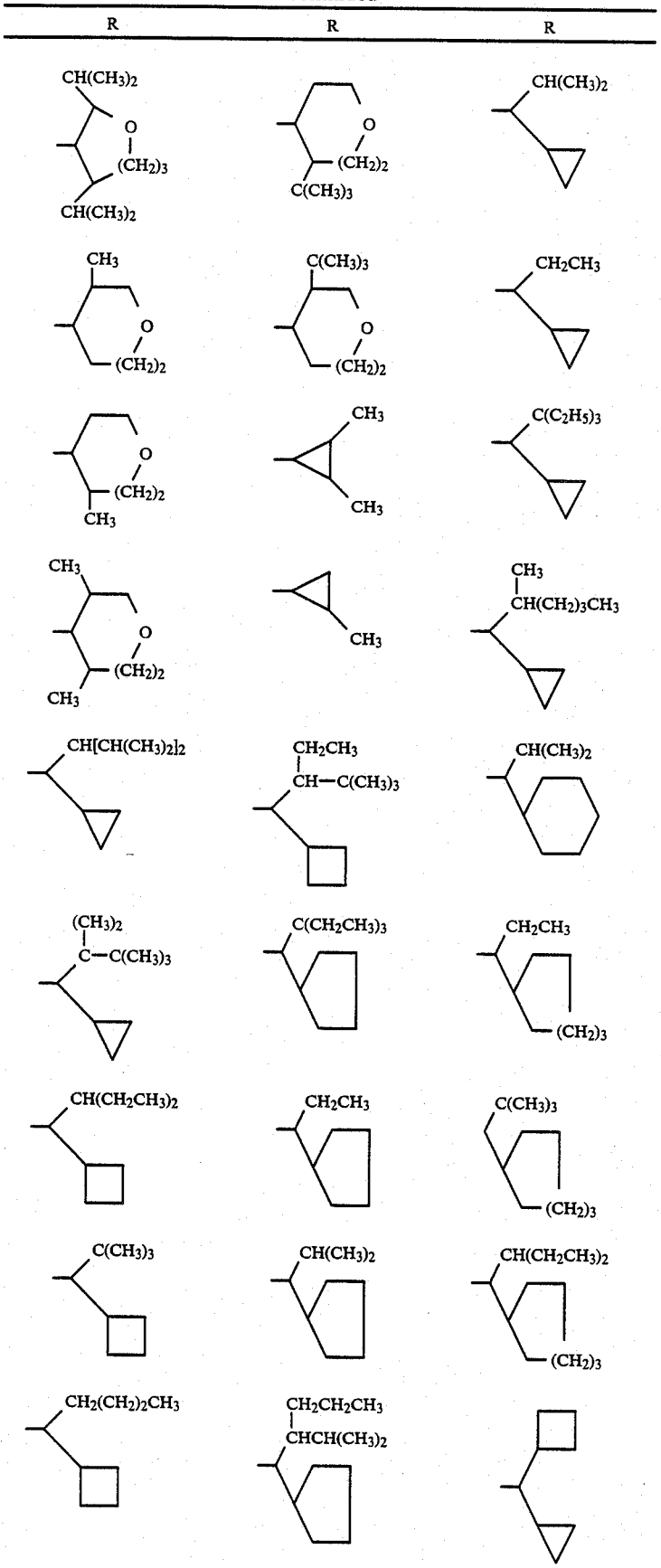

-continued
| R | R | R |
|---|---|---|
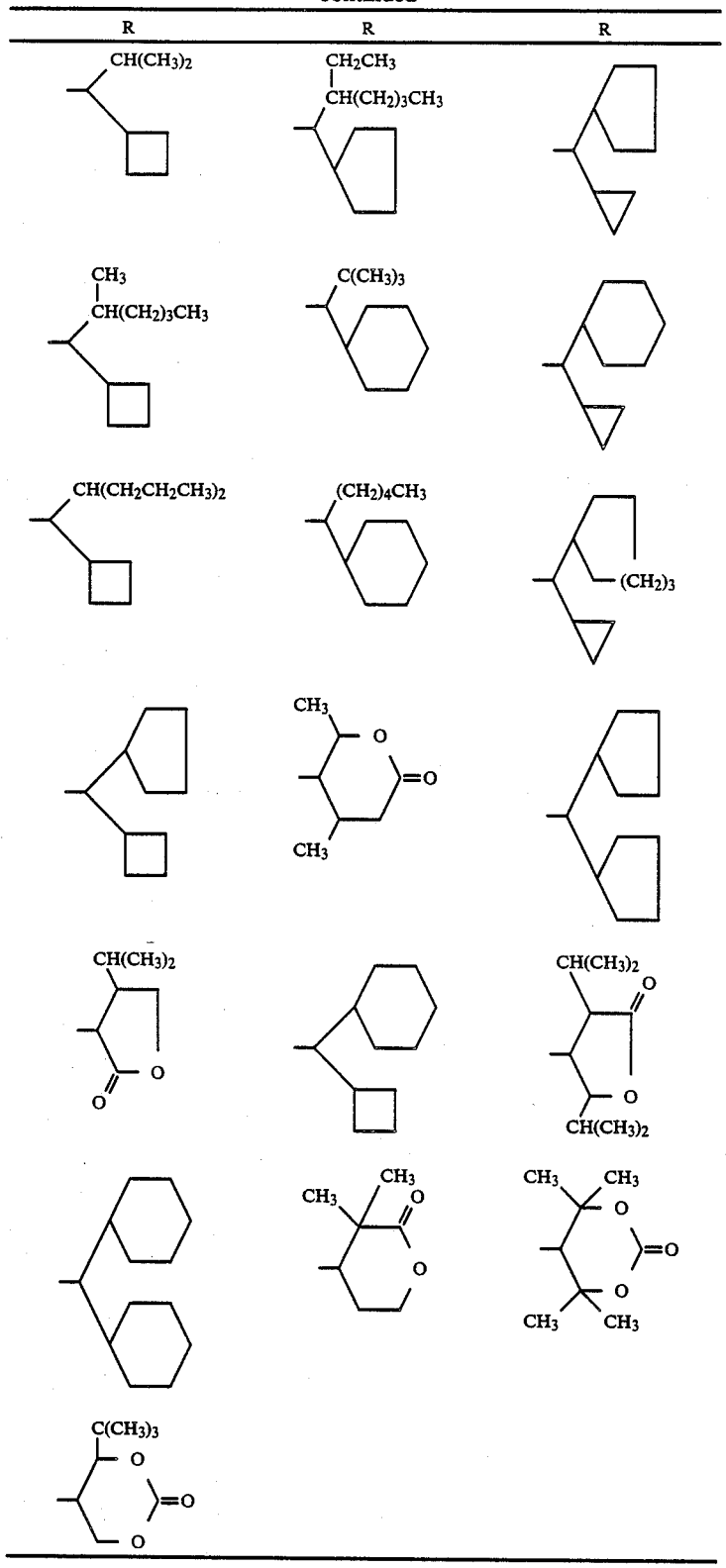

EXAMPLE 12

L-Aspartyl-D-alanine-N-(3,5-dimethyl-tetrahydrothiopyran-4-yl)amide:

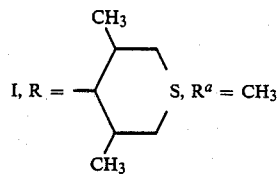

mixture of cis/trans and trans/trans isomers

A. 3,5-Dimethyltetrahydrothiopyran-4-one

A mixture of 2 g. of sodium acetate and 25 ml. of ethanol was saturated with hydrogen sulfide gas. To this was added 7.0 g. (0.063 mole) diisopropenylketone while cooling in an ice bath until the reaction was no longer exothermic. The mixture was stirred at room temperature while passing hydrogen sulfide through the mixture for four hours then allowed to stand overnight. The ethanol and excess $H_2S$ were evaporated in vacuo and the residue taken up in ethyl ether, washed in turn with water, potassium carbonate solution, dilute hydrochloric acid, and water again. The ether extracts were dried ($Na_2SO_4$) and evaporated to provide 6.8 g. of oil. This was distilled in vacuo through a 10 cm. Vigreaux column to provide 1.67 g. of product, B.P. 83°–86° C./9 mm. which was used in the next step without further purification.

B. 4-Oximino-3,5-dimethyltetrahydrothiopyran

A mixture of 1.67 g. (0.011 mole) of the cyclic ketone obtained in Part A, 1.6 g. (0.023 mole) hydroxylamine hydrochloride and 1.9 g. (0.023 mole) sodium acetate in 30 ml. of water and 10 ml. of ethanol were heated at reflux for three hours, cooled and the precipitate recovered by filtration. After recrystallization from 1:1 methanol-water 1.5 g. of oxime was obtained as a white solid, M.P. 60°–85° C. which is a mixture of isomers of suitable purity for use in the next step.

C. trans/trans and cis/trans-4-Amino-3,5-dimethyltetrahydrothiopyran

To a solution of 1.45 g. (0.009 mole) of the oxime obtained in Part B in 15 ml. of ethanol was added in portions 5 g. of sodium shot followed by an additional 25 ml. of ethanol and the resulting mixture heated at reflux for about 30 minutes. The reaction mixture was diluted with water, extracted with ethyl ether, and the extracts washed with water. The ether layer was extracted with dilute hydrochloric acid and the aqueous layer washed with fresh ether. The aqueous layer was made alkaline by addition of sodium hydroxide solution and extracted with ether again. The organic layer was dried ($MgSO_4$) and the ether evaporated to obtain 1.1 g. of residual colorless oil. Gas-liquid chromatography (OV-1 column with temperature programming from 80° to 100° C.) showed the product to contain two major components in a 60/40 ratio. $^1$NMR ($CDCl_3$) indicated the product to be a mixture of 4-amino-3-trans-5-trans-dimethyltetrahydrothiopyran and the corresponding 3-cis-5-trans-isomer.

D. N-tertiary-Butoxycarbonyl-D-alanine

To 7.0 ml. each of tetrahydrofuran and water was added 2.71 g. (11 mmole) N-(t-butoxycarbonyloxyimino)-2-phenylacetonitrile (BOC-ON, Aldrich Chemical Co.), 0.89 g. (10 mmole) D-alanine and 1.5 g. (15 mmole) triethylamine and the resulting two phase mixture stirred at room temperature. After about two hours the mixture became homogeneous and stirring was continued overnight. The mixture was diluted with water, washed with ethyl acetate and acidifed with dilute hydrochloric acid to pH 1.5. The acidifed solution was extracted with ethyl acetate, the extracts washed with water, saturated brine and dried over sodium sulfate. The solvent was evaporated at reduced pressure to afford 1.9 g. of product as a colorless oil suitable for use in the next step.

E. N-(3,5-Dimethyltetrahydrothiopyran-4-yl)-t-butoxycarbonyl-D-alanine amide

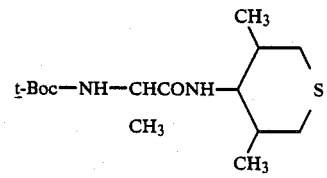

Under anhydrous conditions, to a mixture of 1.7 g. (8.9 mmole) of N-t-Boc-D-alanine obtained in Part D, 1.98 g. (19 mmole) triethylamine and 40 ml. of tetrahydrofuran, cooled to −10° C., was added dropwise 0.96 g. (8.9 mmole) ethyl chloroformate and the resulting mixture stirred at this temperature for 20 minutes. To this was added 1.1 g. (7.5 mmole) of the mixture of isomers of 4-amino-3,5-dimethyltetrahydrothiopyran obtained in Part C and the resulting mixture stirred at −10° C. for 10 minutes then allowed to warm to room temperature. The reaction mixture was diluted with water and extracted with ethyl acetate. The organic layer was washed with sodium bicarbonate solution, dilute hydrochloric acid, water, brine then dried (Na and the solvent evaporated at reduced pressure to obtain the product as a foam, 2.4 g. Thin-layer chromatography (TLC), silica gel plates, eluting with 1:1 ethyl acetate/hexane showed major spot for the product at $R_f$ 0.5 with trace impurities at $R_f$ 0.6 and 0.9.

F. N-(3,5-Dimethyltetrahydrothiopyran-4-yl)-D-alanine amide

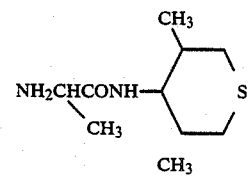

The t-Boc-amide obtained in Part E was dissolved in 15 ml. of ethanol and a mixture of 5 ml. of concentrated hydrochloric acid and 10 ml. of water were added. The resulting mixture was heated at reflux for 30 minutes, cooled and the ethanol removed by evaporation in vacuo. The aqueous residue was washed with ethyl ether, made alkaline with sodium hydroxide solution, extracted with ether and the extracts dried ($Na_2SO_4$). Evaporation of solvent provided 1.1 g. (67%) of colorless oil which crystallized upon standing.

G. Coupling of D-alanine amide with L-aspartic acid N-thiocarboxyanhydride

The D-alanine amide provided in Part F, 1.1 g. (5.1 mmole) was dissolved in 5 ml. of tetrahydrofuran and 5 ml. of water was added. The clear solution was cooled in ice and 0.89 g. (5.1 mmole) of L-aspartic acid N-thiocarboxyanhydride was added in one portion. To this was added as required, 0.5 M sodium hydroxide to maintain the mixture at pH 9. After stirring 30 minutes the reaction mixture was washed with ethyl ether then ethyl acetate and the washes discarded. The aqueous phase was acidified with dilute hydrochloric acid to pH 5.6 and evaporated to dryness at reduced pressure. The residue was taken up in hot methanol (100 ml.), filtered and the methanol evaporated. The residue was taken up again in hot methanol, filtered and the filtrate decolorized with activated carbon, filtered through diatomaceous earth and the filtrate evaporated to obtain 1.67 g. of crude product as a powder. The crude product was dissolved in hot water (11 ml.) and filtered, evaporated under a stream of nitrogen to 5 ml. and cooled in ice to precipitate the product as a gelatinous solid. The product was collected by filtration, sucked dry, washed with 2 ml. of cold water, 2 ml. of cold methanol and, finally with a mixture of 1 ml. methanol and 4 ml. of ethyl ether to afford a granular product which was dried in a vacuum oven at 50° C. to give 0.3 g. of the desired product.

Sweetness, 200 x sucrose.

Use of D-2-aminobutyric acid, D-valine or D-norvaline in place of D-alanine in the procedure of Part D above and reacting the N-t-butoxycarbonyl-Damino acids thus obtained in the procedures of Parts E, F and G, similarly provides the corresponding compounds of formula (I) wherein R is 3,5-dimethyltetrahydro-thiopyran-4-yl and $R^a$ is $C_2H_5$, $(CH_3)_2CH$, or $CH_3CH_2CH_2$, respectively.

EXAMPLE 13

3-Amino-2,2,4,4-tetramethyltetrahydrothiophene

A. 1-Hydroxy-2,2,4-trimethylpentan-3-one

To sodium methoxide prepared from 7.5 g. of sodium metal and 250 ml. of methanol was added 72.5 g. (2.4 moles) paraformaldehyde followed by 250 g. (2.2 moles) diisopropylketone and the resulting mixture heated at reflux for three hours. The reaction was quenched with water, neutralized with hydrochloric acid, extracted with ethyl ether, washed with water, brine and the solvent evaporated. The residual oil (90 g.) was distilled in vacuo to obtain 28 g. of the desired product boiling at 92°–98° C. at 16–20 mm. GLC on OV-1 column at 107° C., retention time 314 sec., 96% pure.

When the above procedure was repeated on the same scale but the reaction mixture refluxed for 16 hours, 31 g. of product was obtained of 96% purity by GLC.

B. 4-Bromo-1-hydroxy-2,2,4-trimethylpentan-3-one

To a stirred, refluxing solution of 69 g. (0.48 mole) of 1-hydroxy-2,2,4-trimethylpentan-3-one in 500 ml. of chloroform was added dropwise a solution of 77 g. (0.48 mole) bromine in 100 ml. of chloroform. When the addition was completed the mixture was stirred at reflux for one hour, allowed to cool and stand overnight at room temperature. Evaporation of solvent at reduced pressure afforded 127 g. of product which was used in the next step without purification.

C. 2,2,4,4-Tetramethyltetrahydrothiophen-3-one

The product obtained in Part B, 79 g. (0.3 mole) was dissolved in 300 ml. of dry pyridine, cooled to 0° C. and 114 g. (0.6 mole) of p-toluenesulfonyl chloride was added in portions at 0° C. The resulting mixture was stirred at this temperature for 3 hours, 15 minutes, poured into ice/water and extracted with ethyl ether. The extracts were washed with dilute hydrochloric acid, water and brine then dried over anhydrous magnesium sulfate. The solvent was evaporated to provide 111 g. (98%) of crystalline tosylate.

The tosylate, 94 g. (0.25 mole) was dissolved in one liter of pyridine, 180 g. (0.75 mole) of sodium sulfide monohydrate added and the mixture heated to 75° C. and held at this temperature for one hour and allowed to stand at room temperature overnight. Water was added and the mixture was extracted with ether. The extracts washed with hydrochloric acid, brine, dried (MgSO4) and the solvent evaporated to obtain 5 g. of the title compound, 89% yield. The product showed only one spot upon silica gel TLC, eluting with ethyl acetate/hexane (1:4 by volume, $R_f$ 0.5. The $^1$H-NMR spectrum was in agreement with the structure for the title compound.

D. Leuckart reduction of ketone

To a 100 ml. round-bottomed three-necked flask fitted with stirrer, thermometer and condenser with fractionating head was added 10.0 g. (0.063 mole) of 2,2,4,4-tetramethyltetrahydrothiophen-3-one, 15.2 ml. (0.38 mole) formamide and 3.5 ml. (0.092 mole) formic acid and the mixture heated at reflux (163° C.) while removing water. The reaction mixture was maintained at 160°–180° C. for 20 hours with addition of formic acid (10 ml.) at intervals. The pot temperature increased to 200° C. over this period. The reaction mixture was cooled, water added and the mixture extracted with ethyl acetate. The extracts were evaporated in vacuo. The residue was refluxed with 20 ml. of 6N hydrochloric acid for two hours, cooled, the resulting mixture washed with ethyl ether, the aqueous phase adjusted to pH 11 with sodium hydroxide solution and extracted with ethyl ether. The extracts were dried and evaporated to obtain 2 g. of 3-amino-2,2,4,4-tetramethyltetrahydrothiophene which was identified by $^1$H-NMR and appeared homogeneous upon silica gel TLC.

E. By employing the appropriate ketone as starting material in place of diisopropylketone in the procedures of Examples 8 and 13, the following amines are similarly obtained.

| X | $R^3$ | $R^4$ | $R^5$ | $R^6$ |
|---|---|---|---|---|
| S | $CH_3$ | H | $CH_3$ | H |
| S | H | H | $CH_3$ | H |
| S | $CH_3CH_2$ | H | $CH_3CH_2$ | H |
| S | $(CH_3)_2CH$ | H | $(CH_3)_2CH$ | H |
| S | $CH_3$ | $CH_3$ | H | H |
| O | $CH_3CH_2$ | H | $CH_3CH_2$ | H |
| O | $CH_3$ | H | $CH_3$ | H |
| O | H | H | $CH_3$ | H |
| O | $CH_3$ | H | H | H |
| O | H | H | $(CH_3)_3C$ | H |
| O | $CH_3CH_2$ | H | n-$C_4H_9$ | H |
| O | $CH_3$ | $CH_3CH_2$ | $CH_3$ | $CH_3CH_2$ |

When the tetrahydrothiophenes of the above formula are contacted with an equimolar amount of hydrogen peroxide or m-chloroperbenzoic acid the corresponding sulfoxide (X=SO) is formed in each case. Treatment of the same starting material or the sulfoxide with a molar excess of the same reagents or potassium permanganate affords the corresponding sulfone (X=$SO_2$).

EXAMPLE 14

L-Aspartyl-D-alanine
N-(2,2,4-tetramethyltetrahydrothiophene-3-yl)amide:

A.

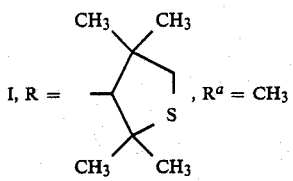

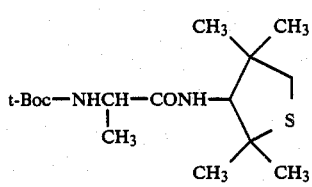

To a solution of 2.09 g. (11 mmole) of N-t-butoxycarbonyl-D-alanine in 75 ml. of tetrahydrofuran was added 1.47 ml. (10 mmole) of triethylamine and the mixture cooled to −10° C. At this temperature was added 0.96 ml. (10 mmole) of ethyl chloroformate and stirring continued for 15 minutes. After cooling to −20° C., 1.6 g. (10 mmole) of dl-3-amino-2,2,4,4tetramethyltetrahydrothiophene was added and the resulting mixture was allowed to warm to room temperature. Ethyl acetate was added and the mixture washed twice with 50 ml. portions of 5% (by weight) aqueous citric acid, aqueous sodium bicarbonate (1×50 ml.) and saturated brine (1×50 ml.). The organic layer was dried (Na and evaporated to dryness at reduced pressure to afford 3 g. of N-(2,2,4,4-tetramethyltetra-hydrothiophene-3-yl)-t-butoxycarbonyl-D-alanine amide as an oil. The structure of the product was verified by its $^1$H-NMR spectrum. It was essentially homogeneous upon silica gel TLC. This product was used without further purification in the next step.

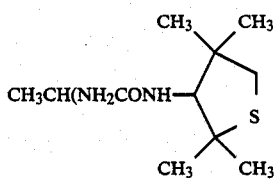

To the product from Part A was added 5 ml. of methanol and 30 ml. of 1M hydrochloric acid and the mixture was heated on the steam-bath for 30 minutes. The methanol was removed by evaporation and the residue extracted with ether. The ether was discarded and the aqueous phase was adjusted to pH 11.0 with sodium hydroxide solution, extracted with ethyl acetate, the extracts dried (Na$_2$SO$_4$) and evaporated to dryness to obtain 1.0 g. of N-(2,2,4,4-tetramethyltetrahydro-thiophene-3-yl)-D-alanine amide which was identified by its nuclear magnetic resonance spectrum. It was homogeneous upon silica gel TLC.

C. Coupling to form dipeptide amide

The D-alanine amide obtained in Part B, 0.97 g. (4.25 mmole) was mixed with 10 ml. of water, cooled in ice and the pH of the mixture adjusted to 9.2 with 0.5 N sodium hydroxide solution. To this was added portionwise with stirring 0.8 g. (4.25 mmole) of L-aspartic acid N-thiocarboxyanhydride while maintaining the mixture at pH 9 with sodium hydroxide solution (0.5 N). When the addition was completed the resulting mixture was stirred at 0° C. for 45 minutes, adjusted to pH 5.2 with hydrochloric acid and evaporated to dryness in vacuo. The residue was slurried with methanol, filtered to remove precipitated solids and methanol removed from the filtrate by evaporation at reduced pressure. Ethyl ether was added to the residue to form a solid. This was collected by filtration, reslurried with ethyl ether, filtered again and the solid recrystallized from 8 ml. of water. After drying in the vacuum oven about 1 g. of product was obtained, M.P. 124°–126° C. A second crop was obtained by reworking the mother liquors. Sweetness, 500×sucrose.

When levorotatory 3-amino-2,2,4,4-tetramethyltetrahydrothiophene, resolved by standard methods, was employed in the above procedure in place of the racemic amine the resulting L-aspartyl-D-alanine amide was found to be 800 times as sweet as sucrose.

Similarly, the analogous compounds of formula (I) wherein $R^a$ is ethyl, isopropyl or n-propyl are prepared from the appropriate N-t-boc-D-amino acid by the above procedures.

EXAMPLE 15

3-Amino-2,2,4,4-tetramethylthietane

A. 2,4-Dibromo-2,4-dimethylpentan-3-one

To 136 g. (1.2 mole) of diisopropylketone was added 2 ml. of phosphorus tribromide and the mixture cooled to 10° C. To this was added dropwise 384 g. (2.4 mole) of bromine, the mixture allowed to warm to room temperature. After two hours at this temperature the mixture was warmed at 55°–60° C. for one hour then cooled and partioned between chloroform and water. The water was discarded and the organic layer washed with sodium carbonate solution until neutral. The organic layer was dried (MgSO$_4$) and solvent evaporated to obtain 316 g. (97%) of the desired product.

B. 2,2,4,4-Tetramethyl-3-oxothietane

Sodium metal, 23 g. (1.0 mole), was dissolved in 500 ml. of dry methanol and the resulting mixture cooled to 10° C. Hydrogen sulfide gas was passed through the mixture until it was saturated. Then 136 g. (0.5 mole) of the dibromoketone obtained in Part A was added dropwise while continuing to allow hydrogen sulfide to pass through the reaction mixture. After the addition was completed the mixture was stirred for two hours at 10° C., allowed to warm to room temperature and stirred overnight. After pouring the reaction mixture into water, it was extracted with ethyl ether and the extracts washed with dilute hydrochloric acid and brine. After drying over magnesium sulfate the ether was evaporated, the residue slurried with methanol, cooled and filtered to obtain 46 g. (64%) of solid product which was used without purification in the next step.

C. Reductive amination of ketone

To 75 ml. of dry methanol was added 4.5 g. (0.031 mole) of 2,2,4,4-tetramethyl-3-oxothietane, 23.9 g. (0.31 mole) ammonium acetate and 1.36 g. (0.0217 mole) sodium cyanoborohydride and the resulting mixture heated at reflux for four hours. Additional sodium cyanoborohydride (1.36 g.) was added and refluxing continued for three days with a third increment of the same reagent added at the start of the third day. The resulting mixture was acidified to pH 2 with hydrochloric acid and evaporated to dryness on the rotary evaporator at reduced pressure. The residue was dissolved in water, washed with ethyl ether, the aqueous phase adjusted to pH 11 with sodium hydroxide solution and extracted with ethyl ether. The extracts were washed with brine, dried (MgSO$_4$) and evaporated to dryness to obtain 1.9 g. (42%) of the desired amine as a crystalline solid. The structure of the product was verified by its $^1$H-NMR spectrum.

D. 3-Amino-2,2,4,4-tetramethylthietane-1,1-dioxide

The amine obtained in Part C, above, 29 g. (0.2 mole) was dissolved in 50 ml. acetonitrile and 250 ml. water added. While maintaining the mixture at pH 10 with sodium hydroxide, 35.8 g. (0.21 mole) carbobenzoxy chloride was added over 30 minutes, the mixture stirred for one hour, filtered, the precipitate washed with water and dried in vacuo at 50° C. to provide the NCbz-amine, R$_f$ 0.7 (hexane/ethyl acetate 4:1 v/v, phosphomolybdic acid spray), 52.1 g. (93.4%). This was dissolved in 700 ml. methylene chloride, 77 g. (0.372 mole) m-chloroperbenzoic acid was added slowly while maintaining the temperature below 45° C. (20°–42° C.). The precipitated solid was collected by filtration, the filtrate was washed with 1N hydrochloric acid, aqueous sodium bicarbonate solution, dried (MgSO$_4$) and the solvent evaporated. The residue was crystallized from acetone-water to obtain 42 g. (73%) of the Cbz-protected amine 1,1-dioxide, R$_f$ 0.7 (hexane/ethyl acetate 1:1 v/v, phosphomolybdic acid spray).

The protecting group was removed by hydrogenolysis of 5 g. of Cbz-amine in 250 ml. methanol, 5 ml. concentrated hydrochloric acid and 2 g. of 5% Pd/C (50% wet). The product was isolated in the usual manner. Yield: 2.4 g. (85%), R$_f$ 0.6. The retention time upon gas-liquid chromatography on a 1 meter, OV-1 column at 180° C. was 1.3 minutes. The overall yield for the three steps starting from 3-amino-2,2,4,4-tetramethylthietane was 65%.

By employing equivalent amounts of amine and m-chloroperbenzoic acid in the above procedure the corresponding sulfoxide is obtained in like manner.

E. Employing the appropriate ketone of formula R$^3$R$^4$CHOCHR$^5$R$^6$ in place of diisopropylketone in the procedures of Parts A-C afords the corresponding amines of the formula shown below.

| R$^3$ | R$^4$ | R$^5$ | R$^6$ |
|---|---|---|---|
| CH$_3$ | H | CH$_3$ | H |
| CH$_3$ | H | H | H |
| C$_2$H$_5$ | H | H | H |
| i-C$_3$H$_7$ | H | H | H |
| i-C$_3$H$_7$ | H | i-C$_3$H$_7$ | H |
| t-C$_4$H$_9$ | H | H | H |
| t-C$_4$H$_9$ | H | t-C$_4$H$_9$ | H |
| n-C$_4$H$_9$ | H | n-C$_4$H$_9$ | H |
| C$_2$H$_5$ | H | C$_2$H$_5$ | H |

The corresponding sulfoxides and sulfones are prepared by the procedure of Part D above.

EXAMPLE 16

L-Aspartyl-D-alanine N-(2,2,4,4-tetramethylthietan-3-yl)amide:

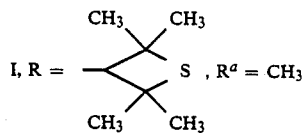

A.

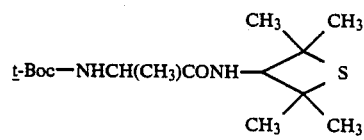

To a solution of 2.09 g. (11 mmole) N-t-butoxy-carbonyl-D-alanine in 75 ml. of tetrahydrofuran was added 1.47 ml. (10 mmole) triethylamine and the mixture cooled to −10° C. Ethyl chloroformate, 0.96 ml. (10 mmole) was added, the mixture stirred for ten minutes then cooled to −20° C. and 1.70 g. (11 mmole) of 3-amino-2,2,4,4-tetramethylthietane dissolved in 5 ml of tetrahydrofuran added. The reaction mixture was allowed to warm to room temperature, ethyl acetate added and the mixture washed with 5% (by weight) citric acid solution (2×50 ml.), sodium bicarbonate solution until neutral, then with brine. The organic layer was dried (Na$_2$SO$_4$) and solvent rmmoved by evaporation to provide 2.7 g. (78%) of the desired solid product. The $^1$H-NMR spectrum of the product was in agreement with that expected. Upon silica gel TLC, eluting with 1:1 ethyl acetate/hexane the product appeared homogeneous, R$_f$ 0.77.

B.

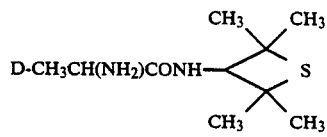

Employing the procedure described in Example 12, Part F, the t-Boc-D-alanine amide provided in Part A of this example was hydrolyzed to obtain the free alpha-aminoamide in 43% yield. The product was homogeneous upon silica gel TLC and gave a $^1$NMR spectrum in agreement with its structure.

C. Coupling to form dipeptide amide

A solution of 0.7 g. (3.2 mmole) of the alphaaminoamide prepared in Part B, above, was mixed with 10 ml. of water, adjusted to pH 10.1, cooled in an ice-bath and 0.567 g. (3.2 mmole) of L-aspartic acid N-thiocarboxy-anhydride added portionwise while maintaining the mixture at pH 9 by addition of 0.5 N sodium hydroxide solution. The mixture was then stirred at 0° C. for 45 minutes, adjusted to pH 5.2 and evaporated to dryness in vacuo. The residue was slurried in methanol, solids removed by filtration and the filtrate evaporated. To the residue was added 150 ml. of ethyl ether, the precipitated product collected by filtration and dried in the vacuum oven overnight to obtain 1.5 g. of crude material. After reslurrying two more times with ethyl ether, 0.9 g. of product (85%) was obtained. Sweetness, 2000 x sucrose.

The corresponding compounds of formula (I) wherein $R^a$ is $C_2H_5$, i-$C_3H_7$ or n-$C_3H_7$ are similarly obtained by the above procedures employing the appropriate N-t-boc-amino acid in place of N-t-boc-D-alanine.

EXAMPLE 17

L-Aspartyl-D-alanine N-(2,2,4,4-tetramethyl-1,1-dioxothietan-3-yl)amide

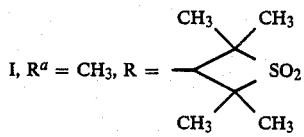

A.

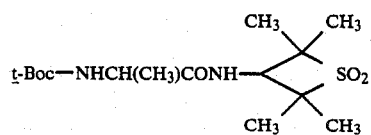

A solution of 31.6 g. (0.10 mole) of N-t-butoxy-carbonyl-D-alanine N-(2,2,4,4-tetramethylthietan-3yl)amide, provided in Example 16, Part A, in 500 ml. chloroform was cooled to 10°-20° C. and 41.3 g. (0.24 mole) m-chloroperbenzoic acid was added slowly while maintaining the reaction temperature below 45° C. The resulting mixture was stirred for one hour, diluted with chloroform and washed in turn with 5% aqueous sodium bicarbonate, 0.1N hydrochloric acid, 5% sodium thiosulfate and saturated brine. The washed organic layer was dried (MgSO$_4$) and evaporated to dryness to provide 33.7 g. of residual oil (97%) of suitable purity for use in the next step.

B.

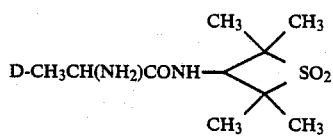

The t-Boc-amide obtained in Part A, above, 34.8 g. (0.10 mole) dissolved in a mixture of 50 ml. concentrated hydrochloric acid and 100 ml. each of water and ethanol was heated at reflux for one hour. The mixture was cooled, washed with ethyl ether, the aqueous phase adjusted to pH 12 with 50% aqueous sodium hydroxide and extracted with ethyl acetate. The extracts were dried (MgSO$_4$) and evaporated in vacuo to obtain 18.7 g. (75%) of crystalline solid. This was recrystallized from carbon tetrachloride with 80% recovery of product.

C. Diblocked dipeptide amide

To a solution of 14.28 g. (0.04 mole) beta-benzyl N-benzyloxycarbonyl-L-aspartate in 700 ml. tetrahydrofuran was added 4.4 ml. (0.04 mole) N-methylmorpholine and the mixture cooled to −10° C. Ethyl chloroformate, 3.9 ml. (0.04 mole) was added, the mixture stirred at −10° C. for 15 minutes and cooled to −20° C. A solution of 9.92 g. (0.04 mole) D-alanine N-(2,2,4,4-tetramethyl-1,1-dioxothietan-3-yl)amide from Part B, above, in 50 ml. tetrahydrofuran was added and the resulting mixture stirred at ambient temperature for one hour. The reaction mixture was poured into 700 ml. ethyl acetate, washed in turn with N hydrochloric acid, sodium bicarbonate solution, 0.1 N sodium hydroxide and brine. The washed extracts were dried (MgSO$_4$) and evaporated in vacuo. The residue was slurried in ethyl ether and the solid collected by filtration to afford 19.8 g. (84%) of diblocked dipeptide amide which was recrystallized from ethyleneglycol dimethyl ether/isopropyl ether with 77% recovery.

D. To a solution of 10 g. of the product obtained in Part C, above, in 250 ml. methanol was added 3 g. of 5% Pd/C (50% wet) and 1 ml. concentrated hydrochloric acid and the mixture hydrogenated for one hour at 50 psi (3.52 kg./cm.$^2$). The catalyst was removed by filtration, the filtrate adjusted to pH 5.2 with sodium hydroxide solution and evaporated in vacuo to near dryness. The residue was mixed with ethyl ether and the solid collected by filtration and dried in the vacuum oven at 45° C. to obtain 5.5 g., 89% of the desired dipeptide amide.

Sweetness, 1000 x sucrose.

E. By use of one equivalent of m-chloroperbenzoic acid in the method of Part A, above, the corresponding t-Boc-D-alanine mide sulfoxide is obtained which, when carried through the procedures of Parts B, C and D, above, provides L-aspartyl-D-alanine N-(2,2,4,4-tetramethyl-1-oxothietan-3-yl)amide.

EXAMPLE 17A

Employing the procedures of Examples 12–17, corresponding L-aspartyl-D-amino acid amides (I) wherein $R^a$ is methyl, ethyl, isopropyl or n-propyl and R is as defined below are prepared from the appropriate starting materials via D-RaCH(NH2)CONHR intermediates. The corresponding L-aspartyl-DL-amino acid amides are similarly provided when a t-Boc-DL-amino acid is employed in place of the D-enantiomer. Likewise, use of DL-aspartic N-thiocarboxyanhydride in the coupling step affords the DL-D or DL-DL compounds of formula (I).

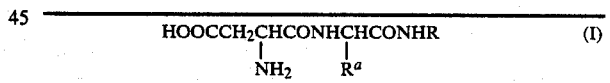

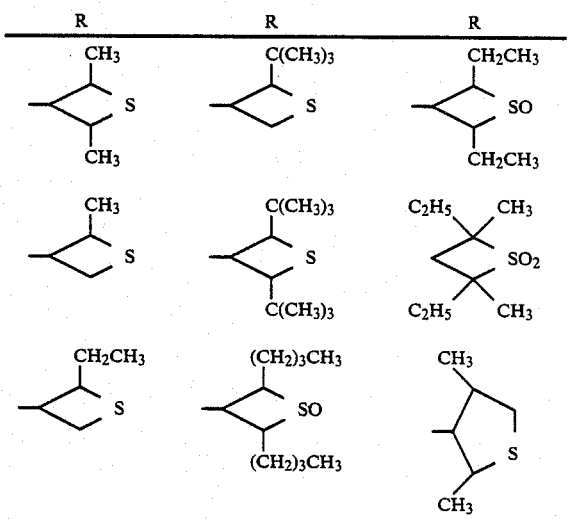

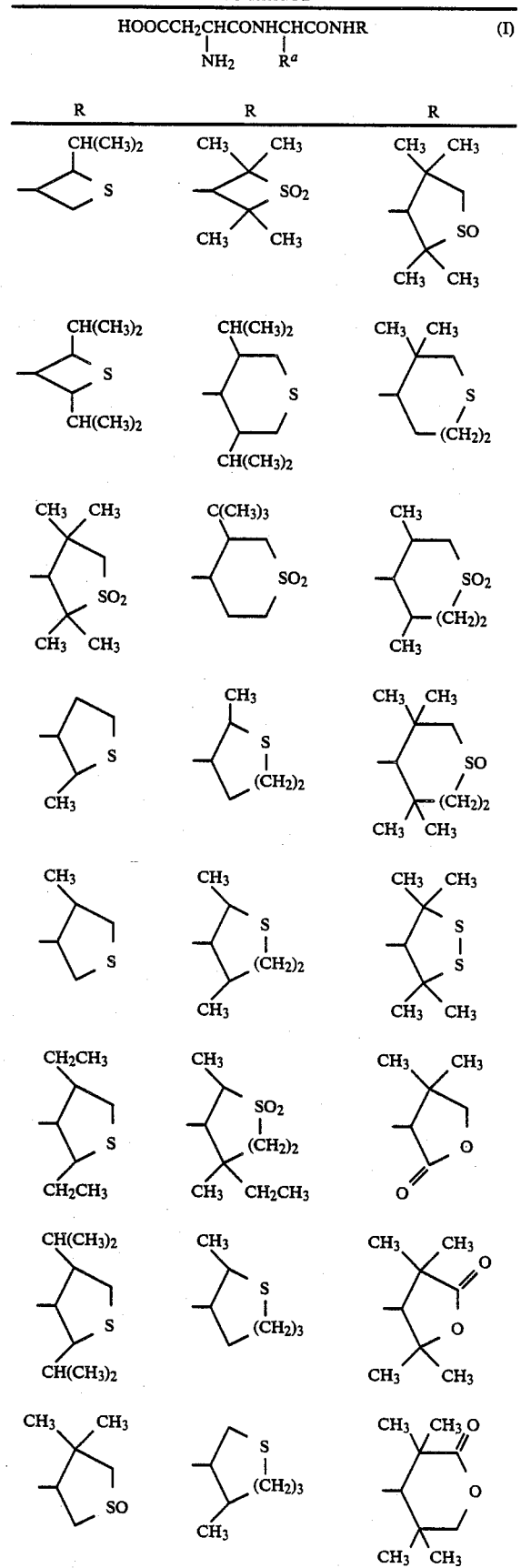
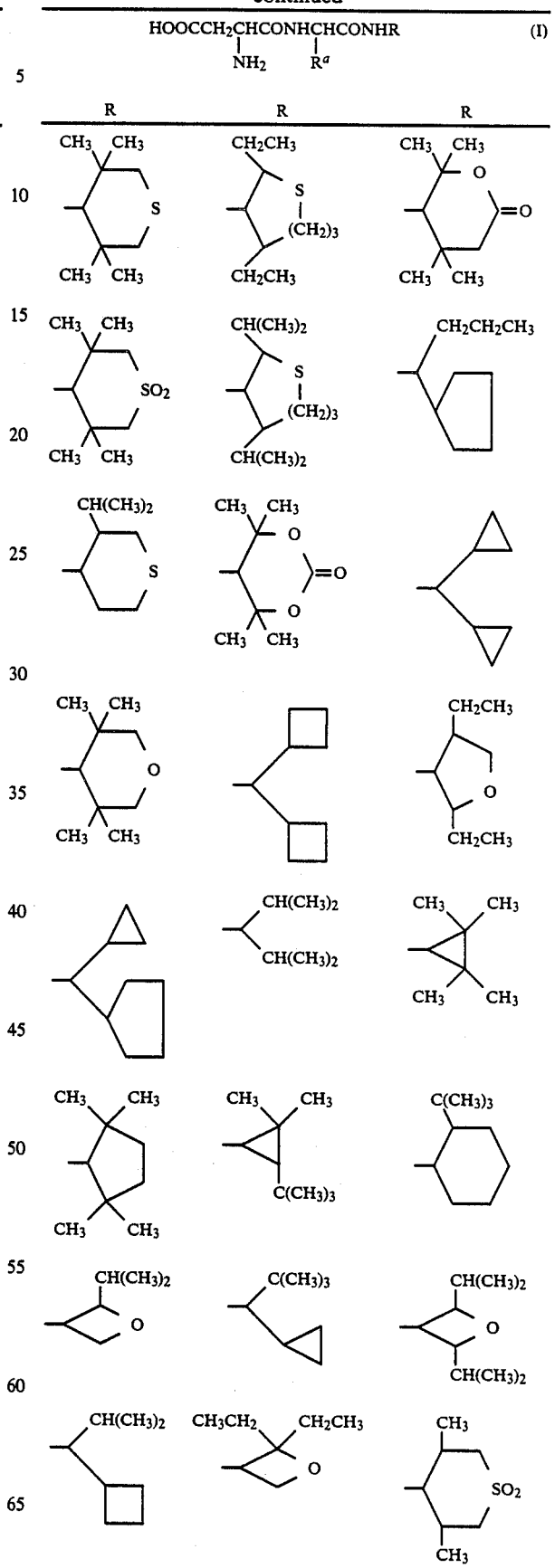

-continued

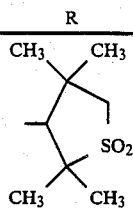

EXAMPLE 18

L-Aspartyl-D-alanine N-(2-methylthio-2,4-dimethylpentan-3-yl)amide

A. 2-Methylthio-2,4-dimethylpentan-3-one

A solution of 200 ml. of methanol containing 9.2 g. (0.40 mole) sodium metal was cooled in an ice-bath and saturated with gaseous methyl mercaptan. To this was added 77.2 g. (0.40 mole) of 2-bromo-2,4-dimethyl-pentan-3-one at room temperature and the resulting mixture stirred for two hours. The reaction mixture was diluted with water, extracted with ethyl ether, the extracts washed with water, brine and dried over anhydrous sodium sulfate. The ether was evaporated and the residue distilled in vacuo to afford 50.4 g. of product, B.P. 76° (20 mm.).

B. 2-Methylthio-2,4-dimethyl-3-aminopentane

A solution of 6.0 g. (0.038 mole) 2-methylthio2,4-dimethylpentan-3-one, 9.9 g. formamide and 2.1 g. of 100% formic acid was heated at reflux while removing water formed in the reaction by means of a fractionating head. After 12 hours an additional 2.5 g. of formic acid was added and reflux continued for another 24 hours in the same manner, by which time the reaction mixture reached a temperature of 190° C. The mixture was cooled, diluted with water and extracted with ethyl acetate. The extracts were washed with water and evaporated to dryness at reduced pressure to provide 5.3 g. of residual oil. The oil was refluxed with 40 ml. of 6N hydrochloric acid for six hours, diluted with water, washed with ether and the aqueous phase made strongly alkaline with sodium hydroxide. After extracting with ethyl ether and evaporation of the extract, 3.3 g. (56%) of colorless amine was obtained which gave a single peak by gas-liquid chromatography on a six foot OV-1 column at 110° C.; retention time 412 seconds.

C. D-Alanine N-(2-methylthio-2,4-dimethylpentan-3-yl)amide

To a solution of 3.2 g. (0.017 mole) N-t-butoxy-carbonyl-D-alanine and 2.5 g. (0.017 mole) triethylamine in 100 ml. of tetrahydrofuran at −15° C. was added 1.63 ml. of ethyl chloroformate. After stirring for 15 minutes, 2.49 g. (0.017 mole) 2-methylthio-2,4-dimethyl3-aminopentane was added and the mixture stirred for one hour. The reaction mixture was diluted with ethyl acetate, washed with water, 5% aqueous citric acid (w/v), sodium bicarbonate solution and brine. The organic phase was evaporated to provide 6.0 g. of residue. This was taken up in 100 ml. methanol, 60 ml. of concentrated hydrochloric acid added and the mixture refluxed for one hour. After evaporation of methaol, the residue was taken up in water, washed with ether, the aqueous phase adjusted to pH 12 with sodium hydroxide and extracted with ethyl ether. Evaporation of the extracts gave 3.2 g. (87%) of product as a colorless oil $R_f$ 0.56 (butanol/water/acetic acid-4:1:1 by volume).

D. A solution of 3.1 g. (0.013 mole) of the D-alanine amide, obtained in Part C, in 30 ml. acetone and 17 ml. water was adjusted to pH 9.9 with sodium hydroxide solution and cooled to −2° C. To this was added 2.78 g. (0.013 mole) L-aspartic N-thiocarboxy-anhydride in small portions over 20 minutes while maintaining the pH at 9.9 with 1N sodium hydroxide. When the addition was completed, the resulting mixture was stirred for 30 minutes at −2° C., washed with ethyl acetate acidified to pH 2 with hydrochloric acid and washed again with ethyl acetate. The aqueous phase was then adjusted to pH 5.2 and evaporated to dryness. The crude dipeptide amide was obtained by slurrying the residue in methanol, filtering, treatment of the filtrate with ether and filtering to obtain a second crop. Total crude yield 4.7 g.

The crude product was purified by preparative layer chromatography on silica gel plates (20×20×2 mm.) eluting with butanol/water/acetic acid, 4:1:1 by volume. The band at $R_f$ 0.42 was cut out and eluted with methanol to give the pure L-aspartyl-D-alanine amide.

Sweetness: 150 x sucrose.

EXAMPLE 19

N-Benzyloxycarbonyl-D-2-aminobutyric acid

In a 500 ml. reaction vessel fitted with mechanical stirrer, thermometer and two addition funnels was added 20.0 g. (0.194 mole) of commercial D-(-)-2-aminobutyric acid and a solution of 7.76 g. (0.194 mole) sodium hydroxide in 97 ml. water. The mixture was stirred until solution was complete and cooled to 5° C. Simultaneously from the addition funnels were added 40.66 g. (0.205 mole) of 86% benzyl chloroformate and a solution of 7.76 g. sodium hydroxide in 58 ml. water. The temperature was maintained at 4°–6° C. during the addition. The reaction temperature then increased slowly to 14° C. Stirring was continued for 15 minutes after the temperature subsided, then allowed to warm to room temperature. The reaction mixture was washed with 3×75 ml. ethyl ether, the aqueous phase adjusted to pH 2 with concentrated hydrochloric acid (16 ml.) causing the product to separate as an oil. The oil was extracted with 3×100 ml. ether, dried (MgSO4) and the solvent evaporated to provide a clear, colorless liquid residue which was dried overnight at 0.3 mm. Hg. during which the product crystallized to afford 41.24 g. (89.6%) of the title compound. A 1.0 g. portion was recrystallized from 5 ml. xylene, washing the precipitate with xylene and pentane. After drying overnight 0.77 g. of colorless crystals were obtained, $R_f$ 0.57 upon TLC on silica gel (solvent: ethyl acetate/hexane/acetic acid 4:14:2 by volume; plate sprayed with 3% vanillin), M.P. 76°–78° C., [alpha]$_D$ +10 (c=2.8, ethanol).

Analysis Calculated for $C_{12}H_{15}NO_4$: C, 60.75; H, 6.37; N, 5.90

Found: C, 60.61; H, 6.41; N, 5.97.

The remainder of the crude crystals (40 g.) was recrystallized from xylene (150 ml.), washing with xylene (3×25 ml.) and pentane (2×25 ml.) and dried in vacuo at 45° C. to afford 28.69 g. (71.7%) colorless crystals, M.P. 78°–79° C.

EXAMPLE 20

L-Aspartyl-D-2-aminobutyric acid N-(dicyclopropylcarbinyl)amide,

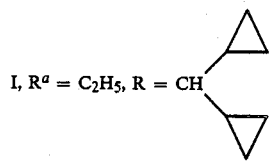

A.

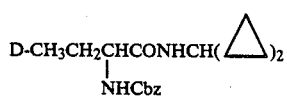

N-Benzyloxycarbonyl-D-2-aminobutyric acid, 4.75 g. (0.020 mole) was dissolved in 200 ml. tetrahydrofuran and cooled under a nitrogen atmosphere to −15° C. N-Methylmorpholine, 2.02 g. (0.020 mole) and ethyl chloroformate, 2.17 g. (0.020 mole), were added and the resulting mixture stirred at −15° to −10° C. for 30 minutes. The resulting solution of mixed anhydride was cooled to −20° C. and 2.22 g. (0.020 mole) dicyclopropylcarbinylamine dissolved in 10 ml. tetrahydrofuran was added. Stirring was continued for 15 minutes at −20 to −15° C., after which the mixture was allowed to warm to room temperature, 150 ml. ethyl acetate was added and the mixture extracted with 2×100 ml. N hydrochloric acid, 2×100 ml. 5% aqueous sodium bicarbonate solution and 100 ml. saturated brine. The organic layer was dried (MgSO$_4$) and the solvent evaporated at reduced pressure to afford 6.62 g. (100%) of colorless solid, R$_f$0.68 upon TLC on silica gel (solvent: ethyl acetate/hexane, 1:1 by volume; plate sprayed with 3% vanillin).

B.

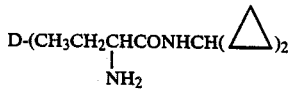

The Cbz-amino-protected amide obtained in Part A, above, 6.62 g. (0.020 mole) was dissolved in 250 ml. reagent grade methanol. 5% Palladium-on-carbon catalyst, 1.5 g., was added and the mixture hydrogenated at 50 psi (3.52 kg./cm.$^2$) for 45 minutes. The catalyst was removed by filtration and the filtrate evaporated in vacuum to provide a liquid residue. N Hydrochloric acid, 25 ml., was added, the mixture stirred then extracted with 25 ml. ethyl ether. The aqueous phase was made strongly alkaline (pH 14) with 10 M sodium hydroxide and the mixture extracted with 3×25 ml. ether. The extracts were combined, dried (MgSO$_4$) and the ether evaporated to afford 3.29 g. (83.9%) of colorless solid, M.P. 63°–64° C. R$_f$0.60 (butanol/acetic acid/water, v/v; ninhydrin spray); [alpha]D −46.7° (c=2, 1N HCl). The $^1$NMR spectrum was in agreement with the structure of D-2-aminobutyric acid N-(dicyclo-propylcarbinyl)amide.

C. Diblocked dipeptide amide

To beta-Benzyl N-benzyloxycarbonyl-L-aspartate, 5.61 g. (0.0157 mole) dissolved in 50 ml. tetrahydrofuran and cooled to −15° C., was added 1.59 g. (0.0157 mole) N-methylmorpholine. To this was added dropwise 1.70 g. (0.0157 mole) ethyl chloroformate, the resulting mixture stirred for 30 minutes at −15° C. and a solution of D-2-aminobutyric acid N-(dicyclopropylcarbinyl)amide in 15 ml. tetrahydrofuran was added dropwise. Stirring was continued for 15 minutes at −15° C., then the reaction mixture was allowed to warm to room temperature. The solvent was evaporated in vacuo to afford a solid residue. This was mixed with 150 ml. ethyl acetate and the resulting suspension washed with 2×75 ml. N hydrochloric acid. The clear organic layer was washed with 2×75 ml. 5% aqueous sodium bicarbonate, 75 ml. brine, dried (MgSO$_4$) and the solvent evaporated in vacuo to afford 8.36 g. (99.5%) of colorless solid, R$_f$0.36 on TLC (ethyl acetate/hexane, 1:1, vanillin spray). Recrystallization from ethyl acetate gave 6.12 g. (73%) crystals, M.P. 167°–168° C.

D. To a solution of the diblocked dipeptide amide, obtained in Part C, in 250 ml. of methanol was added 1.5 g. 5% (w/w) Pd/C (50% wet) catalyst and the mixture hydrogenated at 50 psi (3.52 kg./cm.$^2$) for 45 minutes during which the theoretical amount of hydrogen was consumed. The catalyst was removed by filtration, the filtrate evaporated in vacuo to a volume of about 5 ml. The concentrate was filtered to remove the precipitated product which was washed with methanol and dried in vacuo to provide 2.85 g. colorless powder, M.P. 225°–227° C. (decomp.). An additional 0.76 g. was obtained from the mother liquor. Total yield: 100%. R$_f$ 0.56 (butanol/acetic acid/water, 4:1:1; ninhydrin spray).

Sweetness, 500 x sucrose.

EXAMPLE 21

L-Aspartyl-D-2-aminobutyric acid N-(2,2,4,4-tetramethyl-1,1-dioxothietan-3-yl)amide:

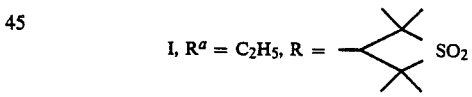

A.

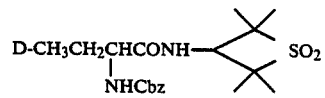

Employing 3-amino-2,2,4,4-tetramethylthietan 1,1-dioxide in place of dicyclopropylcarbinylamine in the procedure of Example 20, Part A, afforded N-benzyloxy-carbonyl-D-2-aminobutyric acid N-(2,2,4,4-tetramethyl1,1-dioxothietan-3-yl)amide in 99% yield, R$_f$ 0.50.

B. Hydrogenolysis of the above product by the procedure of Example 20, Part B, afforded D-2-aminobutyric acid N-(2,2,4,4-tetramethyl-1,1-dioxothietan-3-yl)amide in 18% step yield, R$_f$0.41.

C. The corresponding diblocked dipeptide amide,

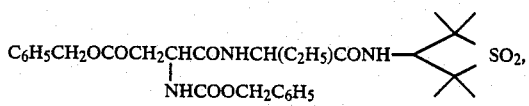

$R_f$ 0.68, was obtained in 99% step yield by the procedure of Example 20, Part C.

D. Hydrogenolysis of the product obtained in Part C, above, (1.16 g.) by the procedure of Example 20, Part D, employing 0.4 g. of 5% Pd/C (50% wet) afforded the title compound in 92% step yield, M.P. 165°-167° C. (decomp.), $R_f$ 0.4.

Sweetness, 200 x sucrose.

EXAMPLE 22

L-Aspartyl-D-2-aminobutyric acid N-(2,4-dimethyl-3-pentyl)amide

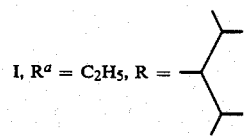

A.

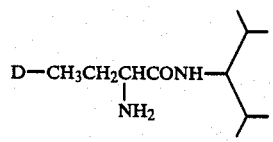

Employing the appropriate amine in the procedure of Example 20, Part A, and hydrogenolysis of the crude product by the procedure of Example 20, Part B gave the diisopropylcarbinyl amide of D-2-aminobutyric acid in 85% yield as an oil, $R_f$ 0.56.

B. The corresponding diblocked amide, $C_6H_5CH_2OCOCH_2$

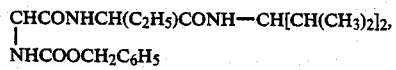

was obtained in 76% step yield by the procedure of Example 20, Part C, and this was hydrogenated by the procedure of Example 20, Part D to obtain the title compound in 89% step yield (68% overall yield), M.P. 213°-215° C. (decomp.), $R_f$ 0.54.

Sweetness, 100 x sucrose.

EXAMPLE 23

L-Aspartyl-D-valine N-(dicyclopropylcarbinyl)amide,

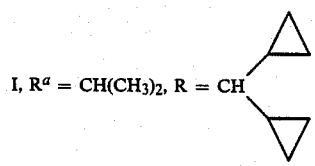

A.

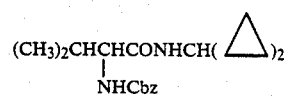

Employing commercially available D-valine in place of D-2-aminobutyric acid in the procedure of Example 19 afforded N-benzyloxycarbonyl-D-valine in 82% yield as a white powder, M.P. 55°-57° C., $R_f$ 0.45. This was reacted with dicyclopropylcarbinylamine in the procedure of Example 20, Part A to afford the desired blocked amide in 100% yield, $R_f$ 0.35.

B. Hydrogenolysis of the above product by the method of Example 20, Part B, afforded D-valine N-(dicyclopropylcarbinyl)amide in 83.7% yield, $R_f$ 0.53 as a colorless solid.

C. The corresponding diblocked dipeptide amide,

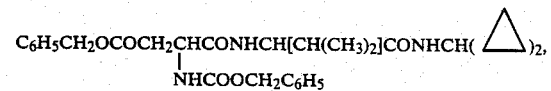

was obtained in 92.4% yield by the procedure of Example 20, Part C, $R_f$ 0.55 as an off-white solid.

D. Hydrogenolysis of the product of Part C, above by the procedure of Example 20, Part D, provided the title compound in 85% yield as a colorless solid, $R_f$ 0.54.

Sweetness, 110 x sucrose.

EXAMPLE 24

L-Aspartyl-D-valine N-isopropylamide I, $R^a = CH(CH_3)_2$, $R = CH(CH_3)_2$

Reaction of N-benzyloxycarbonyl-D-valine with isopropylamine by the method of Example 20, Part A afforded a quantitative yield of N-benzyloxycarbonyl-D-valine isopropylamide of $R_f$ 0.61 (TLC, ethyl acetate/hexane, 1:1, vanillin spray). Hydrogenolysis over Pd/C by the method of Example 20, Part B gave D-valine isopropylamide in 71% yield, $R_f$ 0.50. Coupling with beta-benzyl N-Cbz-L-asparate provided the diblocked dipeptide amide (procedure of Example 20, Part C), $R_f$ 0.40 (TLC, ethyl acetate/hexane, 1, vanillin spray), in 62% yield as an off-white solid. This was converted to the desired title compound by the procedure of Example 20, Part D, in 90.6% yield, M.P. 226°-227° C. (decomp.), $R_f$ 0.44. Sweetness, 1-2 x sucrose.

EXAMPLE 25

L-Aspartyl-D-alanine N-(2,2,4,4-tetramethyl-3-pentyl)amide,

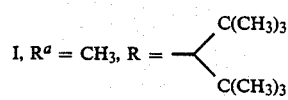

A. 2,2,4,4-Tetramethyl-3-aminopentane

This was prepared by the method of J. Chem. Soc., Perkin I, 2087 (1976); ibid, 1797 (1974). Pivalonitrile (33.2 g.) and t-butyl, chloride (44.4 g.) were added under nitrogen to a well stirred suspension of sodium sand (18.4 g.) in a mixture of hexane (80 ml.), tetrahydrofuran (20 ml.) and methanol (1 ml.) over one hour at 15°-20° C. The mixture was stirred three hours, a solution of chlorobenzene (2 g.) in tetrahydrofuran (5 ml.) added dropwise over 10 minutes and stirring continued for one hour. Methanol (20 ml.) was added with caution over 0.5 hr. followed by water until phases separated. The aqueous phase was extracted with ether and the combined organic phases dried and evaporated in vacuo. The residue was distilled to afford di-t-butylketone imine, b.p. 62°–63° C./19 mm.

The imine (14 g.) in dry ether (50 ml.) was added to a suspension of lithium aluminum hydride (1.7 g.) in dry ether (50 ml.). The mixture was stirred at room temperature for 24 hours, refluxed two hours and cooled. Water (1.7 ml.), 15% sodium hydroxide solution (5 ml.) and water (5 ml.) were added cautiously in succession, the mixture filtered, concentrated and the residue distilled to afford the desired amine, b.p. 79°–81° C./40 mm.

B. N-Benzyloxycarbonyl-D-alanine, 7.59 g. (0.034 mole) was added to 170 ml. methylene chloride containing 4.88 ml. (0.035 mole) triethylamine and the resulting solution cooled to −10° C. Ethyl chloroformate, 3.35 ml. (0.035 mole) was added, the mixture stirred at −10 to −5° C. for 25 minutes then 5.0 g. (0.034 mole) 2,2,4,4-tetramethyl-3-aminopentane was added and stirring continued overnight after allowing the mixture to warm to room temperature. The reaction mixture was washed with 2×100 ml. 5% aqueous sodium bicarbonate, 2 x 100 ml. 3 M hydrochloric acid, dried (MgSO44) and the solvent evaporated in vacuo to leave 9.99 g. (82%) N-Cbz-D-alanine N-(2,2,4,4-tetramethyl-3-pentyl)amide, identified by its ¹NMR spectrum, R_f 0.72 (TLC, ethyl acetate/hexane, 1:1, phosphomolybdate spray).

C. The above Cbz-D-alanine amide, 9.99 g. was dissolved in 250 ml. methanol, 1.6 g. 5% Pd/C catalyst (50% wet) added and the mixture hydrogenated at 45–75 psi (12.8–21.3 kg./cm.²) for 30 minutes. The catalyst was filtered off, the filtrate evaporated in vacuo to leave a white solid. To this was added 100 ml. 1 N hydrochloric acid, the mixture stirred for two hours, washed with ethyl ether, then made alkaline with 40% (w/w) sodium hydroxide solution. The basic solution was extracted with ethyl ether, the ether dried over magnesium sulfate and evaporated to afford 1.1 g. of colorless product identified as D-alanine N-(2,2,4,4-tetramethyl-3-pentyl)amide, R_f 0.59 (butanol/water/acetic acid, 4:1:1, ninhydrin then phosphomolybdate sprays).

D. The diblocked dipeptide amide was prepared on a 0.005 molar scale from the above amide and beta benzyl N-Cbz-L-aspartate, employing triethylamine and ethyl chloroformate in acetone (50 ml.) by the procedure of Example 20, Part C, in 80% yield, R_f 0.4 (TLC, ethyl acetate/hexane, 1:1, phosphomolybdate spray). It was purified by chromatography on 25 g. of silica gel, eluting with ethyl acetate/hexane, 2:3 by volume, to obtain 1.65 g. of purified liquid product.

E. The diblocked dipeptide amide, 1.15 g. (0.021 mole) was hydrogenolyzed in 150 ml. methanol with 0.2 g. 5% Pd/C by the method of Example 20, Part D, to afford 0.64 g. (93%) of the title compound, M.P. 145°–149° C. (decomp.), R_f 0.50.

Sweetness, 450 x sucrose.

Employing the appropriate starting N-Cbz-D-amino acid (-Cbz-NH-CH(R^a)COOH) in the procedure of Parts B-E provides the corresponding compounds of the formula

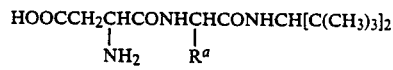

where R^a is ethyl, isopropyl or n-propyl.

EXAMPLE 26

L-Aspartyl-D-alanine N-(2-hydroxy-2,4-dimethyl-3-pentyl)amide,

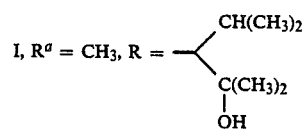

A. 2-Hydroxy-2,4-dimethyl-3-pentanone

To a stirred solution of 28.3 ml. (0.2 mole) 2,4-dimethyl-3-pentanone in 100 ml. chloroform was added dropwise 10.3 ml. (0.2 mole) bromine in 30 ml. of the same solvent. The resulting mixture was stirred for a few minutes, the solvent evaporated in vacuo, the residue taken up in 100 ml. ethanol. Water, 50 ml., and 10 M sodium hydroxide, 50 ml., added. The resulting mixture was stirred at reflux for one hour, diluted with 200 ml. water and extracted with 3×50 ml. ethyl ether. The extracts were dried (MgSO4) evaporated to dryness and the residue distilled to obtain 15.95 g. (61%) of the hydroxy-ketone, b.p. 60°–62° C./18 mm.

B. 3-Amino-2-hydroxy-2,4-dimethylpentane

The hydroxy ketone from Part A, 15 g. (0.115 mole) was reduced in refluxing mixture of formamide and formic acid by the method of Example 13, Part D, to obtain 4.5 g. (30%) of the hydroxy amine, b.p. 80°–81° C./ 17 mm.

C. Diblocked dipeptide amide

To a solution of 2.14 g. (5.0 mmole) beta-benzyl-N-benzyloxycarbonyl-L-aspartyl-D-alanine in 35 ml. tetrahydrofuran cooled to -15° C. was added 0.55 ml. (5.0 mmole) N-methylmorpholine and 0.48 ml. (5.0 mmole) ethyl chloroformate. The mixture was stirred at −15 to −10° C. for two minutes and 0.66 g. (5.0 mmole) 3-amino-2-hydroxy-2,4-dimethylpentane was added. The mixture was allowed to warm to room temperature, stirred overnight and worked-up as described in Example 5, Part B, to obtain the diprotected dipeptide amide, R_f 0.27 (TLC, ethyl acetate/hexane, 1:1, phosphomolybdic acid spray, heat) which was used directly in the next step.

D. The product from Part C, above, in 250 ml. methanol was hydrogenated over 1.0 g. 5% Pd/C at 60 psi (17 kg./cm.²) for two hours. The catalyst was removed by filtration and the solvent evaporated in vacuo. The residue was dissolved in 10 ml. methanol and 300 ml. ethyl ether was slowly added with stirring to precipitate the title compound which was collected by filtration, and dried in vacuo to a glass, 1.02 g., M.P. sinters at ca. 110° C., 123–128 (decomp.), R_f 0.31.

Sweetness, 125 x sucrose.

The corresponding compounds of formula (I) wherein R is as above and R^a is ethyl, isopropyl or n-propyl are prepared in like manner from the appropriate starting material of formula

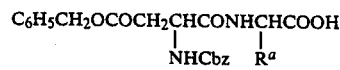

EXAMPLE 27

L-Aspartyl-D-alanine
N-(DL-2-amino-3,3-dimethyl-4-hydroxybutanoic acid lactone)amide,

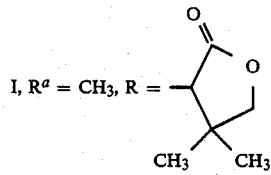

A. DL-2-Amino-3,3-dimethyl-4-hydroxybutyric acid lactone hydrochloride

Prepared by the method of Wieland, Chem. Ber., 81, 323 (1948):

2-Keto-3,3-dimethyl-4-hydroxybutyric acid lactone, 3.5 g. was neutralized with dilute sodium hydroxide and the aqueous solution evaporated to dryness in vacuo. The residue was taken up in 100 ml. warm ethanol, filtered hot and a solution of 700 mg. sodium metal in 10 ml. ethanol containing 2 g. hydroxylamine hydrochloride was added. The sodium salt of 3,3-dimethyl-4-hydroxy-2-oximinobutyric acid lactone, 5 g. precipitated and was recrystallized from methanol. The oxime was formed by decomposition of the sodium salt in 2 N hydrochloric acid, from which it slowly crystallized. After recrystallization from benzenehexane, M.P. 160° C.

A solution of 25 g. of the oxime in 100 ml. ethanol was added in portions to 5 g. platinum oxide suspended in 150 ml. 2 N hydrochloric acid and the mixture hydrogenated at atmospheric pressure for 2 days. The catalyst was filtered off, the filtrate evaporated and the residue taken up in 150 ml. ethanol. Treatment with 500 ml. ethyl ether precipitated DL-2-amino-3,3-dimethyl-4-hydroxybutyric acid lactone hydrochloride, 22 g., which was recrystallized from ethanol/ether, M.P. 208°–212° C.

B. Diblocked dipeptide amide

The aminolactone hydrochloride from Part A, 1.65 g. (0.010 mole) in 10 ml. methylene chloride and an equimolar amount of triethylamine was employed in the procedure of Example 5, Part B, to provide 2.38 g.

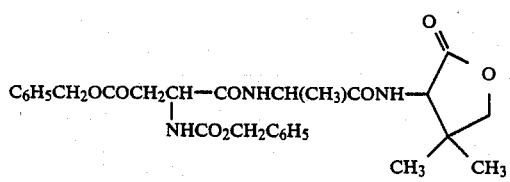

as a tacky solid, R$_f$0.26 (TLC, ethyl acetate/hexane, 7:3 by volume, phosphomolybdic acid spray).

C. The product from Part B, above, 2.38 g. was dissolved in 200 ml. methanol, 0.2 g. of 5% Pd/C catalyst added, the mixture hydrogenated and the product isolated as described in Example 5, Part C, to afford 1.3 g. of colorless solid which was washed with ethyl ether and dried, M.P.120°-130° C. (decomp.), R$_f$ 0.18. The mass spectrum and $^1$NMR data were in agreement with the structure of the title compound.

Sweetness, 110 x sucrose.

EXAMPLE 28

L-Aspartyl-D-norvaline
N-(2,2,4,4-tetramethyl-3-hydroxycyclobutyl)amide,

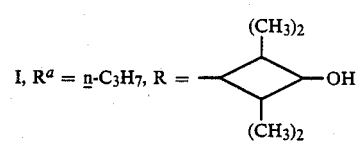

A.

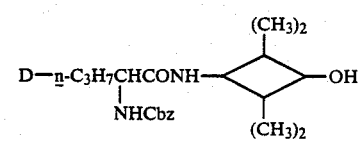

N-Benzyloxycarbonyl-D-norvaline (0.1 mole), prepared from commercial D-norvaline by the procedure of Example 19, is reacted with cis/trans 2,2,4,4-tetramethyl-3-hydroxycyclobutylamine by the method of Example 20, Part A, to provide the N-Cbz-norvaline amide.

B. Hydrogenation of N-Cbz-norvaline amide by the method of Example 20, Part B provides the corresponding 2-amino compound, D-norvaline-2,2,4,4-tetramethyl-3hydroxycyclobutylamide. The latter compound is converted to the title compound by the procedures of Example 20, Parts C and D.

The corresponding compounds of formula (I) wherein R is as defined above and R$^a$is methyl, ethyl or isopropyl are prepared in like manner from the appropriate starting N-Cbz-D-amino acid.

EXAMPLE 29

L-Aspartyl-D-norvaline
N-(2,2,4,4-tetramethyl-3-oxocyclobutyl)amide

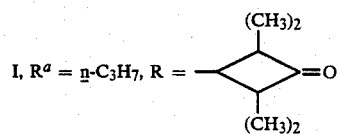

A.

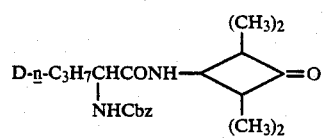

D-N-Benzyloxycarbonylnorvaline N-(2,2,4,4-tetramethyl-3-hydroxycyclobutyl)amide prepared in Example 28, Part A, 37.6 g., (0.10 mole) dissolved in 1500 ml. acetone is cooled to −10° C. under a dry nitrogen atmosphere and 42 ml. (0.11 mole) 2.67 M chromic anhydride in diluted sulfuric acid is added. After stirring for 15 minutes at −10° C., the solvent is evaporated in vacuo, the residue poured into an icewater mixture, neutralized with sodium hydroxide solution and extracted with ethyl ether. The ether extracts are dried (MgSO$_4$) and evaporated to dryness to obtain the crude product which may be purified, if desired, by column chromatography on silica gel.

B. Hydrogenation of the product of Part A, above, by the method of Example 20, Part B provides D-norvaline 2,2,4,4-tetramethyl-3-oxocyclobutylamide. This is, in turn, converted to the title compound by the methods described in Example 20, Parts C and D.

The corresponding compounds of formula

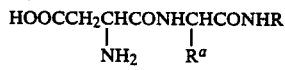

where R is as defined above and $R^a$ is $CH_3$, Et, or $(CH_2)_2CH$ are obtained in like manner.

Employing the appropriate amine of formula $RNH_2$ in the above procedures the compounds of formula (I) shown below are similarly prepared

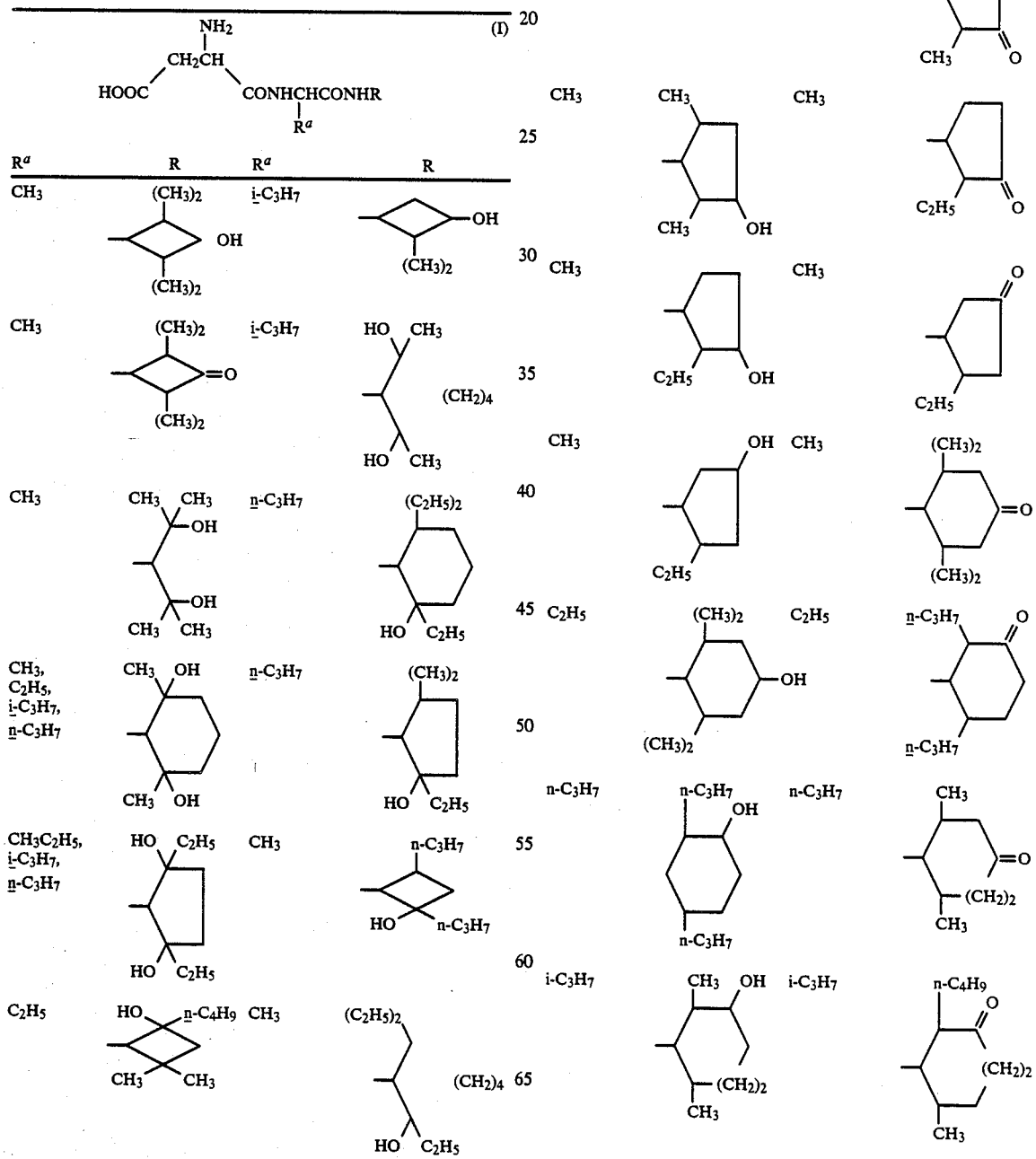

-continued $$\begin{array}{c}NH_2\\|\\CH_2\\|\\HOOC\quad\quad CONHCHCONHR\\|\\R^a\end{array}\quad(I)$$

| $R^a$ | R | $R^a$ | R |
|---|---|---|---|
| CH₃ | n-C₄H₉ 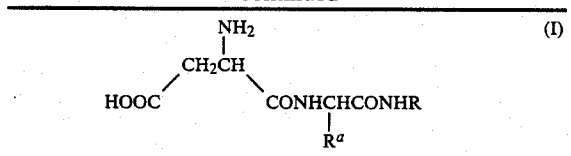 | CH₃ | n-C₄H₉ 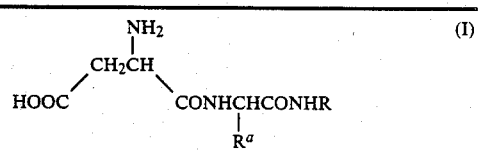 |
| CH₃ | n-C₄H₉ 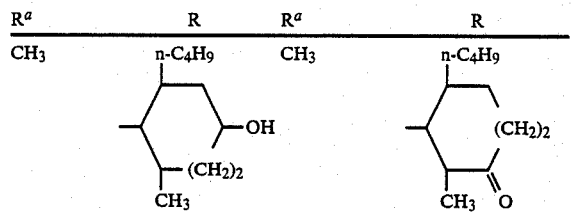 | CH₃ | 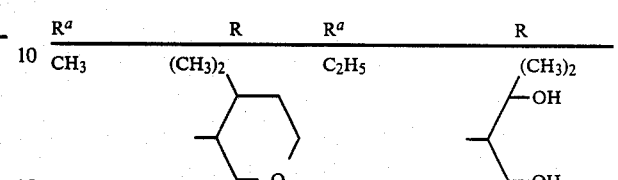 |
| CH₃ | (CH₃)₂ 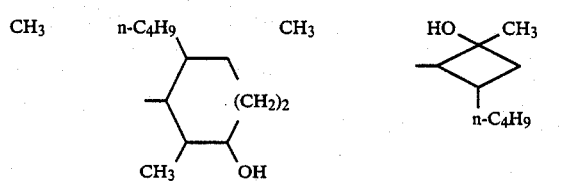 | CH₃ | 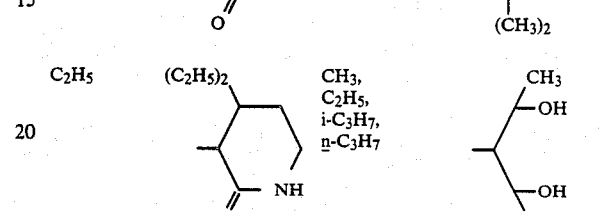 |
| CH₃ | (CH₃)₂ 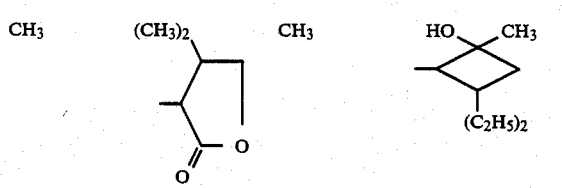 | CH₃ | 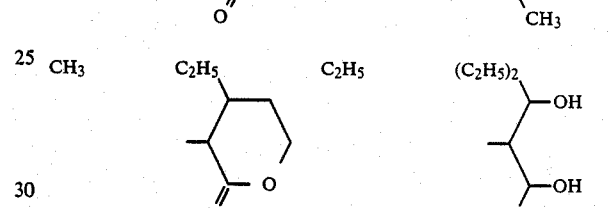 |
| CH₃ | (C₂H₅)₂ 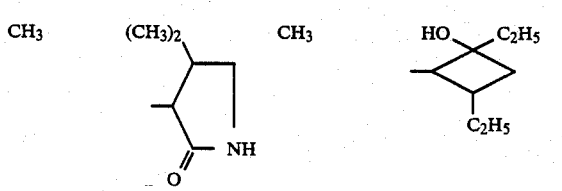 | CH₃ | 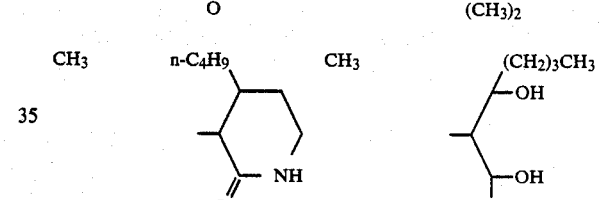 |
| CH₃ | CH₃ 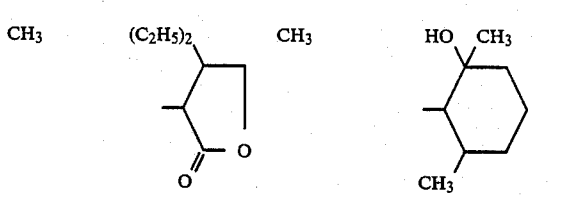 | CH₃ | 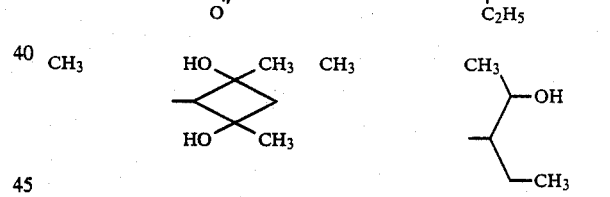 |
| C₂H₅ | n-C₃H₇ 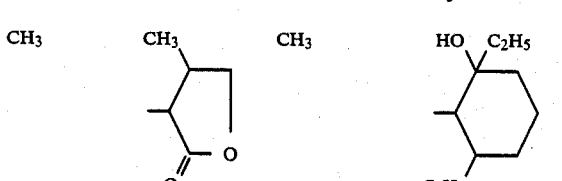 | CH₃ | 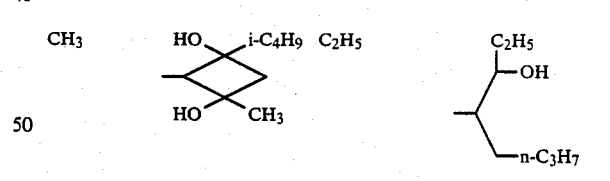 |
| C₂H₅ | t-C₄H₉ 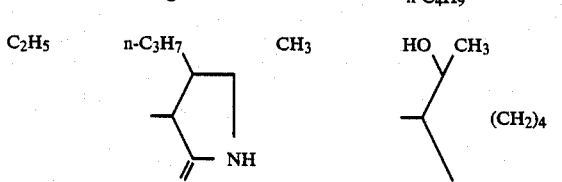 | i-C₃H₇ | 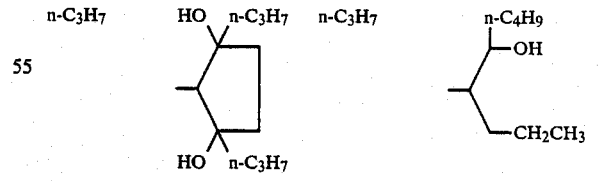 |

-continued $$\begin{array}{c}NH_2\\|\\CH_2\\|\\HOOC\quad\quad CONHCHCONHR\\|\\R^a\end{array}\quad(I)$$

| $R^a$ | R | $R^a$ | R |
|---|---|---|---|
| CH₃ | (CH₃)₂ | C₂H₅ | (CH₃)₂ — OH / —OH / (CH₃)₂ |
| C₂H₅ | (C₂H₅)₂ | CH₃, C₂H₅, i-C₃H₇, n-C₃H₇ | CH₃ — OH / —OH / CH₃ |
| CH₃ | C₂H₅ | C₂H₅ | (C₂H₅)₂ — OH / —OH / (CH₃)₂ |
| CH₃ | n-C₄H₉ | CH₃ | (CH₂)₃CH₃ — OH / —OH / C₂H₅ |
| CH₃ | | CH₃ | CH₃ — OH / CH₃ |
| CH₃ | | C₂H₅ | C₂H₅ — OH / n-C₃H₇ |
| n-C₃H₇ | | n-C₃H₇ | n-C₄H₉ — OH / CH₂CH₃ |
| CH₃ | | CH₃ | n-C₄H₉ / —OH / C₂H₅ |

-continued $$\begin{array}{c} NH_2 \\ | \\ CH_2 \\ | \\ HOOC-CH-CONHCHCONHR \\ \phantom{HOOC-CH-CONHCH}| \\ \phantom{HOOC-CH-CONHCH}R^a \end{array} \quad (I)$$

A table of substituent combinations follows, with columns $R^a$, R, $R^a$, R containing various alkyl groups (CH₃, C₂H₅, n-C₃H₇, i-C₃H₇, i-C₄H₉, n-C₄H₉) and hydroxyl/lactone-containing structures. The entries are too numerous and structurally complex to transcribe in plain markdown without loss of fidelity.

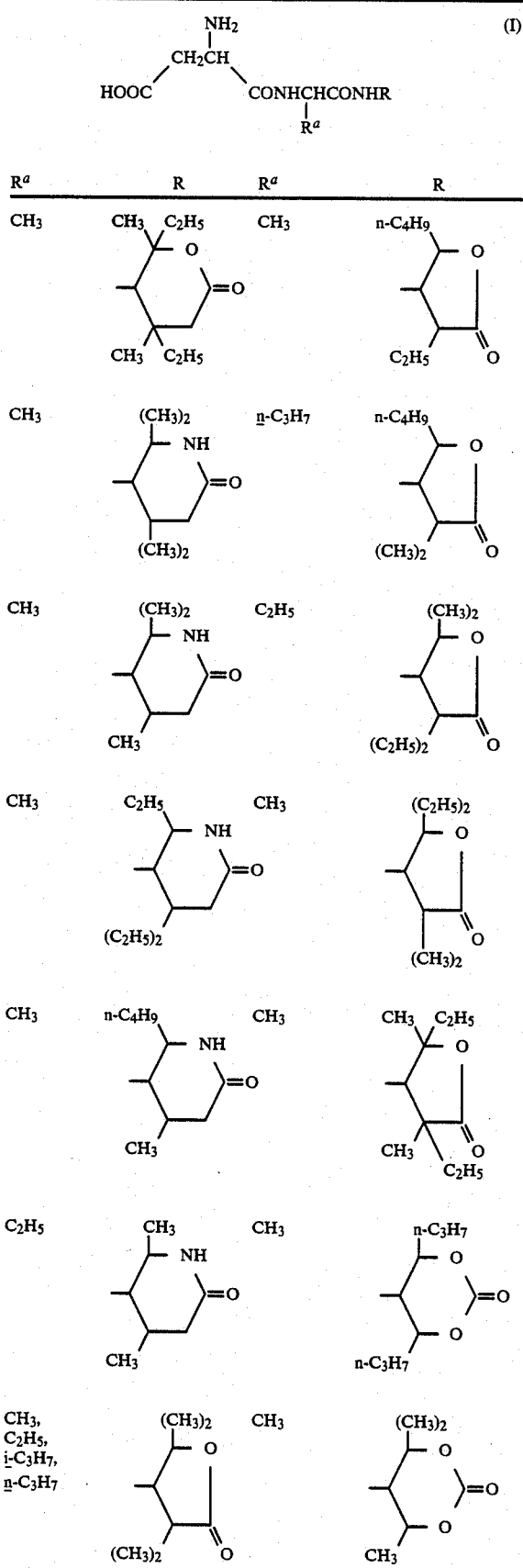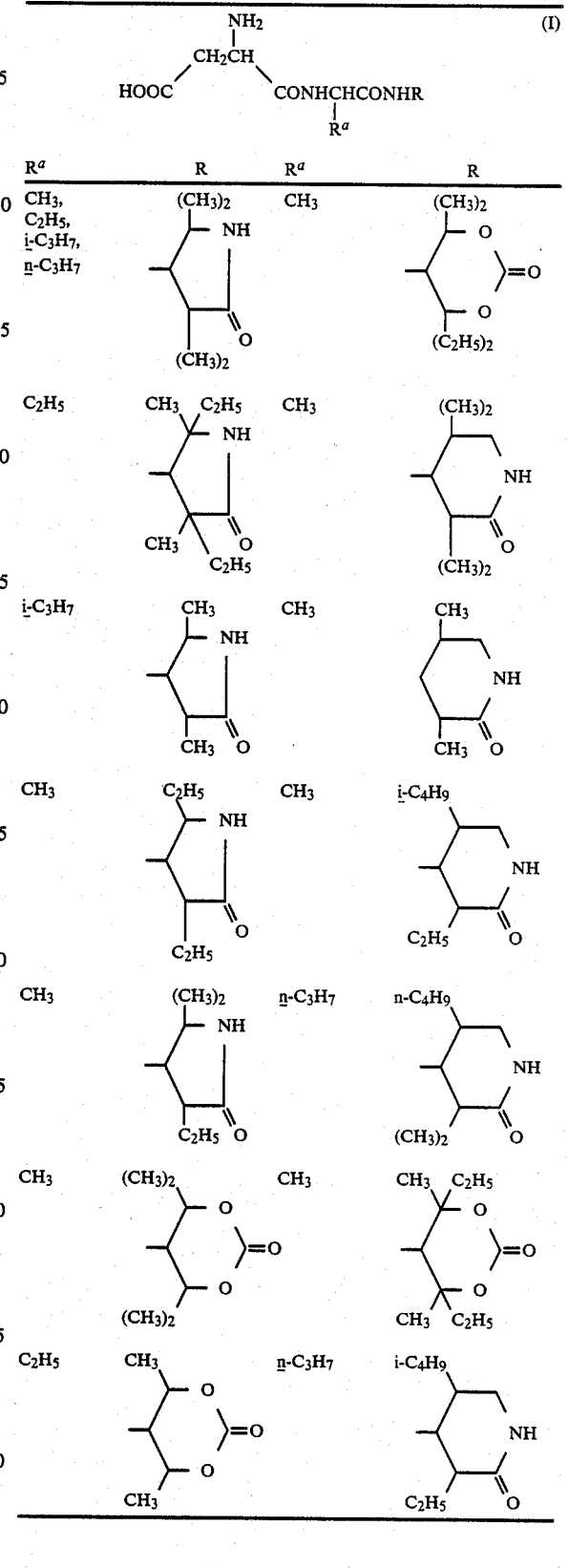
EXAMPLE 31
Mass spectrum data was obtained on the following compounds of formula (I) by solid probe introduction into a DS-50 Mass Spectrometer and exact mass of the molecular ion measured in each case to determine the elemental composition of the compounds. The molecular ion in each case was a (M+H)+ rather than M+ ion for all compounds. Fragmentation patterns were similar in each case. There were no unidentified peaks at +100 amu from the molecular ion which is an indication of chemical purity.

$$\text{HOOC-CH}_2\text{CH(NH}_2\text{)CONHCH(CH}_3\text{)CONHR}$$

(L-Asp D-ala)
(I, $R^a$ = $CH_3$)

| R | (M + H)+ Calculated | Found | Elemental Composition |
|---|---|---|---|
| cyclopropyl-cyclopropylmethyl | 298.177 | 298.176 | $C_{14}H_{24}N_3O_4$ |
| $C(CH_3)_3$-cyclopropylmethyl | 314.208 | 314.211 | $C_{15}H_{28}N_3O_4$ |
| $CH(CH_3)_2$, $CH(CH_3)_2$ | 302.208 | 302.209 | $C_{14}H_{28}N_3O_4$ |
| $CH_3$-cyclohexyl-$CH_3$ | 314.208 | 314.208 | $C_{15}H_{28}N_3O_4$ |
| $CH_3$, $CH_3$ / O / $CH_3$, $CH_3$ | 330.203 | 330.202 | $C_{15}H_{28}N_3O_5$ |
| $CH_3$, $CH_3$ / S / $CH_3$, $CH_3$ | 332.164 | 332.165 | $C_{14}H_{26}N_3O_4S$ |

EXAMPLE 32

Carbonated Cola Beverage

A carbonated cola beverage was prepared according to the composition given below. The resulting beverage was judged to have sweetness intensity comparable to a control beverage containing 11% sucrose.

| Ingredient | %, weight |
|---|---|
| Caffeine (1% aqueous solution) | 0.700 |
| L-Aspartyl-D-alanine N(cis,trans-2,6-dimethylcyclohexyl)amide (10% aqueous) | 0.180 |
| Cola flavor concentrate | 0.080 |
| Phosphoric acid (50% aqueous) | 0.040 |
| Citric acid (50% aqueous) | 0.066 |
| Sodium citrate (25% aqueous) | 0.210 |
| Caramel color (25% aqueous) | 0.370 |
| Lemon oil extract | 0.012 |
| Lime oil extract | 0.021 |
| Carbonated water (3.5 volumes carbon dioxide) | q.s. |
| | 100.000 |

Replacement of the L-aspartyl-D-alanine N-(cis,-trans-2,6-dimethylcyclohexyl)amide in the above formulation with 0.22% of 10% aqueous L-aspartyl-D-2aminobutyric acid N-(dicyclopropylcarbinyl)amide or 1.10% of 10% aqueous L-aspartyl-D-valine N-(dicyclopropylcarbinyl)amide affords carbonated cola beverages of like quality.

EXAMPLE 33

Dietetic Hard Candy

A hard candy is prepared according to the following formulation and procedure:

| Ingredients | Grams |
|---|---|
| L-Aspartyl-D-alanine N—(dicyclopropylcarbinyl)-amide | 0.35 |
| Water | 4.00 |
| FD and C Red #40 (10% aqueous) | 0.30 |
| Cherry flavor | 0.60 |
| Citric acid | 6.00 |
| Polydextrose* | 420.00 |
| Water | 180.00 |

In a small beaker dissolve the sweetener in water, add color, flavor and citric acid and mix well to dissolve. In a separate beaker combine polydextrose and water. Stir while heating to 140° C. then allow to cool to 120°-125° C. Add other ingredients from small beaker and mix or knead thoroughly. Transfer mass to an oil coated marble slab and allow to cool to 75°-80° C. Extract the mass through an oil coated impression roller.

Use of 0.42 g. of L-aspartyl-D-alanine N-(2,2,4,4-tetramethyl-1,1-dioxothietan-3-yl)amide or 0.93 g. of L-aspartyl-D-alanine N-(2,2,4,4-tetramethyl-3-pentyl)amide as sweetening agent in place of L-aspartyl-D-alanine N-(dicyclopropylcarbinyl)amide affords similar results.

EXAMPLE 34

A gelatin dessert is prepared according to the following composition and procedure.

| Ingredients | Grams |
|---|---|
| Gelatin 225 Bloom | 7.522 |
| Citric acid | 1.848 |
| Sodium citrate | 1.296 |
| Strawberry flavor | 0.298 |
| L-Aspartyl-D-alanine N—(dicyclopropylcarbinyl)-amide | 0.036 |
| Boiling water | 240.000 |
| Cold water | 240.000 |
| | 491.000 |

Premix the first five ingredients, add to boiling water and stir to dissolve completely. Add cold water and stir briskly. Transfer to serving dishes and refrigerate until set.

EXAMPLE 35

Low calorie table sweeteners are prepared according to the following formulations:

A. A powder form of sweetener is prepared by blending the following ingredients.

| Ingredients | %, weight |
| --- | --- |
| L-Aspartyl-D-alanine N—(2,2,4,4-tetramethyl-thietan-3-yl)amide | 0.18 |
| Crystalline sorbitol | 49.76 |
| Dextrin (dextrose equivalent 10) | 50.00 |
| Monosodium glutamate | 0.02 |
| Glucono-delta-lactone | 0.02 |
| Sodium citrate | 0.02 |
| | 100.00 |

One gram of the resulting blend is equivalent in sweetness to about three grams of sucrose.

B. A table sweetener in liquid form is prepared as follows.

| Ingredients | %, weight |
| --- | --- |
| L-Aspartyl-D-alanine N—(dicyclopropylcarinyl)-amide | 0.10 |
| Water | 99.80 |
| Sodium benzoate | 0.10 |
| | 100.00 |

One gram of the resulting solution is equivalent in sweetness to about 1.2 grams of crystalline sucrose.

When the sweetener of formula (I) employed in part A, above, is 0.59 g. of a 1:4 mixture of L-aspartyl-D-alanine N-(dicyclopropylcarbinyl)amide and sodium saccharin comparable results are obtained. Similarly when the L-aspartyl-D-alanine N-(dicyclopropylcarbinyl)amide employed in Part B, above, is replaced by 0.20 g. of a 1:6 by weight mixture of the same compound and sodium saccharin a comparable liquid table sweetener is obtained.

EXAMPLE 36

Frozen Dessert

A vanilla sugarless frozen dessert is prepared according to the following formulation by conventional practice.

| Ingredients | %, weight |
| --- | --- |
| Heavy cream (35% butterfat) | 23.00 |
| Nonfat milk solids | 10.50 |
| Mono- and diglyceride emulsifier | 0.25 |
| Polydextrose* | 11.20 |
| Water | 54.51 |
| L-Aspartyl-D-alanine N—(2,2,6,6-tetramethyl-cyclohexyl)amide | 0.04 |
| Gelatin (225 Bloom) | 0.50 |
| | 100.00 |

*U.S. 3,766,165

EXAMPLE 37

Canned Pears

Fresh pears are washed, peeled, cored, sliced into pieces and immersed in an aqueous solution containing 0.05% by weight of ascorbic acid. The sliced fruit is packed into screw-cap jars and the jars filled with a syrup containing the following ingredients:

| | %, weight |
| --- | --- |
| Sorbitol | 25.000 |
| L-Aspartyl-D-alanine N—dicyclopropylcarbinyl)-amide | 0.025 |
| Citric acid | 0.125 |
| Water | q.s. |
| | 100.000 |

The jars are capped loosely and placed in an autoclave containing hot water and processed at 100° C. for 45 minutes. The jars are removed, immediately sealed by tightening the caps and allowed to cool.

EXAMPLE 38

Powder Beverage Concentrate

| Ingredients | %, Weight |
| --- | --- |
| Citric acid | 31.78 |
| Sodium citrate | 5.08 |
| Strawberry flavor | 57.72 |
| Strawberry FD and C color | 0.54 |
| L-Aspartyl-D-alanine N—[(−)fenchyl]amide | 2.44 |
| Carboxymethyl cellulose | 2.44 |
| | 100.00 |

Combine all ingredients in a blender and blend until homogenous. For use, 1.73 g. of powder beverage concentrate is dissolved in 4 fluid ounces (118 ml.) of water.

EXAMPLE 39

Baked Cake

A highly acceptable vanilla cake was prepared employing the following recipe:

| Ingredients | Grams |
| --- | --- |
| Emulsified shortening | 16.09 |
| Water | 20.83 |
| Eggs | 23.00 |
| Sodium bicarbonate | 1.10 |
| Vanilla extract, single fold | 0.28 |
| Glucono-delta-lactone | 1.75 |
| Polydextrose*, 70% aqueous solution | 80.00 |
| Nonfat dry milk | 2.50 |
| Cake flour | 56.20 |
| Whole milk powder | 0.80 |
| Wheat starch | 1.40 |
| L-Aspartyl-D-alanine N—(dicyclopropylcarbinyl)-amide | 0.05 |
| | 204.00 |

Combine nonfat dry milk, whole milk powder, polydextrose solution and emulsified shortening. Mix at low speed until creamy and smooth (about 3 minutes), add eggs and beat until a homogenous creamy mix is obtained. Dissolve sweetener in water, add to creamy homogenate and mix 2–3 minutes. Add remaining ingredients and mix until creamy and smooth (3–5 minutes). Place 120 g. of batter in small pregreased pan and bake at 350° F. (176° C.) for 30 minutes.

EXAMPLE 40

Synergistic Mixtures of L-Aspartyl-D-alanine N-(dicyclopropylcarbinyl)amide, [I, $R^a$=CH$_3$, R=CH($\Delta_2$] and saccharin Blends of [I, $R^a$=CH$_3$, R=CH($\Delta$)$_2$] and sodium saccharin were prepared and evaluated for taste acceptability and sweetness intensisty by comparison with aqueous sucrose standards. Sweetness potency factors of sodium saccharin and [I, $R^a=CH_3$, $R=CH(\Delta)_2$] of 300 and 1200 x sucrose, respectively, were used to calculate the theoretical sweetness of the blends. A series of taste panel evaluations were carried blends with sucrose solutions ranging 6 to 12% (w/v) and 0.033% sodium saccharin solution. Results are tabulated below.

| Blend, Parts by Weight | | Sweetness | | | |
|---|---|---|---|---|---|
| [I, $R^a = CH_3$ $R = CH(\Delta)_2$] | Sodium Saccharin | Potency × Sucrose | | % Synergy | Taste Quality |
| | | (T) Theory | (A) Actual | | |
| 1 : 1 | | 750 | 1000 | 33 | clean, sweet, not bitter |
| 1 : 2 | | 600 | 800 | 33 | same |
| 1 : 4 | | 480 | 600 | 33 | same |
| 1 : 6 | | 430 | 575 | 33 | sweet, perceptible bitterness |
| 1 : 8 | | 400 | 530 | 33 | sweet, slight bitterness |
| 1 : 9 | | 390 | 500 | 33 | same |
| 1 : 10 | | 381 | 475 | 25 | sweet, slight to moderate bitter, metallic taste |

The % synergy was calculated according to the following formula $$\% \text{ Synergy} = \frac{A - T}{T} \times 100$$

where A is the actual sweetness determined by averaging the taste panel results and T is the theoretical sweetness determined from the composition of the mixtures by weight e.g., for the 1:4 blend the theoretical sweetness is $(1/5 \times 1200) + (4/5 \times 300) = 480$.

From the results it is seen that with mixtures of from 1:1 to 1:9 there is an unexpected increase in sweetness potency of 33% and a somewhat lesser synergistic effect with the 1:10 blend. Furthermore there is complete masking of the well known bitter aftertaste of saccharin with blends of from 1:1 to 1:4 and effective masking of bitterness in blends containing up to one part L-aspartyl-D-alanine N(dicyclopropylcarbinyl)amide and 9 parts sodium saccharin.

When the above procedure is repeated but the invention compound is employed is of the formula (I) wherein $R^a$ is methyl and R is

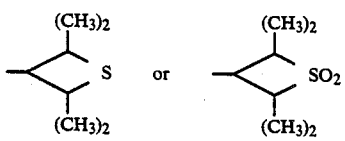

similar results are obtained.

EXAMPLE 41

Three batches of carbonated cola beverages were prepared according to the method of Example 32 except that the sweetener employed in batch A was 0.020 g. of the 1:6 blend of [I, $R^a=CH_3$, $R=CH(\Delta)_2$]/sodium saccharin, batch B employed 12 g. sucrose and batch C, 0.3412 g. of a 1:10 blend of saccharin/cyclamate. The sweetness factor employed for the [I, $R^a=CH_3$, $R=CH(\Delta)_2$]/sodium saccharin blend was that determined in Example 40, i.e. 575 x sucrose. The three beverages were rated for hedonic scores on a nine point rating scale* by a taste panel with the following results.

| Beverage | Average of Hedonic Scores |
|---|---|
| A | 7.1 |
| B | 8.0 |
| C | 6.7 |

*1 =Dislike extremely, 5 =neither like nor dislike, 9=like extremely.

Similarly, when the same three sweeteners are employed in like manner in carbonated lemon-lime beverage, instant chocolate pudding, marshmallow, grape jelly, orange flavored gelatin, gum drops, chewing gum or vanilla cake formulations, comparable results are obtained.

EXAMPLE 42

Sodium Salt of L-Aspartyl-D-alanine

N-(dicyclopropylcarbinyl)amide

To a solution of 3 g. (0.01 mole) L-aspartyl-Dalanine N-(dicyclopropylcarbinyl)amide in 100 ml. of ethanol is added 2 ml. of 5N sodium hydroxide. The resulting mixture is stirred for ten minutes at room temperature then evaporated to dryness in vacuo. The residue is triturated with anhydrous ethanol, filtered and air dried.

When the sodium hydroxide employed above is replaced with an equivalent amount of potassium hydroxide, calcium hydroxide, magnesium hydroxide or ammonium hydroxide the corresponding potassium, calcium, magnesium and ammonium salts are formed in like manner.

The remaining L-aspartyl-amino acid dipeptide amides of formula (I) are also converted to carboxylate salts as described above.

EXAMPLE 43

Acid Addition Salts

The L-aspartyl-D-amino acid dipeptide amide of formula (I) is slurried in a small amount of water and an equivalent amount of acids such as hydrochloric, phosphoric, sulfuric, acetic, maleic, fumaric, lactic, tartaric, citric, gluconic or saccharic acid is added. The resulting mixture is stirred for 15–30 minutes then evaporated to dryness or precipitated by addition of a cosolvent such as methanol or ethanol.

EXAMPLE 44

Comparative stability of representative L-aspartyl-D-alanine amides of the invention was determined at pH 7 and pH 3 in 0.01M phosphate buffer at 90° C. The concentration of unchanged sweetener was determined at 24 hour intervals by high pressure liquid chromatography on a 10 cm. Lichrosorb* $C_{18}$ column at 1 ml. per minute of 0.01 M ammonium acetate containing 15% methanol by volume. The halflife at 90° C. calculated for each of the compounds of formula (I) at pH 7 and pH 3 is shown in the table below. ≠*Registered Trademark

| Compound of Formula (I, $R^a$ = $CH_3$) R | Half-life at 90° C., Hours | |
|---|---|---|
| | pH 7 | pH 3 |
| $(CH_3)_2CH$—CH—$CH(CH_3)_2$ | 54.6 | 21.2 |
| cyclopropyl—CH—$C(CH_3)_3$ | 51.5 | 20.2 |
| 2,2,5,5-tetramethylcyclopentyl | 49.3 | 19.6 |
| dicyclopropylmethyl | 57.8 | 18.8 |

From data obtained in a similar manner, but at various other temperatures, the half-life of the invention compounds at room temperature is estimated to be ten years or more at these pH's.

EXAMPLE 45

2-Alkyl- and 2,6-Dialkylcyclohexylamines

To a solution of 25 g. of 2,6-diisopropylaniline in 250 ml. each of ethanol and water was added 10 g. of dry 5% ruthenium-on-carbon catalyst. The mixture was hydrogenated in an autoclave at 100° C., 1000 psi (70.4 kg./cm.²) until hydrogen uptake ceased. The catalyst was removed by filtration and the filtrate evaporated to remove solvent. The residue was distilled in vacuo tooobtain 11.2 g. of 2,6-diisopropylcyclohexylamine as a mixture of cis,trans and trahs,transisomers, B.P. 122°–124° C. at 22 mm.

By employing the appropriate 2-alkylaniline or 2,6-dialkylaniline as starting material and hydrogenating by the above method the following cyclohexylamines are also obtained.

2-methyl-6-ethylcyclohexylamine, B.P. 82°–87° C. at 19 mm. (50% yield);
2-methyl-6-isopropylcyclohexylamine, B.P. 86° at 14 mm. (45% yield);
2-n-butylcyclohexylamine;
-ethyl-6-n-butylcyclohexylamine;
-methyl-6-t-butylcyclohexylamine;
-t-butylcyclohexylamine;
,6-dimethylcyclohexylamine;
trans-2-ethylcyclohexylamine, B.P. 77°–78° (23 mm.);
,6-diethylcyclohexylamine, B.P. 96° C., (17 mm.);
trans-2,-isopropylcyclohexylamine;
-isobutylcyclohexylamine;
-methyl-6-n-butylcyclohexylamine.

EXAMPLE 46

2-t-Butylcyclohexylamine i. 2-t-Butylcyclohexanone

A solution of 31.25 g. (0.20 mole) t-butylcyclohexanol in 80 ml. of ethyl ether was cooled to 10° C. To this was added dropwise, with stirring, a solution of 21.0 g. (0.07 mole) sodium dichromate dihydrate and 15.75 ml. (0.30 mole) concentrated sulfuric acid in 100 ml. water while maintaining the reaction mixture below 25° C. The mixture was then warmed to room temperature, stirred for two hours, poured onto icewater, ether layer separated, the aqueous phase extracted again with ether and the combined extracts washed with water, sodium bicarbonate and dried ($MgSO_4$). Evaporation of the ether afforded 30.6 g. (99%) of the desired ketone.

ii. Leuckart Reduction of Ketone

A mixture of 2-t-butylcyclohexanone 30.6 g. (0.20 mole), formamide 50 ml. (1.2 mole) and formic acid (10 ml.) was heated at reflux while removing water as it formed in the reaction while returning the ketone to the reaction vessel. Formic acid (10 ml.) was added as needed to control deposition of ammonium carbonate in the condenser. After four hours the reaction temperature reached 197° C. and distillation ceased. The mixture was cooled, diluted with water (50 ml.) and extracted with ethyl acetate (75 ml.). The organic layer was evaporated, concentrated hydrochloric acid added (50 ml. per 100 ml. of residue), the mixture boiled overnight, cooled and washed with 50 ml. of ethyl ether. The aqueous phase was adjusted to pH 11 with sodium hydroxide, cooled, extracted with ether (2×40 ml.) and the extracts dried over sodium hydroxide pellets. The solvent was evaporated and the residue distilled through a 10 cm. column to obtain 21.93 g. of the title amine (71%), B.P. 86°–88° C. (21 mm.) as a mixture of cis and trahs-isomers.

iii. dl-Fenchone and l-fenchone are reduced to the corresponding fenchylamines by the Leuckart reduction method of Part ii, above. (-)Fencylamine is obtained as a water white liquid, B.P. 55°–60° C. (6 mm.), $[alpha]_D$ −21.9° in 30% yield.

EXAMPLE 47

Alkylcycloalkylcarbinylamines and dicycloalkylcarbinylamines i. To a mixture of 118.5 g. (1.0 mole) of cyclobutylcarbonyl chloride and 99 g. (1.0 mole) cuprous chloride in 1000 ml. of dry ether under a nitrogen atmosphere is added dropwise 478 ml. (1.0 mole) of 2M t-butylmagnesium chloride in the same solvent. The addition is carried out at −5° to −15° C. The resulting mixture is poured into 500 ml. of 3M hydrochloric acid and 700 g. ice, the organic layer is separated and washed successively with water, sodium bicarbonate solution, brine and dried (MgSO$_4$). The dried ether extract is evaporated at reduced pressure and the residue distilled to provide t-butylcyclobutylketone.

ii. The ketone, 105 g. (0.75 mole), is mixed with hydroxylamine hydrochloride 38.3 g. (1.16 mole) and sodium acetate, 123 g. (1.50 mole), in sufficient water to effect solution, heated on the steam-bath for one hour, cooled and the mixture adjusted toppH 7.5 with sodium hydroxide solution. After extracting the mixture with ether, the extracts are dried (MgSO$_4$) and evaporated to dryness to afford the oxime. The oxime is dissolved in anhydrous ethanol (about two liters per mole of oxime) and the solution heated at reflux. Sodium metal (about 10 moles per mole of oxime) is added in portions at a rate sufficient to maintain reflux temperature. When all the sodium is added the resulting mixture is cooled and 200 ml. of ethanol followed by 300 ml of water is added. The mixture is acidified with hydrochloric acid, evaporated to remove ethanol and the residue made alkaline (pH 12-13) with 10M sodium hydroxide. The alkaline mixture is extracted several times with ether and the combined extracts dried (MgSO$_4$). Dry hydrogen chlorine is passed through the dried extracts until precipitation is complete. The precipitated hydrochloride salt is collected by filtration, washed with ether and air dried. The salt is converted to the free base by means of aqueous sodium hydroxide, extraction with ethyl ether and evaporation of the extracts. The product, t-butylcyclobutylcarbinylamine is of suitable purity for use in preparing the amides of the invention but may be further purified, if desired, e.g. by distillation or column chromatography.

iii. By employing the appropriate acid halide and Grignard reagent in the abve procedure in place of cyclobutylcarbonyl chloride and t-butylmagnesium chloride the following amines are obtained in like manner.

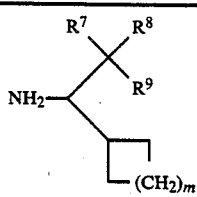

| m | R$^7$ | R$^8$ | R$^9$ |
|---|---|---|---|
| 0 | H | H | H |
| 0 | CH$_3$ | H | H |
| 0 | CH$_3$ | CH$_3$ | H |
| 0 | CH$_3$CH$_2$ | CH$_3$CH$_2$ | CH$_3$CH$_2$ |
| 0 | CH$_3$ | n-C$_4$H$_7$ | H |
| 0 | (CH$_3$)$_2$CH | (CH$_3$)$_2$CH | H |
| 0 | CH$_3$ | CH$_3$ | C(CH$_3$)$_3$ |
| 1 | CH$_3$CH$_2$ | CH$_3$CH$_2$ | H |
| 1 | n-C$_3$H$_7$ | H | H |
| 1 | CH$_3$ | CH$_3$ | H |
| 1 | CH$_3$ | n-C$_4$H$_7$ | H |
| 1 | n-C$_3$H$_7$ | n-C$_3$H$_7$ | H |
| 1 | CH$_3$CH$_2$ | (CH$_3$)$_3$C | H |
| 2 | CH$_3$ | CH$_3$ | CH$_3$* |
| 2 | CH$_3$CH$_2$ | H | H |
| 2 | CH$_3$CH$_2$ | CH$_3$CH$_2$ | CH$_3$CH$_2$ |
| 2 | CH$_3$ | H | H |
| 2 | CH$_3$ | CH$_3$ | H |

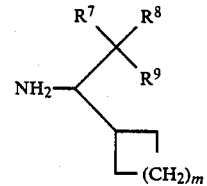

| m | R$^7$ | R$^8$ | R$^9$ |
|---|---|---|---|
| 2 | n-C$_3$H$_7$ | (CH$_3$)$_2$CH | H |
| 2 | CH$_3$CH$_2$ | n-C$_4$H$_7$ | H |
| 3 | CH$_3$ | CH$_3$ | CH$_3$ |
| 3 | n-C$_3$H$_7$ | H | H |
| 3 | CH$_3$ | CH$_3$ | H |
| 4 | CH$_3$ | H | H |
| 4 | CH$_3$ | CH$_3$ | CH$_3$ |
| 4 | CH$_3$CH$_2$ | CH$_3$CH$_2$ | H |

*B.P. 80–90° C. (21 mm.)

iv. The amines of the following formula are also provided in like manner.

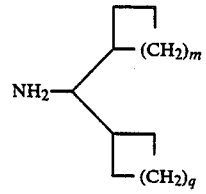

| m | q |
|---|---|
| 0 | 1 |
| 0 | 2 |
| 0 | 3 |
| 0 | 4 |
| 1 | 1 |
| 1 | 2 |
| 1 | 3 |
| 1 | 4 |
| 2 | 2 |
| 2 | 3 |
| 2 | 4 |
| 3 | 3 |
| 3 | 4 |
| 4 | 4 |

The following amines are also prepared by this method:
2,2-dimethyl-3-aminopentane, B.P. 123°–126° C., atmospheric pressure;
2,2,4-trimethyl-3-aminopentane, B.P. 149°–150° C., atmospheric pressure.

EXAMPLE 48 trans-2-Ethylcyclopentylamine i. 2-Ethylcyclopentanone

In a three-necked flask 5.0 g. of sodium metal was dissolved in 250 ml. of dry ethanol and 31.24 g. (0.20 mole) 2-carboethoxycyclopentanone added. To the resulting yellow solution 18.4 ml. (0.23 mole) ethyl iodide was added dropwise and the mixture heated at reflux for two hours. After cooling, 250 ml. of brine and 50 ml. of water were added and the mixture extracted with ethyl ether (2×100 ml.). After drying (MgSO$_4$) and evaporation of solvent 36.5 g. (99%) of 2-ethyl-2carboethoxycyclopentanone was obtained.

This was decarboxylated by heating at reflux with a mixture of 200 ml. of concentrated hydrochloric acid and 100 ml. of water. After four hours at reflux carbon dioxide evolution was complete. The mixture was cooled, saturated with sodium chloride, extracted with ethyl ether, the extracts dried (MgSO4) and ether evaporated. The residue was distilled to obtain 12.62 g. (56%) of 2-ethylcyclopentanone, B.P. 97°–98° C. (100 mm.).

ii. The product obtained above was converted to trans-2-ethylcyclopentylamine by the procedure of Example 47, Part ii, B.P. 150°–151° C. in 35% yield. The identity of the product was verified by its $^1$H-NMR spectrum.

By employing the appropriate 2-carbethoxycycloalkanone or a corresponding heterocyclic ketone (prepared by the well known Dieckmann cyclization of the appropriate dicarboxylate ester, see e.g., H. O. House, "Modern Synthetic Reactions", W. A. Benjamin, Menlo Park, Cal., 1972, p. 740.) and the appropriate alkyl halide in place of ethyl iodide in the above procedure the following amines of formula R NH2 are prepared in like manner.

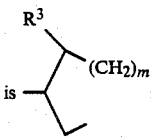

Where R is —

| m | R$^3$ |
|---|---|
| 1 | CH$_3$ |
| 1 | C$_2$H$_5$ |
| 2 | t-C$_4$H$_9$ |
| 2 | CH$_3$ |
| 2 | sec-C$_4$H$_9$ |
| 4 | CH$_3$ |
| 4 | t-C$_4$H$_9$ |

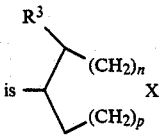

Where R is —

| X | n | p | R$_3$ |
|---|---|---|---|
| O | 1 | 0 | 2-CH$_3$ |
| O | 1 | 0 | 4-CH$_3$ |
| O | 1 | 0 | 2-t-C$_4$H$_9$ |
| O | 0 | 2 | 2-CH$_3$ |
| O | 0 | 2 | 4-CH$_3$ |
| O | 0 | 2 | 4-sec-C$_4$H$_9$ |
| O | 0 | 2 | 2-i-C$_3$H$_7$ |
| O | 0 | 3 | 2-CH$_3$ |
| O | 0 | 3 | 4-CH$_3$ |
| O | 1 | 2 | 3-CH$_3$ |
| O | 1 | 2 | 5-CH$_3$ |
| O | 1 | 2 | 5-t-C$_4$H$_9$ |
| O | 1 | 2 | 3-t-C$_4$H$_9$ |
| S | 0 | 1 | 2-CH$_3$ |
| S | 0 | 1 | 4-CH$_3$ |
| S | 1 | 1 | i-C$_3$H$_7$ |
| SO$_2$ | 1 | 1 | t-C$_4$H$_9$ |
| S | 0 | 2 | 2-CH$_3$ |
| S | 0 | 3 | 2-CH$_3$ |
| S | 0 | 3 | 4-CH$_3$ |

EXAMPLE 49 trans-2-Isopropylcyclopantylamine i. 2-Isopropylcyclopentanone

To a solution of 10 g. of sodium metal in 670 ml. of ethanol was added dropwise a mixture of 100 g. (1.19 mole) cyclopentanone and 60 g. (1.03 mole) acetone and the resulting mixture refluxed for 1.5 hours. The solvent was evaporated in vacuo, the residue taken up in ether, the solution washed with 3M hydrochloric acid (5×200 ml.), 5% sodium bicarbonate (3×200 ml.), brine (1×200 ml.) and dried (MgSO4). The ether was evaporated with mild heating to afford 97 g. of dark liquid which was distilled in vacuo to obtain 55 g. of 2-isopropylidenecyclopentanone, B.P. 96°–100° (2.7 mm.).

To 12.75 g. of the above product in 250 ml. of methanol was added 2.0 g. 5% palladium-on-carbon catalyst and the mixture hydrogenated at 50 psi (3.5 kg./cm$^2$). After one hour the hydrogen uptake was complete. The catalyst was removed and solvent evaporated in vacuo to afford 12.75 g. of colorless liquid. This was distilled to obtain 9.64 g. of 2-isopropylcyclopentanone, B.P. 74°–76° C. (20 mm.).

Reduction of 2-isopropylcyclopentanone by the method of Example 47, Part ii afforded the corresponding amine, B.P. 167° (atm.) in 31% yield.

EXAMPLE 50

2,2-Dimethyl-3-aminobutane

In a 500 ml. flask was placed 10.0 g. (0.10 mole) 2,2-dimethyl-3-butanone, 250 ml. methanol, 76.94 g. (1.0 mole) ammonium acetate and 4.37 g. (0.07 mole) sodium cyanoborohydride, and the mixture was allowed to stir at room temperature for 24 hours. The pH was adjusted to 2.0 with concentrated hydrochloric acid and the methanol removed at reduced pressure. The residual solid was dissolved in 500 ml. water and washed with three 100 ml. portions of ether. The pH of the aqueous solution was adjusted to 13 with 10M sodium hydroxide and the mixture extracted with three 100 ml. portions of ether. The extracts were combined, dried over anhydrous MgSO4, filtered and distilled. The amine (2.4 g.) distilled at 102°–103° C. at atmospheric pressure.

The racemic amine was resolved by the Polarimetric Control method described by Bruck et al., J. Chem. Soc., 921 (1956) employing the amine hydrogen tartarates and crystallizing from 70:30 methanol/water (by volume) to obtain dextrorotatory amine of 93±4% purity and levorotatory amine of 80±4% purity.

When an equivalent amount of 2,2-dimethyl-3-pentanone is employed in place of 2,2-dimethyl-3-butanone in the above procedure 2,2-dimethyl-3-amino pentane is obtained and resolved into its enantiomers.

PREPARATION A

L-Aspartic acid N-thiocarbokyanhydride

A. L-Aspartic acid (582 g., 4.29 mole) was added gradually with stirring to 350.9 g. (8.58 mole) of 50% sodium hydroxide solution at 0° C. Methyl methyl xanthate (550 g., 4.51 mole) in 405 ml. of methanol was then added as rapidly as possible. The mixture was heated at 45° C. for 1.5 hours, cooled to room temperature, and washed with two portions of methylene chloride. The methylene chloride washes were discarded and the aqueous phase acidified with concentrated hydrochloric acid at 0° C. The solution was extracted with three portions of ethyl acetate, and the combined extracts washed with brine and dried over anhydrous magnesium sulfate. The solvent was evaporated in vacuo to give a yellow oil which crystallized upon addition of ethylene dichloride and n-hexane. The N-methoxy-thiocarbonyl-L-aspartic acid was collected by filtration, washed with fresh n-hexane, and dried (420 g., 47%).

M.P. 128°–130° C.; $^1$H-NMR (DMSO-d$_6$), (delta) 2.73 (d, 2H, J=6 Hz), 3.63 (s, 3H), 4.43 (dt, 1H, J=6 Hz, 8 Hz), 6.63 (d, 1H, J=8 Hz); infrared spectrum (KBr) 1715, 1515 cm$^{-1}$.

B. N-methoxythiocarbonyl-L-aspartic acid (207.0 g., 1.00 mole) was dissolved in 1200 ml. ethyl acetate at 0° C. and phosphorous tribromide (47 ml., 0.50 mole) was added in one portion. The cooling bath was removed and the temperature allowed to rise spontaneously to 35° C. The solution was stirred for 10 minutes after which time a granular white precipitate had formed. The reaction mixture was cooled to 0°–5° C., the product collected by filtration, washed with a small volume of ether, and dried. The yield of analytically pure L-aspartic acid N-thiocarboxyanhydride was 157.4 g. (90%).

M.P. 200°–205° C. (dec.); [alpha]$_D^{25}$ = −109.5° (C=1, THF); infrared spectrum (KBr) 3225, 1739, 1724, 1653, 1399 cm$^{-1}$; $^1$H-NMR (DMSO-d ) ppm (delta) 2.83 (d, 2H, J=5.0 Hz), 4.70 (t, 1H, J=5.0 Hz), 9.23 (bs, 2H, ex); mass spectrum (m/e) 175 (M+), 87, 60.

PREPARATION B

2,2-Dimethylcyclohexylamine i. 2,2-Dimethylcyclohexanone

To a suspension of 13.5 g. (0.25 mole) sodium methoxide in 500 ml. of ethyl ether was added 30.8 g. (0.28 mole) 2-methylcyclohexanone and 20.3 g. (0.28 mole) ethyl formate. The mixture was stirred at room temperature for 12 hours, filtered under a nitrogen atmosphere, the solids washed with ethyl ether and dried in the vacuum oven at 75° C. The dried cake was ground in a mortar and pestle to a fine powder to obtain 17.5 g. (43%) of sodium 2-formyl-6-methylcyclohexanone which was used in the next step.

The above product, 17.5 g. (0.11 mole) was added to a mixture of 2.88 g. (0.13 mole) sodium shot, 500 ml. anhydrous ammonia and about 0.1 g. ferric chloride. The resulting gray suspension was cooled to −45° C. and stirred for one hour at the reflux temperature of the system. To this was added 20.86 g. (0.15 mole) methyl iodide, the mixture stirred three hours at reflux and allowed to evaporate while warming to room temperature overnight. The residue was suspended in 300 ml. ethyl ether, refluxed to expell traces of ammonia and water added to dissolve the solids. The ether was extracted with water (3×100 ml.), the combined aqueous layers treated with 6 g. of solid sodium hydroxide and heated to steam distill the ketone. The steam distillate was extracted with ethyl ether, the extracts washed with brine, dried and ether evaporated to provide 2,2dimethylcyclohexanone as a colorless liquid, 2.0 g.

ii. The ketone provided above is converted to the oxime and the latter reduced with sodium in ethanol as described in Example 47, Part ii, to provide 3.1 g. of 2,2-dimethylcyclohexylamine.

The following 2,2-disubstitutei ketones are prepared and converted to amines by the above method in like manner.

2,2-dimethylcyclopentanone
2,2-diethylcyclopentanone
2,2-di-n-propylcyclopentanone
2,2-diethylcyclohexylamine
3,3-dimethylthiepane-4-one
3,3-dimethyloxepane-4-one
4,4-dimethyloxepane-5-one

PREPARATION C

2,2,6,6-Tetramethylcyclohexylamine i. 2,2,6,6-Tetramethylcyclohexanohe

A 50% suspension of sodium hydride in mineral oil, 14.3 g. (0.30 mole), was suspended in tetrahydrofuran, the liquid decanted and the solid resuspended and decanted again to remove the oil. Then 15 g. (0.12 mole) of 2,6-dimethylcyclohexanone was added followed by dropwise addition of a mixture of 11 g. t-butanol and 20 ml. of tetrahydrofuran (vigorous hydrogen evolution) and the resulting mixture refluxed until hydrogen evolution was complete. To this was added dropwise 37.8 g. (0.30 mole) methylsulfate and the mixture heated at reflux for 24 hours. After dilution with water, extraction with ethyl ether, washing the extracts with water, drying and evaporation of solvent below 40° C., 17 g. of tetramethylketone was obtained. This was distilled to obtain 14.6 g. of product, B.P. 62°–64° C. (15 mm.).

ii. The 2,2,6,6-tetramethylcyclohexanone (8 g.) obtained above was converted to the oxime and the latter compound reduced by the procedure of Example 47, Part ii, to provide 1.4 g. of the desired amine as a colorless liquid which was of suitable purity for use as intermediate.

iii. 2,2,5,5-Tetramethylcyclopentanone

To a slurry of 2.0 moles of sodium hydride (washed to remove oil) in tetrahydrofuran was added 190 ml. (2.0 mole) methyl sulfate at a fast rate. Simultaneously, 35.7 g. (0.425 mole) cyclopentanone in 50 ml. of the same solvent was added at a slow rate. The reaction mixture warmed spontaneously to a gentle reflux and hydrogen evolution was vigorous. When the addition was ccmpleted, the mixture was allowed to stir overnight at ambient temperature. After heating to reflux for two more hours a mixture of t-butanol in tetrahydrofuran was added and reflux continued for three hours. The reaction mixture was diluted with water, extracted with ethyl ether, the extracts washed with water, brine, dried over anhydrous MgSO$_4$ and the solvent evaporated to yield 48.2 g. of crude product. This was distilled to afford 24.2 g. of tetramethylketone, B.P. 63°–68° C., 40 mm.

By employing a lower mole ratio of methyl sulfate to cyclopentanone, the same method affords 2-methyl-cyclopentanone, 2,5-dimethylcyclopentanone and 2,2,5-trimethylcyclopentanone.

The following ketones are prepared in like manner when the appropriate starting materials are employed in the procedures of Part i and Part iii, above. The alpha-propyl and alpha-butylketones are prepared using e.g., the appropriate alkylbromide as alkylating agent.

2,2,6-trimethylcyclohexanone
2-ethylcyclopentanone
2,2,4,4-tetramethylcyclobutanone
2-methylcyclobutanone
2,2-dimethylcyclobutanone
2,4-diisopropylcyclobutanone
2-t-butylcyclopentanone
2,2-dimethyl-5-t-butylcyclopentanone
2,5-diisopropylcyclopentanone
2-sec-butylcyclopentanone
2-isobutylcyclohexanone
2-methylcycloheptanone
2-t-butylcycloheptanone
2,7-dimethylcycloheptanone
2,7-diisopropylcycloheptanone 3,5-dimethyltetrahydro-4H-pyran-4-one
3,5-diisopropyltetrahydro-4H-pyran-4-one
3,3,5,5-tetramethyltetrahydro-4H-pyran-4-one
3-methyl-5-t-butyltetrahydro-4H-pyran-4-one
3,3,5,5-tetramethyltetrahydro-4H-thiapyran-4-one
3-isopropyltetrahydro-4H-thiapyran-4-one
3,5-diisopropyltetrahydro-4H-thiapyran-4-one
3,-t-butyltetrahydro-4H-thiapyran-4-one
2-methyluetrahydro-4H-thiapyran-3-one
2,4-dimethyltetrahydro-4H-thiapyran-3-one
2-methylthiepane-3-one
4-methylthiepane-3-one
2,4-diethylthiepane-3-one
2,4-diisopropylthiepane-3-one
3,5-dimethylthiepane-4-one
3,3,5,5-tetramethylthiepane-4-one
4-methyltetrahydro-4-H-pyran-3-one
4-sec-butyltetrahydro-4H-pyran-3-one
2-isopropyltetrahydro.4H-pyran-3-one
2,4-diisopropyltetrahydro-4H-pyran-3one
2,4-dimethyltetrahydro-4H-pyran-3-one
2-methyloxepane-3-one
4-methyloxepane-3-one
2,4-dimethyloxepane-3-one
2,2,4,4-tetramethyloxepane-3-one
3-methyloxepane-4-one
5-methyloxepane-4-one
3,5-dimethyloxepane-4-one
3,3,5,5-tetramethyloxepane-4-one
3,5-diisopropyloxepane-4-one
3-t-butyloxepane-4-one
5-t-butyloxepane-4-one The ketones provided above are converted to the corresponding amines by conversion to the oxime and reduction with sodium in ethanol as described in Example 47, Part ii, or Leuckart reduction of the ketone as described in Example 46, Part ii.

PREPARATION D

2,4-Dimethyl-3-aminopentane

In a shaker bottle was placed 0.2 g. platinum dioxide and 10 ml. water. The slurry was hydrogenated at 50 psi (3.5 kg./cm$^2$) for 15 minutes. To the resulting slurry of platinum black was added 34.26 g. (0.30 mole) 2,4-dimethyl-3-pentanone, 20.0 g. (0.37 mole) ammonium chloride, 225 ml. ammonia saturated methanol and 25 ml. concentrated ammonium hydroxide. The resulting slurry was hydrogenated at 60 psi (4.2 kg./cm.$^2$) and room temperature for 20 hours, filtered, refluxed for for 1 hour and cooled. The mixture was adjusted to pH 2.0 with concentrated hydrochloric acid and the volume was reduced by evaporation at reduced pressure. After washing with 75 ml. ethyl ether, the aqueous solution was brought to pH 13 with 10M sodium hydroxide solution and extracted with three 100 ml. portions of ether. The extracts were combined, dried over anhydrous MgSO$_4$ and saturated with gaseous hydrogen chloride. The precipitated amine hydrochloride was collected by filtration, air dried and decomposed with 75 ml. 10M sodium hydroxide solution. The oily amine layer was separated and distilled at atmospheric pressure, B.P. 129°–132° C., yielding 17.6 g.

PREPARATION E

2,2,3,3-Tetramethylcyclopropylamine i. Ethyl 2,2,3,3-Tetramethylcyclopropanecarboxylate
The method of Mesheheryakov, *Chem. Abstr.*, 54, 24436d (1960) was employed. To a mixture of 19 g. (0.226 mole) of 2,3-dimethyl-2-butene and 2 g. of cupric sulfate is added at reflux a mixture of 51 g. (0.447 mole) ethyl diazoacetate and 19 g. of 2,3-dimethyl-2-butene. The resulting mixture is heated at reflux for 3 hours, cooled, filtered and distilled to afford 19.8 g. (26%) of the desired cyclic ester, B.P. 76°–77° (15 mm.)

ii. To 300 ml. of ethanol containing 40 g. of ammonia is added 17 g. (0.10 mole) of the ester obtained above and the resulting mixture allowed to stand overnight. After heating at reflux for one hour the ethanol was evaporated in vacuo to obtain 2,2,3,3-tetramethylcyclopropanecarboxamide.

A solution of 2.82 g. (0.02 mole) of the amide in 8 ml. tetrahydrofuran and 4 ml. of water is cooled to 5° C. and 10 ml. of 2M sodium hypochlorite added dropwise followed by 8 ml. of 20% (w/v) sodium hydroxide. The two phase mixture is stirred at 5° C. for 30 minutes then at 20° C. for one hour. The organic layer is extracted with ether, the ether layer extracted with M hydrochloric acid (3×20 ml.), the aqueous acidic layer is made strongly alkaline with sodium hydroxide and extracted with ether. The extracts are dried (Na$_2$SO$_4$) and the ether evaporated at 25° (50 mm.) to give 0.67 g. (25%) 2,3,3,3-tetramethylcyclopropylamine. $^1$H-NMR (CDCl$_3$) ppm (delta):

0.95 (6H, singlet); 1.00 (6H, singlet); 1.83 (1H, multiplet); 1.7 (2H, multiplet).

iii. The following substituted cyclopropylamines are prepared in an analogous fashion from the appropriate olefin.

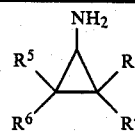

| R$^3$ | R$^4$ | R$^5$ | R$^6$ |
|---|---|---|---|
| CH$_3$ | H | CH$_3$ | H |
| CH$_3$ | H | H | H |
| i-CH$_3$H$_7$ | H | H | H |
| i-C$_3$H$_7$ | H | i-C$_3$H$_7$ | H |
| CH$_3$ | CH$_3$ | H | H |
| t-C$_4$H$_9$ | H | H | H |
| CH$_3$ | CH$_3$ | t-C$_4$H$_9$ | H |

PREPARATION F

2,2,5,5-Tetramethylcyclopentylamine

A flask was charged with 35 g. (0.61 mole) of 40% sodium dispersion in mineral oil. The oil was removed by washing with ethyl ether and decantation. The sodium was then mixed with 400 ml. of ether and a mixture of 32.8 g. (0.20 mole) 2,2,5,5-tetramethyladiponitrile, prepared by the method of Coffman *et al., J. Am. Chem. Soc.*, 80, 2868 (1957), and 400 ml. of tetrahydrofuran was added slowly. The resulting mixture was stirred at room temperature for 4 hours, the excess sodium decomposed by dropwise addition of saturated aqueous ammonium chloride, the organic layer washed with water, dried (Na$_2$SO$_4$) and evaporated to afford 25.1 g. of crude 2,2,5,5-tetramethylcyclopentylimine. The imine was dissolved in 75 ml. of ethanol and added dropwise to a flask containing 23.3 g. (1 mole) sodium shot. An additional 75 ml. ethanol was added and the mixture heated at reflux until the remaining sodium metal was consumed. The reaction mixture was diluted with water, acidified to pH 1 with concentrated hydrochloric acid, the aqueous phase washed with ether then made strongly basic by addition of sodium hydroxide. The organic layer was extracted with ether, washed with brine, dried (Na$_2$SO$_4$) and evaporated to dryness. The residue was distilled in vacuo to afford 6.6 g. (23%) of the desired amine, B.P. 60°–61° C. (20 mm.).

PREPARATION G

3-Amino-2,2,4,4-tetramethyloxetane

To 13.6 g. (0.12 mole) of diisopropylketone is added 0.2 ml. of phosphorus tribromide. To this is added dropwise at 10° C., 38.4 g. (0.24 mole) bromine and the mixture warmed to 55°–60° C. and held at this temperature for 1.5 hours. After cooling and partioning between chloroform and water, the organic layer is washed with sodium carbonate solution until neutral, dried and the solvent evaporated to obtain 2,4-dibromo-2,4-dimethyl-pentan-3-one.

To 0.1 mole of the dibromoketone in 160 ml. of ethanol is added a solution of 8 g. of sodium hydroxide in 80 ml. water and the resulting mixture is stirred at room temperature for 30 minutes. After diluting with water the reaction mixture is extracted with ethyl ether, the extracts washed with water, brine and dried (MgSO$_4$). The ether is evaporated to provide 2,4-dihydroxy-2,4-dimethyl-3-pentanone. This is dissolved in 50 ml. chloroform and 1.5 ml. concentrated sulfuric acid added dropwise. The resulting mixture is heated at reflux for five hours while removing water as its azeotropic mixture with chloroform. When no more water is evolved the reaction mixture is washed with water, the organic layer dried (MgSO$_4$) and solvent evaporated to provide 2,2,4,4-tetramethyloxetane-3-one which is purified by distillation.

The ketone is converted to the oxime and reduced with sodium/ethanol by the procedure of Example 47, Part ii.

PREPARATION H

3-Amino-2,2-dimethyloxetane

3-Hydroxy-3-methyl-2-butanone, 0.20 mole, is treated dropwise with a equimolar amount of bromine at room temperature and the resulting mixture stirred for three hours. The mixture is taken up in chloroform, washed with sodium carbonate solution until neutral, dried and solvent evaporated to obtain 1-bromo-3-hydroxy-3-methyl-2-butanone.

To 0.1 mole of the bromoketone in 160 ml. of ethanol is added a solution of 4 g. of sodium hydroxide in 80 ml. water and the mixture stirred at room temperature for 30 minutes. The mixture is diluted with water, extracted with ether, the extracts washed with water, brine and dried (MgSO$_4$). The solvent is evaporated and the residue taken up in 50 ml. of chloroform. To this is added dropwise 1.5 ml. of concentrated sulfuric acid and the resulting mixture heated at reflux while removing water as its azeotrope with chloroform. When water evolution is complete the resulting ketone is isolated and converted to the desired amine as described in Preparation G.

PREPARATION I

Employing the procedures of Preparation G and H but starting with the appropriate ketone or alphahydroxyketone in each case the following amines are prepared in like manner.

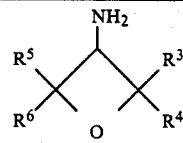

| R$^3$ | R$^4$ | R$^5$ | R$^6$ |
|---|---|---|---|
| CH$_3$ | H | H | H |
| CH$_3$ | H | t-C$_4$H$_9$ | H |
| CH$_3$ | C$_2$H$_5$ | CH$_3$ | C$_2$H$_5$ |
| CH$_3$ | H | CH$_3$ | H |
| CH$_3$ | CH$_3$ | C$_2$H$_5$ | C$_2$H$_5$ |
| i-C$_3$H$_7$ | H | H | H |
| i-C$_3$H$_7$ | H | i-C$_3$H$_7$ | H |
| C$_2$H$_5$ | C$_2$H$_5$ | H | H |

PREPARATION J

2-Amino-3,3-dimethyl-gamma-butyrolactone Hydrochloride

The method is that of Nagase et al., Chem. Pharm. Bull., 17, 398 (1969).

To a stirrei solution of 2,2-dimethylhydroacrylaldehyde [preparei from sec-butyraldehyie and formaldehyde by the method of Stiller, et al., J. Am. Chem. Soc., 62, 1785 (1940)]5.11 g. in methanol (25 ml.), a solution of ammonium chloride, 2.94 g., and sodium cyanide, 2.9 g., in water (40 ml.) is added dropwise. After stirring for three hours the mixture is saturated with ammonia gas and allowed to stand at room temperature overnight. The resulting mixture is concentrated in vacuo to a small volume and 40 ml. of concentrated ydrochloric acid is added. After refluxing for three hours the mixture is evaporated in vacuo and the residue crystallized from ethanol-ethyl ether and then from ethanol to give 2.2 g. of the title compound, M.P. 214°–215° C. (dec.).

Use of homologs of 2,2-dimethylhydracrylaldehyde in the above procedure affords the corresponding compounds of the formula

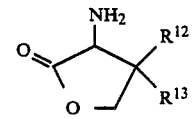

where one of R$^{12}$ and R$^{13}$ is alkyl having from one to four carbon atoms and the other is hydrogen or alkyl having from one to four carbon atoms.

PREPARATION K

4-Amino-3,3,5,5-tetramethyl-tetrahydro-4H-pyran-2-one i. Methyl 5-Hydroxy-2,2,4,4-tetramethyl-3-keto valerate A mixture of 172 g. (1.0 mole) methyl 2,2,4-trimethyl-3-ketovalerate, 5.4 g. (0.10 mole) sodium methoxide and 33 g. (0.36 mole) paraformalde in 250 ml. methanol is heated at reflux for eight hours. The mixture is quenched by addition of water, neutralized with hydrochloric acid, extracted with ethyl ether, washed with water, brine and solvent evaporated. The residue is purified by vacuum distillation or chromatography on silica gel to provide the purified product.

ii. 2,2,4,4-tetramethyl-2,4-dioxotetrahyiro.4H-pyran

A solution of 101 g. (0.50 mole) of the above product in 200 ml. methanol and 20 ml. concentrated hydrochloric acid is heated at reflux for two hours, cooled, poured into ice-water, extracted with ethyl ether, the extracts washed with sodium bicarbonate solution, water, dried and evaporated to dryness. The residue was heated in vacuo at 80°–100° C. for two hours to obtain product of suitable purity for use in the next step.

iii. The ketolactone obtained above is converted to the corresponding 4-oximino derivative and this reduced to the title compound by the procedure of Example 5, Part A.

PREPARATION L

4-Amino-3,3,5,5-tetramethyl-2-piperidone i. Methyl 5-Dibenzylamino-2,2,4,4-tetramethyl-3-ketovalerate hydrochloride To a mixture of 86 g. (0.50 mole) methyl 2,2,4-trimethyl-3-ketovalerate, 117 g. (0.64 mole) dibenzylamin hydrochloride and 19.8 g. (0.22 mole) paraformaldehyde is added a solution of 1 ml. of concentrated hydrochloric acid in 150 ml. 95% ethanol and the mixture is heated at reflux for four hours. The mixture is filtered, 500 ml. of hot acetone added to the filtrate and the resulting mixture cooled then refrigerated overnight. The precipitated product is collected by filtration, washed with acetone and dried.

ii. 3,3,5,5-tetramethylpiperidin-2,4-dione

The above hydrochloride salt is partitioned between 0.1 N sodium hydroxide solution and ethyl ether. The ether extracts are dried (MgSO$_4$) evaporated to dryness and the residue taken up in methanol. To the methanol solution is added 1 g. of 10% Pd/C and the mixture hydrogenated at 3–4 amtospheres pressure until hydrogen uptake is complete. The catalyst is removed by filtration, the filtrate heated at reflux for two hours, solvent evaporated and the residue heated at 70°–80° C. in vacuo for two hours. The residual product is purified by chromatography on silica gel.

iii. The piperidinedione obtained above is converted to the 4-oximino derivative and this reduced to the title 4-amino analog by the procedure of Example 5, Part A.

PREPARATION M 3,3,5,5-Tetramethylpyrrolidin-2,4-dione

A mixture of 80 g. of 2,2,4,4-tetramethyl-1,3-cyclobutanedione monoxime, prepared by the method of U.S. Pat. No. 3,125,569, and 250 ml. 98% (w/w) sulfuric acid was warmed at 50°–60° C. for one hour and allowed to stand overnight at room temperature. The reaction mixture was poured onto 800 g. ice, extracted with methylene chloride, the extracts washed with sodium bicarbonate solution, water, dried (MgSO$_4$) and evaporated to remove solvent. The resulting mixture of products was purified by column chromatography on silica gel and the fractions containing the title compound combined and evaporated to dryness.

The ketolactam thus obtained is converted to 3-amino-3,3,5,5-tetramethyl-2-pyrrolidone by methods described above.

We claim:

1. A D-amino acid amide compound of the formula

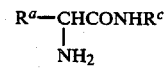

wherein $R^a$ is methyl, ethyl, isopropyl or n-propyl and $R^c$ is a member selected from the group consisting of fenchyl, diisopropylcarbinyl, d-methyl-t-butylcarbinyl, d-ethyl-t-butylcarbinyl, di-t-butylcarbinyl, cyclopropyl-t-butylcarbinyl, cyclopentyl-t-butylcarbinyl, dicyclo-propylcarbinyl,

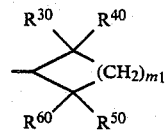

where $m_1$ is 1, 2 or 3 and when $m_1$ is 1: $R^{30}$, $R^{40}$, $R^{50}$ and $R^{60}$ are each methyl, when $m_1$ is 2: $R^{30}$ is methyl, ethyl or isopropyl and $R^{40}$, $R^{50}$ and $R^{60}$ are each methyl and are each hydrogen, or $R^{30}$, and $R^{50}$ are each methyl and $R^{40}$ and $R^{60}$ are each hydrogen, and when $m_1$ is 3:

(a) $R^{30}$ is isopropyl or t-butyl and $R^{40}$, $R^{50}$ and $R^{60}$ are each hydrogen (b) $R^{30}$ is ethyl, $R^{50}$ is methyl and $R^{40}$ and $R^{60}$ are each hydrogen, or (c) $R^{30}$ and $R^{40}$ are each methyl and $R^{50}$ and $R^{60}$ are each hydrogen or methyl.

2. A compound according to claim 1 wherein $R^a$ is methyl or ethyl and $R^c$ is dicyclopropylcarbinyl.

3. A compound according to claim 2 wherein $R^a$ is methyl.

* * * * *